(12) United States Patent
Tamagnan et al.

(10) Patent No.: US 7,700,616 B2
(45) Date of Patent: Apr. 20, 2010

(54) COMPOUNDS AND AMYLOID PROBES THEREOF FOR THERAPEUTIC AND IMAGING USES

(75) Inventors: Gilles D. Tamagnan, Woodbridge, CT (US); David Alagille, New Haven, CT (US); Herve Da Costa, New Haven, CT (US)

(73) Assignee: Molecular Neuroimaging, LLC., New Haven, CT (US)

(*) Notice: Subject to any disclaimer, the term of this patent is extended or adjusted under 35 U.S.C. 154(b) by 205 days.

(21) Appl. No.: 11/800,986

(22) Filed: May 8, 2007

(65) Prior Publication Data

US 2007/0258887 A1 Nov. 8, 2007

Related U.S. Application Data

(60) Provisional application No. 60/798,603, filed on May 8, 2006, provisional application No. 60/906,106, filed on Mar. 9, 2007.

(51) Int. Cl.
| | |
|---|---|
| A01N 43/42 | (2006.01) |
| A61K 31/44 | (2006.01) |
| A01N 43/64 | (2006.01) |
| A61K 31/41 | (2006.01) |
| C07D 221/02 | (2006.01) |
| C07D 471/02 | (2006.01) |
| C07D 491/02 | (2006.01) |
| C07D 513/02 | (2006.01) |
| C07D 513/00 | (2006.01) |

(52) U.S. Cl. .................. 514/299; 514/300; 514/301; 514/302; 514/303; 514/359; 546/112; 546/113; 546/114; 546/115; 546/118; 548/152; 548/153

(58) Field of Classification Search .............. 548/152, 548/153; 546/112, 113, 114, 115, 118, 121
See application file for complete search history.

(56) References Cited

U.S. PATENT DOCUMENTS

| | | | | |
|---|---|---|---|---|
| 4,533,612 | A | * 8/1985 | Eilingsfeld et al. | 430/58.5 |
| 4,962,011 | A | * 10/1990 | Aldag et al. | 430/281.1 |
| 6,114,175 | A | 9/2000 | Klunk et al. | 436/63 |
| 6,168,776 | B1 | 1/2001 | Klunk et al. | 424/1.11 |
| 6,274,119 | B1 | 8/2001 | Barrio et al. | 424/1.81 |
| 6,417,178 | B1 | 7/2002 | Klunk et al. | 514/150 |
| 6,878,363 | B2 | 4/2005 | Zaczek et al. | 424/9.1 |
| 7,119,105 | B2 | 10/2006 | Ellman et al. | 514/321 |
| 2002/0133019 | A1 | 9/2002 | Klunk et al. | 548/156 |
| 2003/0059369 | A1 | * 3/2003 | Kung et al. | 424/1.11 |
| 2003/0149250 | A1 | 8/2003 | Kung et al. | 534/14 |
| 2003/0236391 | A1 | 12/2003 | Klunk et al. | |
| 2005/0048000 | A1 | 3/2005 | Gervais et al. | 424/9.364 |
| 2005/0271584 | A1 | 12/2005 | Kung et al. | 424/1.11 |

FOREIGN PATENT DOCUMENTS

| | | | |
|---|---|---|---|
| EP | 476519 | * | 9/1991 |
| WO | 2002085903 | * | 10/2002 |
| WO | WO 2005/040337 | | 5/2005 |
| WO | WO 2006/014381 | | 2/2006 |
| WO | WO 2006/014382 | | 2/2006 |
| WO | WO 2007/035405 | | 3/2007 |

OTHER PUBLICATIONS

Cai et al., Tetrahedron Letters (2006), 47(26), 4449-4452.*
Zeng et al., Bioorganic & Medicinal Chemistry Letters (2006), 16(11), 3015-3018.*
Zhuang et al., Journal of Medicinal Chemistry (2006), 49(9), 2841-2844.*
Kung et al., Brain Research (2002), 956(2), 202-210.*
Zhuang et al., Journal of Medicinal Chemistry (2003), 46(2), 237-243.*
Lindsley et al., Science of Synthesis (2004), 17, 357-447.*
Metroke et al., Progress in Organic Coatings (2003), 46(4), 250-258.*
Kim et al., Bulletin of the Korean Chemical Society (2001), 22(9), 999-1004.*
Agneta Nordberg, "Pet Imaging of Amyloid in Alzheimer's Disease", The Lancet Neurology, Sep. 2004, vol. 3, pp. 519-527.

* cited by examiner

*Primary Examiner*—D. Margaret Seaman
*Assistant Examiner*—Niloofar Rahmani
(74) *Attorney, Agent, or Firm*—Weingarten, Schurgin, Gagnebin & Lebovici LLP

(57) ABSTRACT

The present invention provides compounds and amyloid probes thereof that allow for an antemortem method of diagnosing AD and quantitating the extent or progression of amyloid deposits (plaques) by in vivo imaging of amyloid and/or amyloid deposits in the regions of the brain. Preferably, an amyloid probe of the invention can cross the blood-brain barrier and distinguish AD brain from normal brain. An amyloid probe can be administered to a patient in amounts suitable for in vivo imaging of amyloid deposits. Amyloid probes of the invention can also be used to detect and quantitate amyloid deposits in diseases including, without limitation, Down's syndrome, familial AD and homozygotes for the apolipoprotein E4 allele. In one aspect, the compounds may be used in the treatment or prophylaxis of diseases that include, without limitation, AD and type 2 diabetes mellitus. The compounds and amyloid probes of the invention include analogs, salts, pharmaceutical compositions, derivatives, prodrugs, racemic mixtures or tautomeric forms thereof.

7 Claims, 7 Drawing Sheets

IC50
Binding
Data 8.2nM 8.7nM 9.7nM

11nM

15nM

17nM

20nM

IC50 Binding Data

24nM

35nM

36nM

57nM

57nM

85nM

510nM

860nM

COMPOUNDS AND AMYLOID PROBES THEREOF FOR THERAPEUTIC AND IMAGING USES

CROSS-REFERENCE TO RELATED APPLICATIONS

This application claims priority under 35 U.S.C. §119(e) to U.S. Provisional Patent Application No. 60/798,603 filed May 8, 2006 and entitled "COMPOUNDS AND AMYLOID PROBES THEREOF FOR IN VIVO IMAGING," and U.S. Provisional Patent Application No. 60/906,106 filed Mar. 9, 2007 and entitled "COMPOUNDS AND AMYLOID PROBES THEREOF FOR IN VIVO IMAGING," the whole of which are incorporated by reference herein in entirety.

BACKGROUND OF THE INVENTION

Alzheimer's disease (AD) is a neurodegenerative illness characterized by memory loss and other cognitive deficits. McKhann et al., *Neurology*, 34: 939 (1984). It is the most common cause of dementia in the United States. AD can strike persons as young as 40-50 years of age, yet, because the presence of the disease is difficult to determine without dangerous brain biopsies, the time of onset is unknown. The prevalence of AD increases with age, with estimates of the affected population reaching as high as 40-50% by ages 85-90. Evans et al., *JAMA*, 262: 2551 (1989); Katzman, *Neurology*, 43: 13 (1993).

In practice, AD is definitively diagnosed through examination of brain tissue, usually at autopsy. Khachaturian, *Arch. Neurol.*, 42: 1097 (1985); McKhann et al., *Neurology*, 34: 939 (1984). Neuropathologically, this disease is characterized by the presence of neuritic plaques (NP), neurofibrillary tangles (NFT) and neuronal loss along with a variety of other findings. Mann, *Mech. Ageing Dev.*, 31: 213 (1985). Post-mortem slices of brain tissue of victims of Alzheimer's disease exhibit the presence of amyloid in the form of proteinaceous extracellular cores of the neuritic plaques that are characteristic of AD.

The amyloid cores of these neuritic plaques are composed of a protein called the β-amyloid (Aβ) that is arranged in a predominately beta-pleated sheet configuration. Mori et al., *Journal of Biological Chemistry*, 267: 17082 (1992); Kirschner et al., *PNAS*, 83: 503 (1986). Neuritic plaques are an early and invariant aspect of the disease. Mann et al., *J. Neurol. Sci.*, 89: 169; Mann, *Mech. Ageing Dev.*, 31: 213 (1985); Terry et al., *J. Neuropathol. Exp. Neurol.*, 46: 262 (1987).

The initial deposition of Aβ probably occurs long before clinical symptoms are noticeable. The currently recommended "minimum microscopic criteria" for the diagnosis of AD is based on the number of neuritic plaques found in the brain. Khachaturian, *Arch. Neurol.*, 42: 1097 (1985). Unfortunately, assessment of neuritic plaque counts must be delayed until after death.

Amyloid-containing neuritic plaques are a prominent feature of selective areas of the brain in AD as well as Down's Syndrome and in persons homozygous for the apolipoprotein E4 allele, who are very likely to develop AD. Corder et al., *Science*, 261: 921 (1993); Divry, P., *J. Neurol. Psych.*, 27: 643 (1927); Wisniewski et al., Re-Examination of the Pathogenesis of the Senile Plaque: *Progress in Neuropathology*, (Grune and Stratton, N.Y. 1973), pp. 1-26. Brain amyloid is readily demonstrated by staining brain sections with thioflavin S or Congo red. Puchtler et al., *J. Histochem Cytochem*, 10: 35 (1962). Congo red stained amyloid is characterized by a dichroic appearance, exhibiting a yellow-green polarization color. The dichroic binding is the result of the beta-pleated sheet structure of the amyloid proteins. Glenner, G., N. *Eng. J. Med.*, 302:1283 (1980). A detailed discussion of the biochemistry and histochemistry of amyloid can be found in Glenner, G., N. *Eng. J. Med.*, 302: 1333 (1980).

Amyloidosis is a condition characterized by the accumulation of various insoluble, fibrillar proteins, generically termed "amyloid," in the tissues of a patient. Amyloidosis is a slowly progressive condition, which can lead to significant morbidity and death. A diverse group of diseases or disease processes fall under the "amyloidosis" rubric, and can be termed amyloidosis-related diseases. An amyloid deposit is formed by the aggregation of amyloid proteins, followed by the further combination of aggregates and/or amyloid proteins. Formation and accumulation of aggregates of Aβ peptides in the brain are critical factors in the development and progression of AD. The fibrillar aggregates of amyloid peptides, $A\beta_{1-40}$ and $A\beta_{1-42}$, are major metabolic peptides derived from amyloid precursor proteins found in senile plaques and cerebrovascular amyloid deposits in AD patients. Xia et al., *J. Proc. Natl. Acad Sci. U.S.A.*, 97: 9299 (2000). Prevention and reversal of Aβ plaque formation are being targeted as a treatment for this disease. Selkoe, D., *JAAM*, 283: 1615 (2000); Wolfe, M. S., et al., *J. Med Chem.*, 41: 6 (1998); Skovronsky, D. M. et al., *Trends Pharmacol. Sci.*, 21: 161 (2000).

In addition to the role of amyloid deposits in Alzheimer's disease, the presence of amyloid deposits has been shown in diseases such as glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, Islets of Langerhans diabetes Type II insulinoma and other amyloidosis-related diseases.

Thus far, diagnosis of AD has been achieved mostly through clinical criteria evaluation, brain biopsies and post-mortem tissue studies. Research efforts to develop methods for diagnosing AD in vivo include (1) genetic testing, (2) immunoassay methods and (3) imaging techniques.

Evidence that abnormalities in Aβ metabolism are necessary and sufficient for the development of AD is based on the discovery of point mutations in the Aβ precursor protein in several rare families with an autosomal dominant form of AD. Hardy, *Nature Genetics*, 1: 233 (1992); Hardy et al., *Science*, 256: 184 (1992). These mutations occur near the N and C-terminal cleavage points necessary for the generation of Aβ from its precursor protein. St. George-Hyslop et al., *Science*, 235: 885 (1987); Kang et al., *Nature*, 325: 733 (1987). Genetic analysis of a large number of AD families has demonstrated, however, that AD is genetically heterogeneous. St. George-Hyslop et al., *Nature*, 347: 194 (1990). Linkage to chromosome 21 markers is shown in only some families with early-onset AD and in no families with late-onset AD. More recently, a gene on chromosome 14, whose product is predicted to contain multiple transmembrane domains and resembles an integral membrane protein, has been identified by Sherrington et al., *Nature*, 375: 754 (1995). This gene may account for up to 70% of early-onset autosomal dominant AD. Preliminary data suggests that this chromosome 14 mutation causes an increase in the production of Aβ. Scheuner et al., *Soc. Neurosci. Abstr.*, 21: 1500 (1995). A mutation on a very similar gene has been identified on chromosome 1 in Volga German kindreds with early-onset AD. Levy-Lahad et al., *Science*, 269: 973 (1995).

Screening for apolipoprotein E genotype has been suggested as an aid in the diagnosis of AD. Scott, *Nature*, 366: 502 (1993); Roses, *Ann. Neurol.*, 38: 6 (1995). Difficulties arise with this technology, however, because the apolipoprotein E4 allele is only a risk factor for AD, not a disease marker. It is absent in many AD patients and present in many non-demented elderly people. Bird, *Ann. Neurol.*, 38: 2 (1995).

Immunoassay methods have been developed for detecting the presence of neurochemical markers in AD patients and to detect an AD related amyloid protein in cerebral spinal fluid. Warner, *Anal. Chem.*, 59: 1203A (1987). These methods for diagnosing AD have not been proven to detect AD in all patients, particularly, at early stages of the disease, and are relatively invasive, requiring a spinal tap. Also, attempts have been made to develop monoclonal antibodies as probes for imaging of Aβ. Majocha et al., *J. Nucl. Med.*, 33: 2184 (1992). The major disadvantage of antibody probes is the difficulty in getting these large molecules across the blood-brain barrier. Using antibodies for in vivo diagnosis of AD would require marked abnormalities in the blood-brain barrier in order to gain access into the brain. There is no convincing functional evidence that abnormalities in the blood-brain barrier reliably exist in AD. Kalaria, *Cerebrovascular & Brain Metabolism Reviews*, 4: 226 (1992).

Radiolabeled Aβ peptides have been used to label diffuse, compact and neuritic type plaques in sections of AD brain. However, these peptides share all of the disadvantages of antibodies. Specifically, peptides do not normally cross the blood-brain barrier in amounts necessary for imaging and because these probes react with diffuse plaques, they may not be specific for AD.

Data also suggest that amyloid binding compounds will have therapeutic potential in AD and type 2 diabetes mellitus. Morphological reactions including reactive astrocytosis, dystrophic neurites, activated microglia cells, synapse loss and full complement activation found around neuritic plaques all signify that neurotoxic and cell degenerative processes are occurring in the areas adjacent to these Aβ deposits. Joachim et al., *Am. J. Pathol.*, 135: 309 (1989); Masliah et al., 137: 1293 (1990); Lue et al., *Dementia*, 3: 308 (1992). Aβ-induced neurotoxicity and cell degeneration has been reported in a number of cell types in vitro. Yankner et al., *Science*, 250: 279 (1990); Roher et al., *BBRC*, 174: 572 (1991); Frautschy et al., *Proc. Natl. Acad. Sci.*, 88: 83362 (1991); Shearman et al., 91: 1470 (1994). It has been shown that aggregation of the Aβ peptide is necessary for in vitro neurotoxicity. Yankner, *Neurobiol. Aging*, 13: 615 (1992). Thus far, several laboratories have reported results which suggest that Congo red inhibits Aβ-induced neurotoxicity and cell degeneration in vitro. Burgevin et al., *NeuroReport*, 5: 2429 (1994); Lorenzo et al., *Proc. Natl. Acad. Sci.*, 91: 12243 (1994); Pollack et al., *Neuroscience Letters*, 184: 113 (1995); Pollack et al., *Neuroscience Letters*, 197: 211 (1995). The mechanism appears to involve both inhibition of fibril formation and prevention of the neurotoxic properties of formed fibrils. Lorenzo et al., *Proc. Natl. Acad. Sci.*, 91: 12243 (1994). Congo red also has been shown to protect pancreatic islet cells from the toxicity caused by amylin. Lorenzo et al., *Proc. Natl. Acad. Sci.*, 91: 12243 (1994). Amylin is a fibrillar peptide similar to Aβ, which accumulates in the pancreas in type 2 diabetes mellitus.

The inability to assess amyloid deposition in AD until after death impedes the study of this devastating illness. Histological analysis of biopsy or autopsy materials also has its drawbacks. As such, a method of quantifying amyloid deposition before death is needed both as a diagnostic tool in mild or clinically confusing cases as well as in monitoring the effectiveness of therapies targeted at preventing Aβ deposition. Moreover, it remains of utmost importance to develop a safe and specific method for diagnosing AD before death by imaging amyloid in brain parenchyma in vivo. Even though various attempts have been made to diagnose AD in vivo, currently, there are few antemortem probes for brain amyloid. To date, simple, noninvasive methods for detecting and quantitating amyloid deposits in a patient have been eagerly sought. Thus, a need exists for amyloid binding compounds which enter the brain and bind selectively to amyloid. Similarly, amyloid binding compounds are also needed for detecting and quantitating amyloid deposits in other disease types including, for example, those previously mentioned. Amyloid binding compounds may also be needed for their therapeutic potential in the treatment and prophylaxis of, for example, AD and type 2 diabetes mellitus.

SUMMARY OF THE INVENTION

The present invention relates to compounds and amyloid probes thereof that allow for a safe and specific method of diagnosing and quantitating AD before death by in vivo imaging of amyloid and/or amyloid deposits in, for example, regions of the brain and brain parenchyma. The invention also relates to methods for identifying, detecting and/or quantitating AD amyloid deposits and/or plaque in the brain before a patient's death, using high-affinity amyloid probes and/or labeled compounds of the invention, which have low toxicity, can cross the blood-brain barrier and can distinguish an AD brain from a normal brain. Preferably, the compounds or amyloid probes of the invention have a low toxicity at an effective amount or dosage including dosages effective for therapeutic or imaging (for example, identifying, diagnosing, evaluating, detecting and/or quantitating amyloid deposits or an amyloidosis-related disease state) uses. For example, an amyloid probe of the invention can be administered to a patient in an amount suitable for in vivo imaging of amyloid and/or amyloid deposits (plaques) or aggregates as well as amyloid-like aggregates and tau or synuclein aggregates. Moreover, the present invention relates to compounds and amyloid probes thereof that bind preferentially to or interact with amyloid proteins or precursors, portions, fragments and peptides thereof and/or their deposits as well as deposits that comprise one or more amyloid and/or amyloidogenic proteins. Amyloid probes of the invention can also be used to detect and quantitate amyloid deposits in such diseases as, for example, AD, familial AD, homozygotes for the apolipoprotein E4 allele, glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease and Islets of Langerhans diabetes Type II insulinoma.

In another aspect, the compounds of the invention may also be used in the treatment or prophylaxis of diseases that include, for example, AD and type 2 diabetes mellitus. The compounds of the invention can also be used in the treatment or prophylaxis of a disease state or malady characterized by or associated with amyloid deposits or amyloidosis. Generally, prophylactic or prophylaxis relates to a reduction in the likelihood of the patient developing a disorder such as AD or proceeding to a diagnosis state for the disorder. For example, the compounds of the invention can be used prophylacticly as a measure designed to preserve health and prevent the spread or maturation of disease in a patient. It is also appreciated that the various modes of treatment or prevention of a disease such as an amyloidosis-related disease or condition can mean "substantial" treatment or prevention, which includes total but also less than total treatment or prevention, and in which some biologically or medically relevant result is achieved. Furthermore, treatment or treating as well as alleviating can refer to therapeutic treatment and prophylactic or preventative measures in which the object is to prevent, slow down (lessen) a disease state, condition or malady. For example, a subject can be successfully treated for an amyloidosis-related disease if, after receiving through administration an effective or therapeutic amount of one or more compounds of the invention, the subject shows observable and/or measurable reduction in or absence of one or more signs and symptoms of the particular disease such as, but not limited to, reduced morbidity and mortality, or improvement in quality of life issues. The invention also provides for methods of administering one or more compounds of the invention to a patient in an effective amount for the treatment or prophylaxis of a disease such as, for example, AD or type 2 diabetes mellitus.

The compounds of the invention can also be administered to a patient along with other conventional therapeutic agents that may be useful in the treatment or prophylaxis of amyloidosis-related diseases. In one aspect, a method is provided for administering an effective amount of one or more compounds of the invention to a patient suffering from or believed to be a risk of suffering from a disease characterized by amyloid deposition or amyloidosis. Moreover, the invention relates to treating an amyloidosis-related disease by administering an effective amount of one or more compounds to a patient in need thereof. The methods of the invention can also comprise administering, either sequentially or in combination with one or more compounds of the invention, a conventional therapeutic agent in an amount that can potentially or synergistically be effective for the treatment or prophylaxis of an amyloidosis-related disease. Exemplary therapeutic agents for use in combination therapies with one or more compounds of the invention include, but are not limited to, anti-inflammatory drugs, therapeutic antibodies and cholesterol lowering drugs such as, for example, statins. Fassbender et al., *PNAS*, 98: 5856 (2001); DeMattos et al., *PNAS*, 98: 8850 (2001); Clark et al., *An. Intern. Med.*, 55: 15 (2004).

The compounds and amyloid probes of the invention also include analogs, salts, pharmaceutical compositions, derivatives, prodrugs or racemic mixtures thereof. Moreover, any methods, kits, assays or uses (including, for example, those herein) for a compound or amyloid probe of the invention can be performed with or employ one or more such analogs, salts, pharmaceutical compositions, derivatives, prodrugs or racemic mixtures. Preferably, the compounds or amyloid probes of the invention are amyloid binding compounds or a water soluble, non-toxic salt thereof. In one aspect, the compounds of the invention are each capable of being readily modified to be an amyloid probe that comprises one or more detectable markers, tags or labels by conventional techniques known to those of ordinary skill in the art. Ellis et al., *Aust. J. Chem.*, 26: 907 (1973); Wilson et al., *J. Org. Chem.*, 51: 4833 (1986); Wilbur et al., *J. Label. Compound. Radiopharm.*, 19: 1171 (1982); Chumpradit et al., *J. Med. Chem.*, 34: 877 (1991); Chumpradit et al., *J. Med. Chem.*, 32: 1431 (1989); Kabalka et al., *J. Label. Compound. Radiopharm.*, 19: 795 (1982); Koch et al., *Chem. Ber.*, 124: 2091 (1991); H. Mach et al., *J. Med. Chem.*, 36: 3707 (1993); Arora et al., *J. Med. Chem.*, 30: 918 (1987); March, J., Advanced Organic Chemistry: *I Reactions, Mechanisms, and Structure* (3rd Ed., 1985); Morrison and Boyd, Organic Chemistry (6th Ed., 1992).

The invention relates to compounds and amyloid probes that can target amyloid deposits (plaques) in vivo or in vitro. The compounds and/or probes of the invention can be administered to a subject in effective amounts for therapeutic (for example, treating or preventing an amyloidosis-related disease state) or imaging (for example, identifying, diagnosing, evaluating, detecting and/or quantitating amyloid deposits or an amyloidosis-related disease state) applications. The compounds or amyloid probes of the invention can comprise the structure or formula

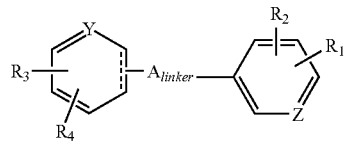

in which $R_1$, $R_2$, $R_3$ and $R_4$ are the same or different and can independently be H, F, Cl, Br, I, $NO_2$, CN, $CF_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, $OR_6$, $NR_5R_6$ or $R_6$, $R_5$ can be $C_nH_{2n+1}$ or $-CH_2-CH=CH-I$ ((E) or (Z) configuration) and $R_6$ can be $C_nH_{2n+1}$, $-[CH_2-CH_2-O]_m-R_5$, where n and m can each independently be 0, 1, 2, 3, 4, 5, 6 or 7 and a dashed bond ( - - - ) represents an optional bond, Y and Z can each independently be CH or N and $A_{linker}$ can be any suitable linker including, for example, one or more heteroaryl, aralkyl, aryl, alkyl, alkenyl, alkynyl and/or heterocycle groups, each of which can independently comprise one or more single, double or triple bonds (for example, alkenyl or alkynyl groups) and substituents that include, for example, $NO_2$, CN, $CF_3$, alkyl, alkyl, alkenyl, alkoxy, monoalkylamine, dialkylamine, hydroxyalkyl, halo, haloalkyl, alkylthio, alkylsulfonyl, heteroatom, heteroaryl, aralkyl, aryl, heterocyclic, carboxy, esterified carboxy and/or amidate carboxy groups. Preferably, an amyloid probe of the invention can comprise one or more substituents as a label (marker or tag). Exemplary labels include radionuclides, radioisotopes or isotopes. For example, an amyloid probe of the invention comprises one or more $R_1$, $R_2$, $R_3$, $R_4$, $R_5$ and $R_6$, each of which can independently comprise (for example, $R_1$ can be $^{131}I$ or $CH_2-CH_2-{}^{131}I$) $^{131}I$, $^{124}I$, $^{125}I$, $^{3}H$, $^{123}I$, $^{18}I$, $^{19}F$, $^{11}C$, $^{75}Br$, $^{13}C$, $^{13}N$, $^{15}O$, $^{76}Br$, $CH_2-CH_2$-label, $O-CH_2-CH_2$-label, $CH_2-CH_2-CH_2$-label, $O-CH_2-CH_2-CH_2$-label, $-[OCH_2-CH_2]_n$-label, $O-CH_2-CH=CH$-label ((E) or (Z) configuration), $N-CH_2-CH=CH$-label ((E) or (Z) configuration) in which "label" can independently be $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$, $^{11}C$ or $^{13}C$, or $^{11}C$ or $^{13}C$ can be a label (mark or tag) as a substituent of a lower alkyl group, $(CH_2)_nOR$, $CL_3$, $CH_2-CH_2$-L, $O-CH_2-CH_2$-L, $CH_2-CH_2-CH_2$-L, $O-CH_2-CH_2-CH_2$-L, CN, (C=O)-R, (C=O)N(R)$_2$, O(CO)R, OR, COOR, aryl, CR=CR-aryl or $CR_2-CR_2$-aryl in which L can be a halogen (for example, $^{13}CH_2-CH_2-F$) and R can be H, F, Cl, Br, I or a lower alkyl group. A detectable label for an amyloid probe can be included as an additional substituent (for example, group) to a compound of the invention or as an alternative substituent for any substituents that are present. For example, a label (tag or marker) included as an additional substituent to the group —CH₂—CH═CH₂ of a compound of the invention can be CH₂—CH₂—CH₂—¹³¹I. Moreover, a detectable label provided as an alternative substituent for one or more substituents present for a compound of the invention can, by way of example, include CH₂—CH₂—CH₃ to CH₂—CH₂—CH₂—¹³¹I, or —CH₂—CH═CH—I to —CH₂—CH═CH—¹²³I.

In one aspect, the invention relates to a compound or amyloid probe thereof comprising the structure or formula

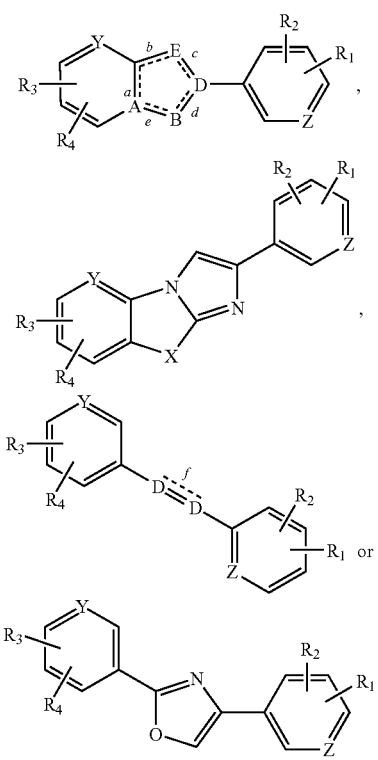

in which R₁, R₂, R₃ and R₄ are the same or different and can independently be H, F, Cl, Br, I, NO₂, CN, CF₃, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, OR₆, NR₅R₆ or R₆, R₅ can be C$_n$H$_{2n+1}$ or —CH₂—CH═CH—I ((E) or (Z) configuration) and R₆ can be C$_n$H$_{2n+1}$, —[CH₂—CH₂—O]$_m$—R₅, where n and m can each independently be 0, 1, 2, 3, 4, 5, 6 or 7, A and D can each independently be N or C, E, Y and Z can each independently be CH or N, B can be S, O, N or CH and a, b, c, d, e and f each independently represent an optional bond, provided that when A and E are N, then B can be CH, D can be C and b and d can each be a bond (to provide double bonds), or provided that when B, D and E are N, then A can be C, b and e can each be a bond (to provide double bonds), or provided that when E is N and B is O or S, then A and D can be C, a and c can each be a bond (to provide double bonds), or further provided that when D is C, then f can be a bond (to provide a triple bond of C≡C) or when D is N, then f is not a bond (to provide a double bond of N═N). For example, an amyloid probe of the invention can comprise one or more substituents as a radiolabel (marker or tag). Preferably, an amyloid probe of the invention comprises one or more of R₁, R₂, R₃, R₄, R₅ and R₆, each of which can independently comprise (for example, R₁ can be ¹³¹I or CH₂—CH₂—¹³¹I) ¹³¹I, ¹²⁴I, ¹²⁵I, ³H, ¹²³I, ¹⁸I, ¹⁹F, ¹¹C, ⁷⁵Br, ¹³C, ¹³N, ¹⁵O, ⁷⁶Br, CH₂—CH₂-label, O—CH₂—CH₂-label, CH₂—CH₂—CH₂-label, O—CH₂—CH₂—CH₂-label, —[OCH₂—CH₂]$_n$-label, O—CH₂—CH═CH-label ((E) or (Z) configuration), N—CH₂—CH═CH-label ((E) or (Z) configuration) in which "label" can independently be ¹³¹I, ¹²⁴I, ¹²⁵I, ³H, ¹²³I, ¹⁸F, ¹⁹F, ¹¹C, ⁷⁵Br, ¹³C, ¹³N, ¹⁵O, ⁷⁶Br, ¹¹C or ¹³C, or ¹¹C or ¹³C can be a label (mark or tag) as a substituent of a lower alkyl group, (CH₂)$_n$OR, CL₃, CH₂—CH₂-L, O—CH₂—CH₂-L, CH₂—CH₂—CH₂-L, O—CH₂—CH₂—CH₂-L, CN, (C═O)—R, (C═O)N(R)₂, O(CO)R, OR, COOR, aryl, CR═CR-aryl or CR₂—CR₂-aryl in which L can be a halogen (for example, ¹³CH₂—CH₂—F) and R can be H, F, Cl, Br, I or a lower alkyl group.

In one aspect, the invention relates to an in vivo or in vitro method for detecting amyloid deposits. The invention also relates to an in vivo or in vitro method for detecting in a subject one or more amyloid deposits comprising one or more amyloid or amyloidogenic proteins. For example, a method of the invention can comprise administering to a subject thought to be of risk for or suffering from a disease associated with amyloid deposits or amyloidosis, a detectable quantity or effective amount of a compound or amyloid probe thereof (or analogs, salts, pharmaceutical compositions, derivatives, prodrugs or racemic mixtures thereof) comprising

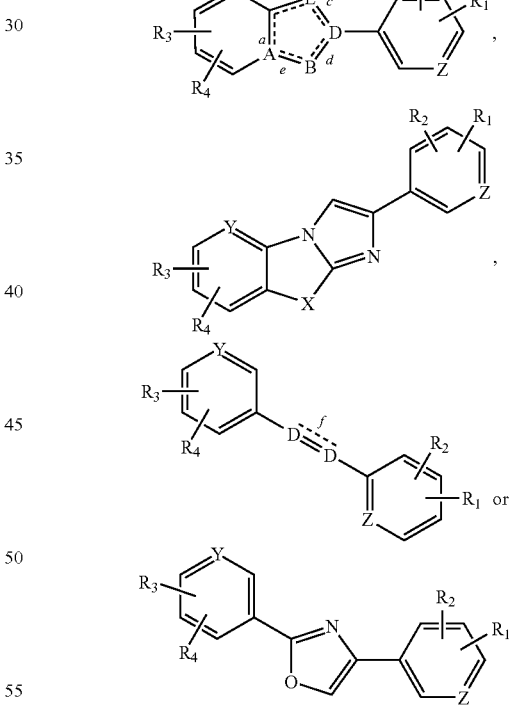

in which R₁, R₂, R₃ and R₄ are the same or different and can independently be H, F, Cl, Br, I, NO₂, CN, CF₃, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, OR₆, NR₅R₆ or R₆, R₅ can be C$_n$H$_{2n+1}$ or —CH₂—CH═CH—I ((E) or (Z) configuration) and R₆ can be C$_n$H$_{2n+1}$, —[CH₂—CH₂—O]$_m$—R₅, where n and m can each independently be 0, 1, 2, 3, 4, 5, 6 or 7, A and D can each independently be N or C, E, Y and Z can each independently be CH or N, B can be S, O, N or CH and a, b, c, d, e and f each independently represent an optional bond, provided that when A and E are N, then B can be CH, D can be C and b and d can each be a bond (to provide double bonds), or provided that when B, D and E are N, then A can be C, b and e can each be a bond (to provide double bonds), or provided that when E is N and B is O or S, then A and D can be C, a and c can each be a bond (to provide double bonds), or further provided that when D is C, then f can be a bond (to provide a triple bond of C≡C) or when D is N, then f is not a bond (to provide a double bond of N=N), and detecting the binding of the compound or amyloid probe thereof to an amyloid deposit comprising one or more amyloid or amyloidogenic proteins. For example, an amyloid probe used in conjunction with a method of the invention can comprise one or more substituents-as a radiolabel (marker or tag). Preferably, an amyloid probe of the invention comprises one or more of $R_1$, $R_2$, $R_3$, $R_4$, $R_5$ and $R_6$, each of which can independently comprise (for example, $R_1$ can be $^{131}$I or $CH_2$—$CH_2$—$^{131}$I) $^{131}$I, $^{124}$I, $^{125}$I, $^3$H, $^{123}$I, $^{18}$I, $^{19}$F, $^{11}$C, $^{75}$Br, $^{13}$C, $^{13}$N, $^{15}$O, $^{76}$Br, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH-label ((E) or (Z) configuration), N—$CH_2$—CH=CH-label ((E) or (Z) configuration) in which "label" can independently be $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C can be a label (mark or tag) as a substituent of a lower alkyl group, $(CH_2)_n$OR, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

The invention also relates to a compound or amyloid probe thereof comprising the structure or formula

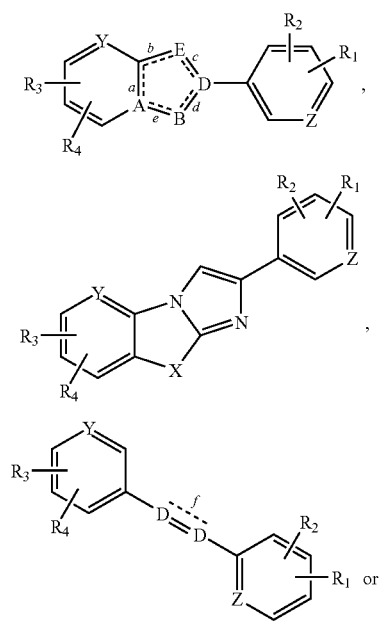

-continued

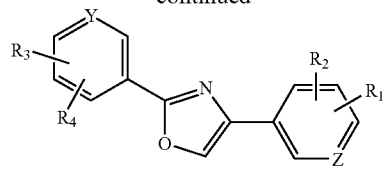

wherein $R_1$ is H, F, Cl, Br, I, NO$_2$, CN, CF$_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, OR$_6$, NR$_5$R$_6$ or R$_6$, $R_2$ is H, F, Cl, Br, I, NO$_2$, CN, CF$_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, OR$_6$, NR$_5$R$_6$ or R$_6$, $R_3$ is H, F, Cl, Br, I, NO$_2$, CN, CF$_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, OR$_6$, NR$_5$R$_6$ or R$_6$, $R_4$ is H, F, Cl, Br, I, NO$_2$, CN, CF$_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, OR$_6$, NR$_5$R$_6$ or R$_6$, $R_5$ is $C_nH_{2n+1}$ or —$CH_2$—CH=CH—I ((E) or (Z) configuration) and $R_6$ is $C_nH_{2n+1}$, —[$CH_2$—$CH_2$—O]$_m$R$_5$, where n and m are independently 0, 1, 2, 3, 4, 5, 6 or 7, A is N or C, D is N or C, E is CH or N, Y is CH or N, Z is CH or N, B is S, O, N or CH and a, b, c, d, e and f each independently represent an optional bond, provided that when A and E are N, then B is CH, D is C and b and d are each a bond (to provide double bonds), or provided that when B, D and E are N, then A is C, b and e are each a bond (to provide double bonds), or provided that when E is N and B is O or S, then A and D are C, a and c are each a bond (to provide double bonds), or further provided that when D is C, then f is a bond (to provide a triple bond of C≡C) or when D is N, then f is not a bond (to provide a double bond of N=N). For example, an amyloid probe of the invention can comprise one or more substituents as a radiolabel (marker or tag). Preferably, an amyloid probe of the invention comprises one or more of $R_1$, $R_2$, $R_3$, $R_4$, $R_5$ and $R_6$, each of which can independently comprise (for example, $R_1$ can be $^{131}$I or $CH_2$—$CH_2$—$^{131}$I) $^{131}$I, $^{124}$I, $^{125}$I, $^3$H, $^{123}$I, $^{18}$I, $^{19}$F, $^{11}$C, $^{75}$Br, $^{13}$C, $^{13}$N, $^{15}$O, $^{76}$Br, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH-label ((E) or (Z) configuration), N—$CH_2$—CH=CH-label ((E) or (Z) configuration) in which "label" can independently be $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C can be a label (mark or tag) as a substituent of a lower alkyl group, $(CH_2)_n$OR, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

In one aspect, a compound of the invention can comprise one or more of the exemplary structures or formulas of Table 1. The compound or amyloid probe of the structure or formula

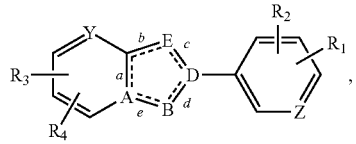

,

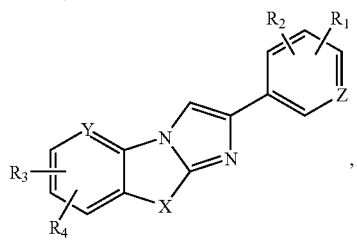

,

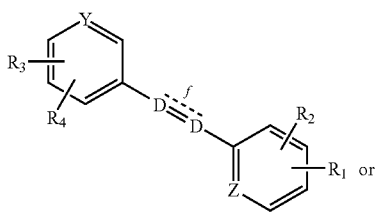

or

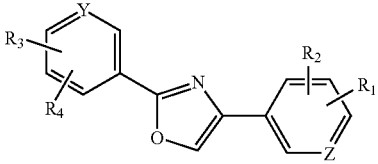

can also comprise a compound or amyloid probe of Table 1.

TABLE 1

| Structure | Substituents |
|---|---|
| 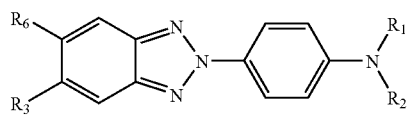 | $R_1$ is $CnH_2n + 1$, (E)-$CH_2CHCH$=I or (Z)-$CH_2CHCH$=I, $R_2$ is $CnH_2n + 1$, $R_3$ is $CnH_2n + 1$, F, Cl, Br, I or $OR_1$ and $R_6$ is $CnH_2n + 1$, F, Cl, Br, I or $OR_1$, where $R_1$ is $CnH_2n + 1$, (E)-$CH_2CH$=CH—I or (Z)-$CH_2CH$=CH—I and n is 0, 1, 2, 3, 4 or 5 |
| 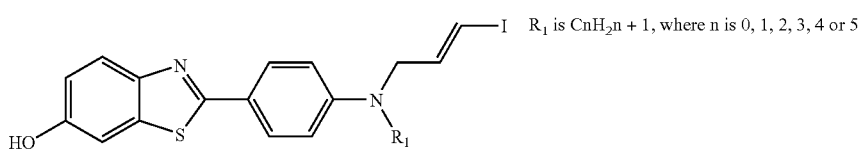 | $R_1$ is $CnH_2n + 1$, where n is 0, 1, 2, 3, 4 or 5 |
| 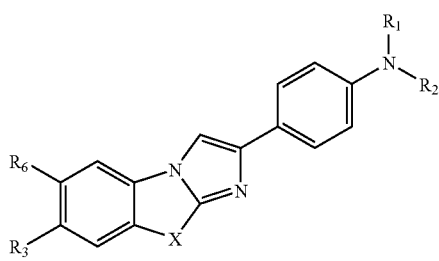 | $R_1$ is $CnH_2n + 1$, (E)-$CH_2CH$=CH—I or (Z)-$CH_2CH$=CH—I, $R_2$ is $CnH_2n + 1$, $R_3$ is $CnH_2n + 1$, F, Cl, Br, I, $NR_1$ or $OR_1$, $R_6$ is $CnH_2n + 1$, F, Cl, Br, I or $OR_1$ and X is O or S, where $R_1$ is $CnH_2n + 1$, (E)-$CH_2CH$=CH—I or (Z)-$CH_2CH$=CH—I and n is 0, 1, 2, 3, 4 or 5 |
| 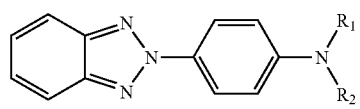 | $R_1$ is $CnH_2n + 1$, (E)-$CH_2CH$=CH—I or (Z)-$CH_2CH$=CH—I and $R_2$ is $CnH_2n + 1$, where n is 0, 1, 2, 3, 4 or 5 |
| 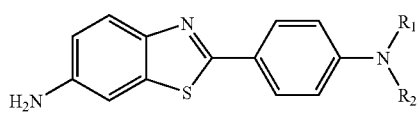 | $R_1$ is $CnH_2n + 1$, (E)-$CH_2CH$=CH—I or (Z)-$CH_2CH$=CH—I and $R_2$ is $CnH_2n + 1$, where n is 0, 1, 2, 3, 4 or 5 |
| 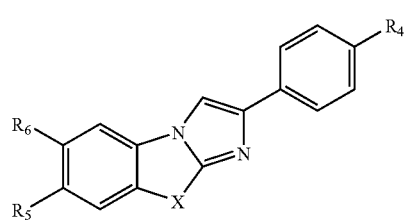 | $R_4$ is F, Cl, Br, I or $OR_1$, $R_5$ is H, $OR_1$ or $NR_1R_2$, $R_6$ is H, $OR_1$ or $NR_1R_2$ and X is O or S, where $R_1$ is $CnH_2n + 1$, (E)-$CH_2CH$=CH—I or (Z)-$CH_2CH$=CH—I, $R_2$ is $CnH_2n + 1$ and n is 0, 1, 2, 3, 4 or 5 |

TABLE 1-continued

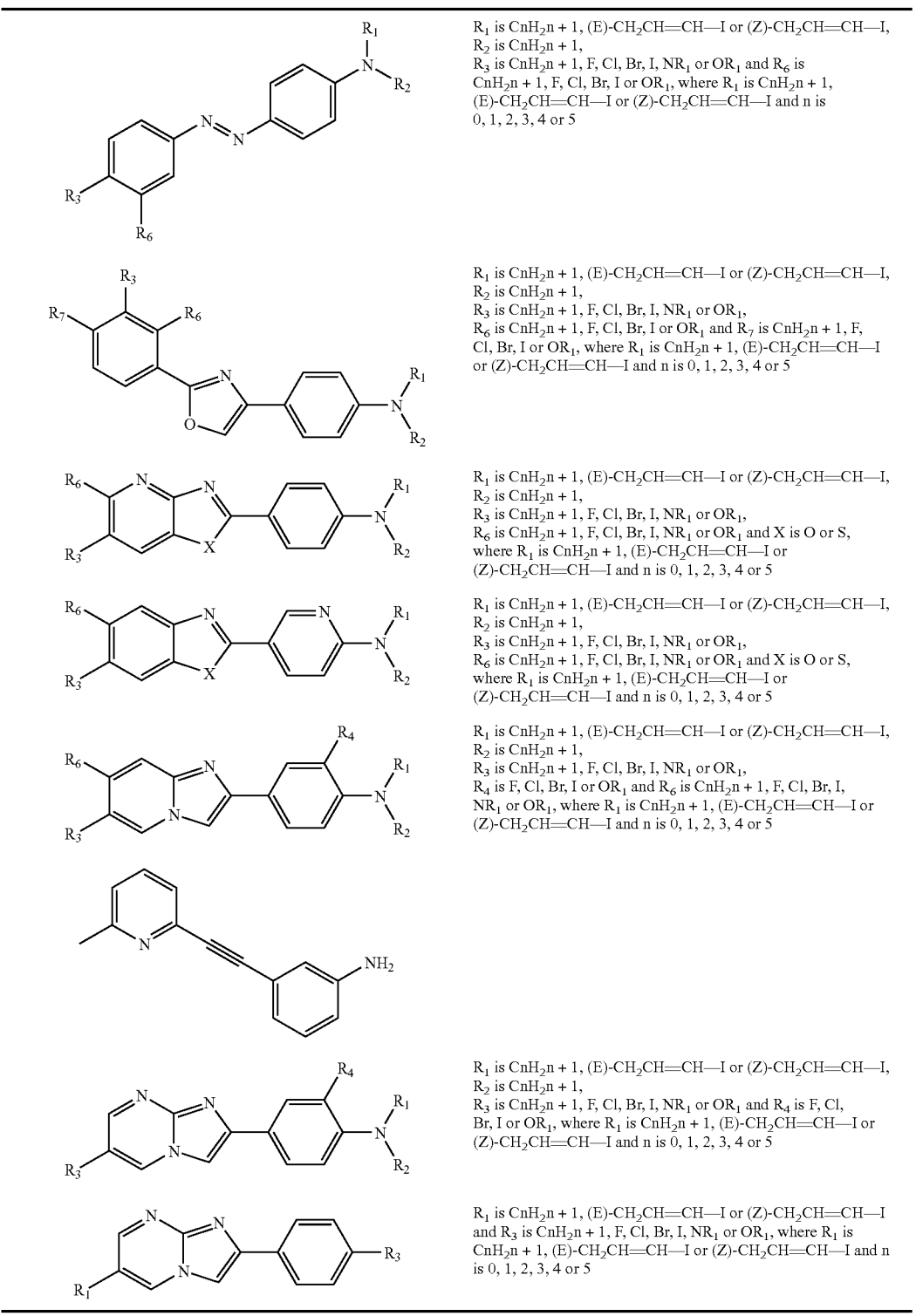

| Structure | Substituents |
|---|---|
| (azo compound with R1, R2, R3, R6) | $R_1$ is $C_nH_{2n+1}$, (E)-$CH_2CH=CH-I$ or (Z)-$CH_2CH=CH-I$, $R_2$ is $C_nH_{2n+1}$, $R_3$ is $C_nH_{2n+1}$, F, Cl, Br, I, $NR_1$ or $OR_1$ and $R_6$ is $C_nH_{2n+1}$, F, Cl, Br, I or $OR_1$, where $R_1$ is $C_nH_{2n+1}$, (E)-$CH_2CH=CH-I$ or (Z)-$CH_2CH=CH-I$ and n is 0, 1, 2, 3, 4 or 5 |
| (oxazole with R3, R6, R7) | $R_1$ is $C_nH_{2n+1}$, (E)-$CH_2CH=CH-I$ or (Z)-$CH_2CH=CH-I$, $R_2$ is $C_nH_{2n+1}$, $R_3$ is $C_nH_{2n+1}$, F, Cl, Br, I, $NR_1$ or $OR_1$, $R_6$ is $C_nH_{2n+1}$, F, Cl, Br, I or $OR_1$ and $R_7$ is $C_nH_{2n+1}$, F, Cl, Br, I or $OR_1$, where $R_1$ is $C_nH_{2n+1}$, (E)-$CH_2CH=CH-I$ or (Z)-$CH_2CH=CH-I$ and n is 0, 1, 2, 3, 4 or 5 |
| (benzoxazole/thiazole, X = O or S) | $R_1$ is $C_nH_{2n+1}$, (E)-$CH_2CH=CH-I$ or (Z)-$CH_2CH=CH-I$, $R_2$ is $C_nH_{2n+1}$, $R_3$ is $C_nH_{2n+1}$, F, Cl, Br, I, $NR_1$ or $OR_1$, $R_6$ is $C_nH_{2n+1}$, F, Cl, Br, I, $NR_1$ or $OR_1$ and X is O or S, where $R_1$ is $C_nH_{2n+1}$, (E)-$CH_2CH=CH-I$ or (Z)-$CH_2CH=CH-I$ and n is 0, 1, 2, 3, 4 or 5 |
| (benzoxazole with pyridine, X = O or S) | $R_1$ is $C_nH_{2n+1}$, (E)-$CH_2CH=CH-I$ or (Z)-$CH_2CH=CH-I$, $R_2$ is $C_nH_{2n+1}$, $R_3$ is $C_nH_{2n+1}$, F, Cl, Br, I, $NR_1$ or $OR_1$, $R_6$ is $C_nH_{2n+1}$, F, Cl, Br, I, $NR_1$ or $OR_1$ and X is O or S, where $R_1$ is $C_nH_{2n+1}$, (E)-$CH_2CH=CH-I$ or (Z)-$CH_2CH=CH-I$ and n is 0, 1, 2, 3, 4 or 5 |
| (imidazopyridine with R3, R4, R6) | $R_1$ is $C_nH_{2n+1}$, (E)-$CH_2CH=CH-I$ or (Z)-$CH_2CH=CH-I$, $R_2$ is $C_nH_{2n+1}$, $R_3$ is $C_nH_{2n+1}$, F, Cl, Br, I, $NR_1$ or $OR_1$, $R_4$ is F, Cl, Br, I or $OR_1$ and $R_6$ is $C_nH_{2n+1}$, F, Cl, Br, I, $NR_1$ or $OR_1$, where $R_1$ is $C_nH_{2n+1}$, (E)-$CH_2CH=CH-I$ or (Z)-$CH_2CH=CH-I$ and n is 0, 1, 2, 3, 4 or 5 |
| (methylpyridine-alkyne-aniline) | |
| (imidazopyrimidine with R3, R4) | $R_1$ is $C_nH_{2n+1}$, (E)-$CH_2CH=CH-I$ or (Z)-$CH_2CH=CH-I$, $R_2$ is $C_nH_{2n+1}$, $R_3$ is $C_nH_{2n+1}$, F, Cl, Br, I, $NR_1$ or $OR_1$ and $R_4$ is F, Cl, Br, I or $OR_1$, where $R_1$ is $C_nH_{2n+1}$, (E)-$CH_2CH=CH-I$ or (Z)-$CH_2CH=CH-I$ and n is 0, 1, 2, 3, 4 or 5 |
| (imidazopyrimidine with R1, R3) | $R_1$ is $C_nH_{2n+1}$, (E)-$CH_2CH=CH-I$ or (Z)-$CH_2CH=CH-I$ and $R_3$ is $C_nH_{2n+1}$, F, Cl, Br, I, $NR_1$ or $OR_1$, where $R_1$ is $C_nH_{2n+1}$, (E)-$CH_2CH=CH-I$ or (Z)-$CH_2CH=CH-I$ and n is 0, 1, 2, 3, 4 or 5 |

Preferably, an amyloid probe of one or more of the compounds of Table 1 can comprise one or more substituents as a radiolabel (marker or tag). For example, the label can replace any substituent of a compound of the invention or be provided as an additional substituent. An amyloid probe of one or more of the compounds of Table 1 can comprise one or more of $^{131}I$, $^{124}I$, $^{125}I$, $^{3}H$, $^{123}I$, $^{18}F$, $^{19}F$, $^{11}C$, $^{75}Br$, $^{13}C$, $^{13}N$, $^{15}O$, $^{76}Br$, $CH_2-CH_2$-label, $O-CH_2-CH_2$-label, $CH_2-CH_2-CH_2$-label, $O-CH_2-CH_2-CH_2$-label, $-[OCH_2-CH_2]_n$-label, $O-CH_2-CH=CH$-label ((E) or (Z) configuration), $N-CH_2-CH=CH$-label ((E) or (Z) configuration) in which "label" can independently be $^{131}I$, $^{124}I$, $^{125}I$, $^{3}H$, $^{123}I$, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C or can be a label (mark or tag) as a substituent of a lower alkyl group, $(CH_2)_nOR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or CR$_2$—CR$_2$-aryl in which L can be a halogen (for example, $^{13}$CH$_2$—CH$_2$—F) and R can be H, F, Cl, Br, I or a lower alkyl group.

In another aspect, the compound or amyloid probe of the structure or formula

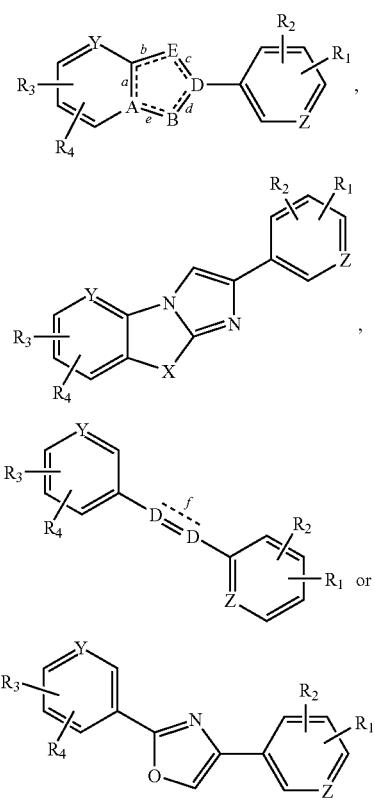

as well as a compound or amyloid probe of Table 1 can comprise any one of the compounds of Table 2 or an amyloid probe thereof comprising a label (for example, $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O or $^{76}$Br). Similarly, a compound or probe of the invention can comprise one or more of the exemplary structures or formulas of Table 2.

TABLE 2

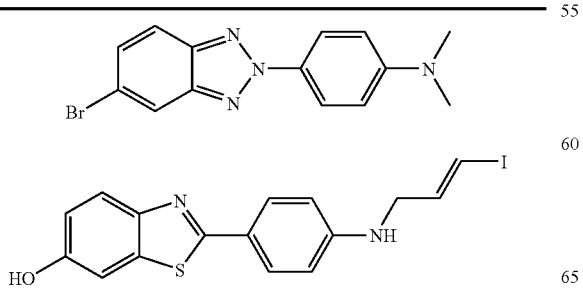

TABLE 2-continued

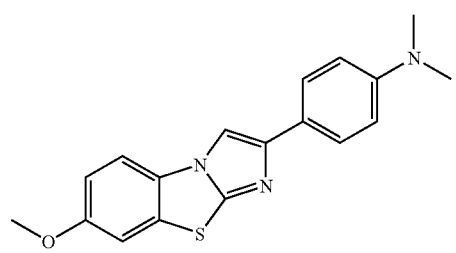

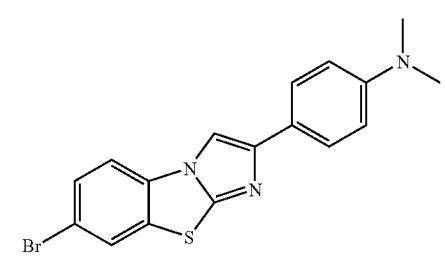

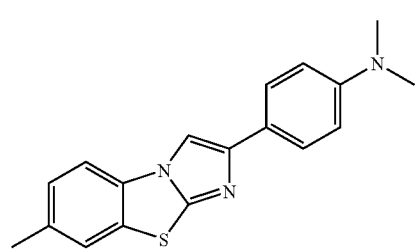

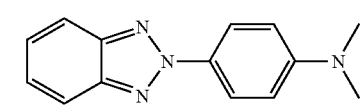

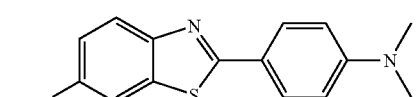

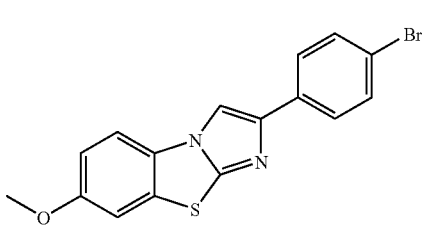

TABLE 2-continued
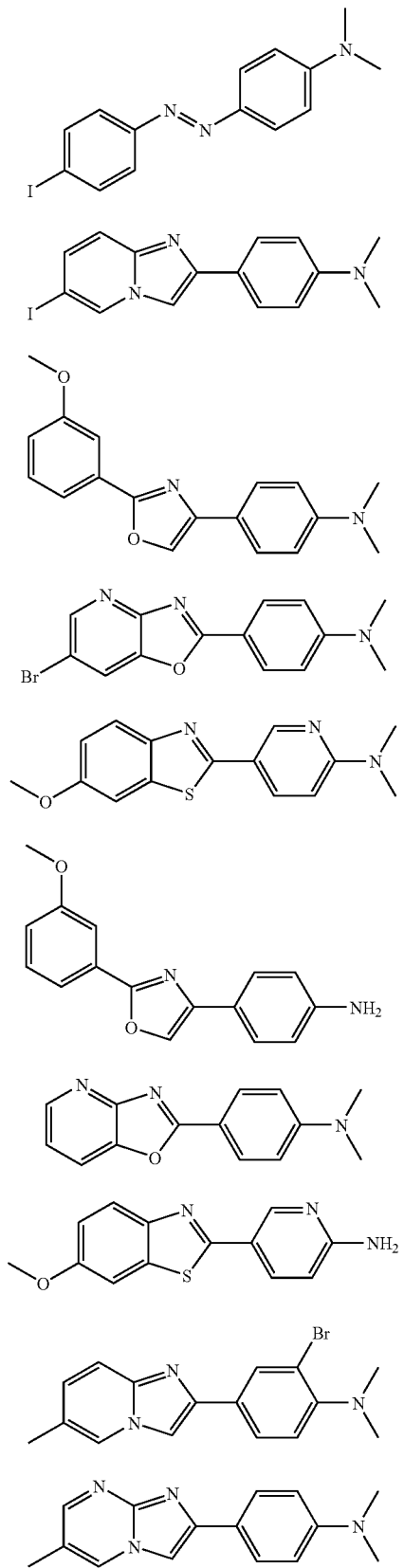
TABLE 2-continued
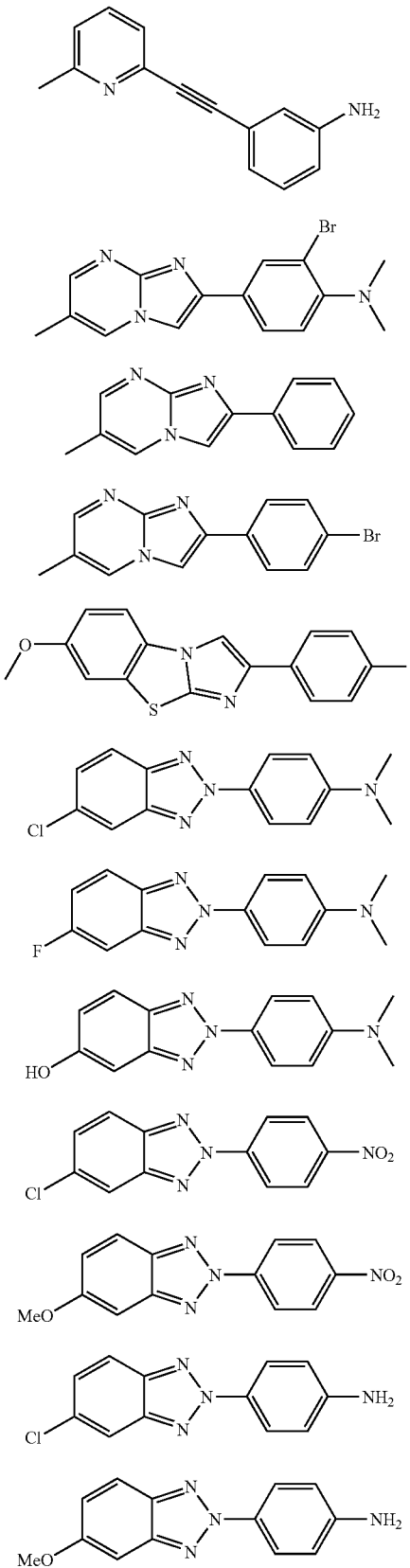

TABLE 2-continued

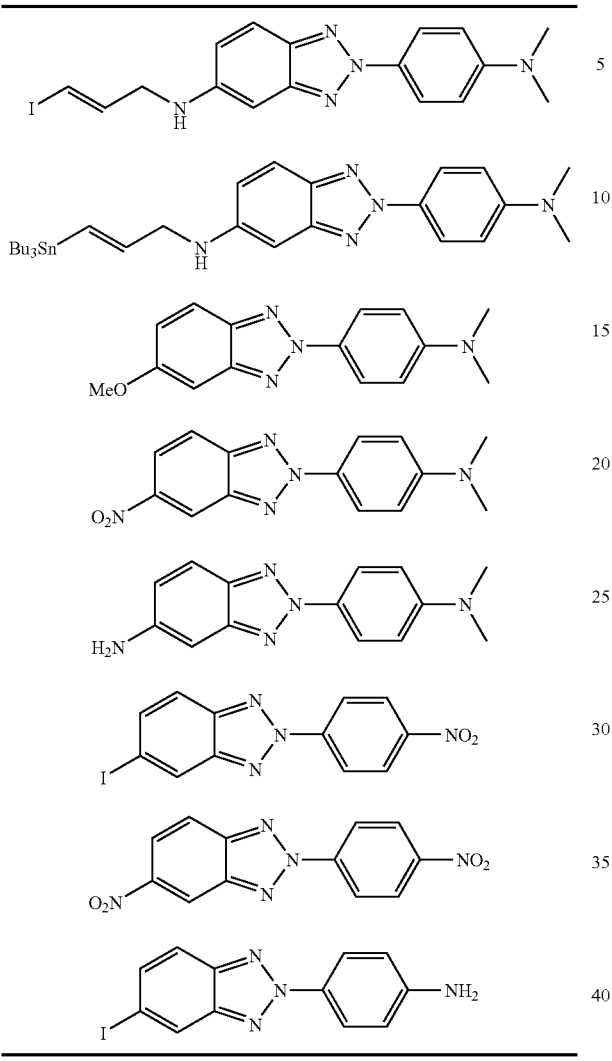

In one aspect, an amyloid probe of the invention can comprise one or more of the exemplary structures or formulas of Table 3. A probe comprising the structures or formulas of Table 3 can also be provided from a compound of Table 1 or any one of the compounds of Table 2. For example, an amyloid probe of the structure or formula

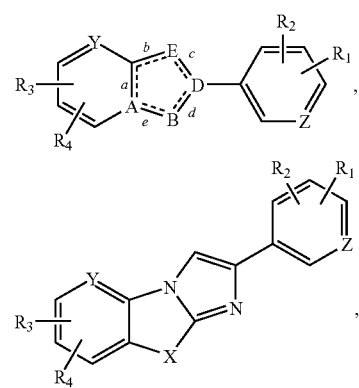

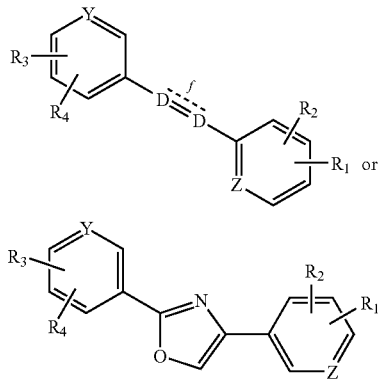

can comprise one or more substituents as a label (marker or tag). Exemplary labels include radionuclides, radioisotopes or isotopes. For example, $R_1$, $R_2$, $R_3$, $R_4$, $R_5$ and $R_6$, each of which can independently comprise (for example, $R_1$ can be $^{131}$I or $CH_2$—$CH_2$—$^{131}$I) $^{131}$I, $^{124}$I, $^{125}$I, $^{3}$H, $^{123}$I, $^{18}$I, $^{19}$F, $^{11}$C, $^{75}$Br, $^{13}$C, $^{13}$N, $^{15}$O, $^{76}$Br, $CH_2$—$CH_2$-label, O—$CH_2$—$CH_2$-label, $CH_2$—$CH_2$—$CH_2$-label, O—$CH_2$—$CH_2$—$CH_2$-label, —[$OCH_2$—$CH_2$]$_n$-label, O—$CH_2$—CH=CH-label ((E) or (Z) configuration), N—$CH_2$—CH=CH-label ((E) or (Z) configuration) in which "label" can independently be $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C can be a label (mark or tag) as a substituent of a lower alkyl group, $(CH_2)_n$OR, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

TABLE 3

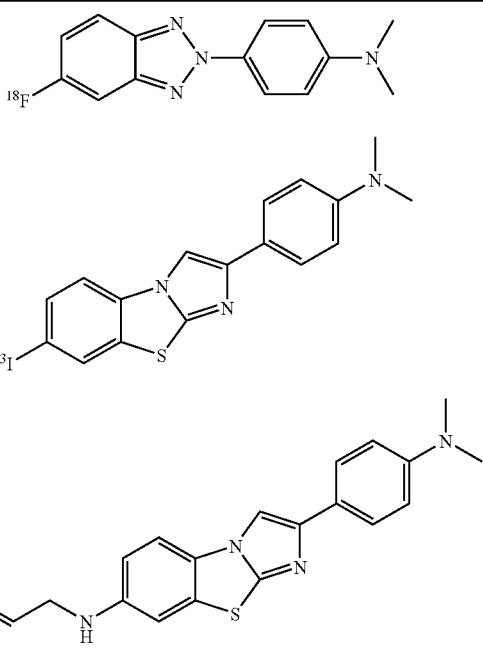

TABLE 3-continued
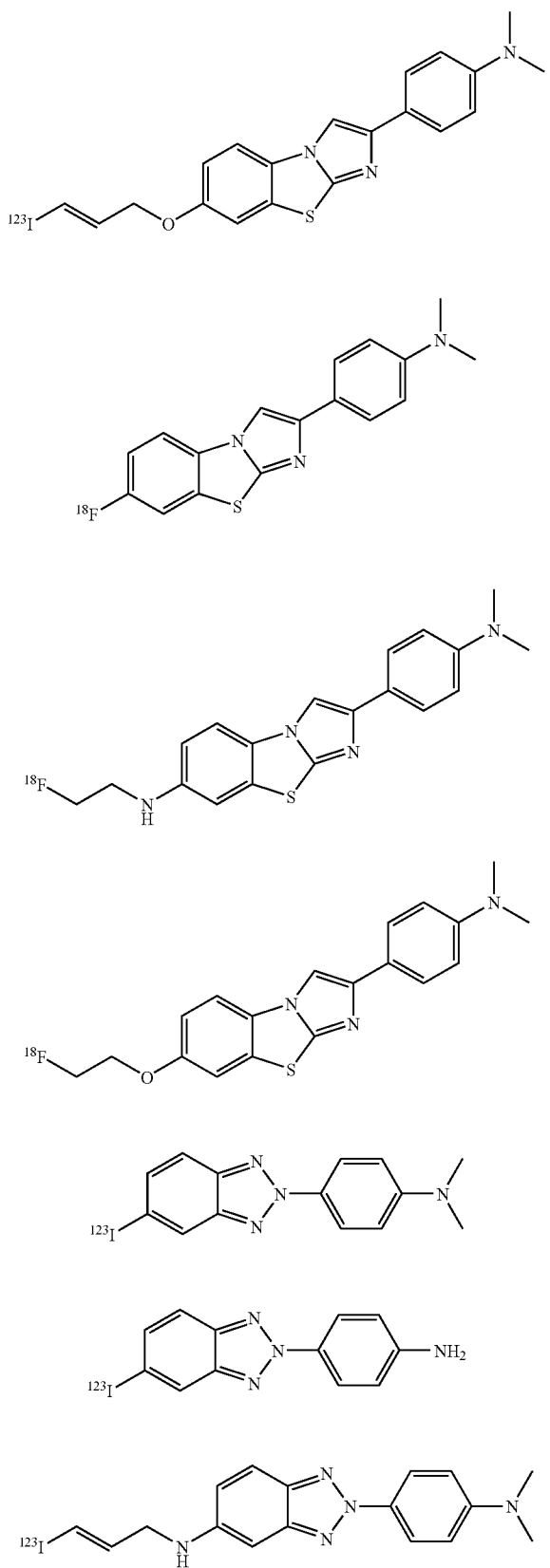
TABLE 3-continued
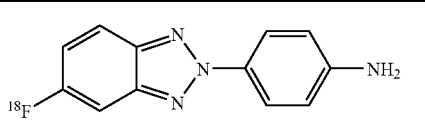
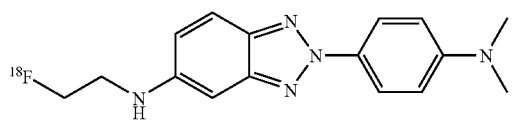
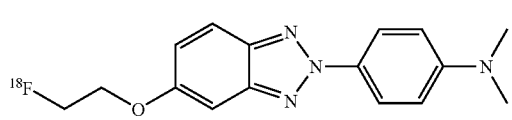
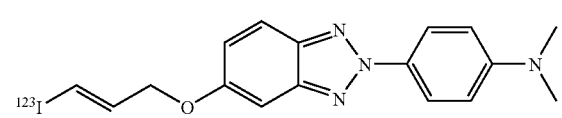
In one aspect, an amyloid probe of the invention can comprise one or more of the exemplary structures or formulas of Table 4. A probe of the structure or formula
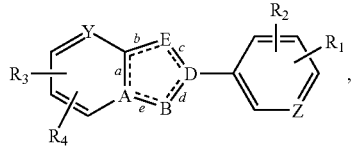
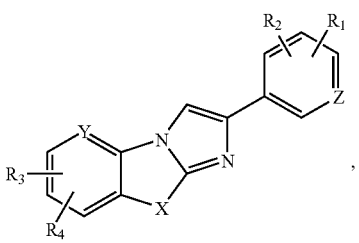
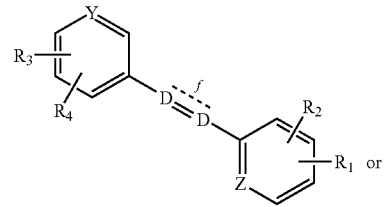
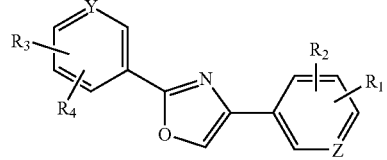
comprising one or more substituents as a label, marker or tag (for example, a radionuclide, radioisotope or isotope) can also comprise a probe of Table 4.

TABLE 4

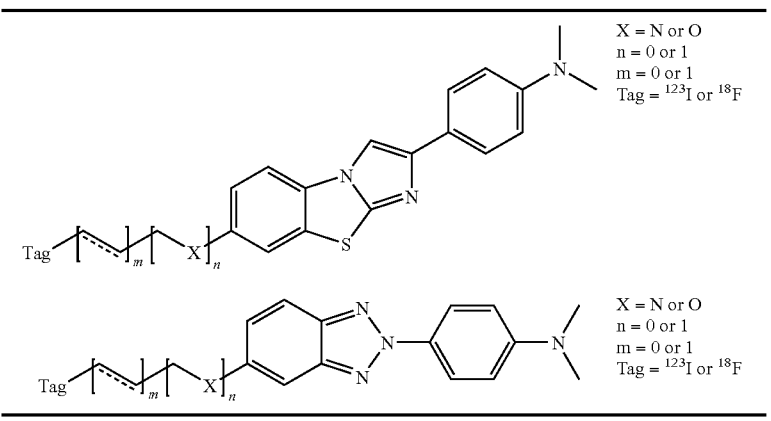

X = N or O
n = 0 or 1
m = 0 or 1
Tag = $^{123}$I or $^{18}$F

X = N or O
n = 0 or 1
m = 0 or 1
Tag = $^{123}$I or $^{18}$F

The invention also relates to an in vivo method for detecting amyloid deposits in a subject. For example, the method can comprise administering a detectable quantity (effective amount) of a labeled compound of the invention and detecting the binding of the compound to an amyloid deposit in the subject. In one aspect, the amyloid deposit is located in the brain of a subject. The subject can be suffering from or suspected of suffering from a disease associated with amyloid deposits or amyloidosis such as, for example, AD, familial AD, homozygotes for the apolipoprotein E4 allele or Down's syndrome.

In one aspect, detection can be performed via a scintigraphic approach. For example, detection accomplished by gamma imaging, magnetic resonance imaging, magnetic resonance spectroscopy and/or fluorescence spectroscopy. Preferably, the scintigraphic approach for detecting an amyloid probe of the invention comprises either PET or SPECT imaging and standard protocols used in conjunction therewith. The compound or amyloid probe of the invention can also be administered as a pharmaceutical composition. Exemplary pharmaceutical compositions comprise a compound or amyloid probe of the invention and a pharmaceutically acceptable carrier. Preferably, administering a compound or probe of the invention to a subject in need thereof can be by intravenous injection or bolus intravenous injection. Other exemplary routes of administration can include oral, rectal, parenteral (intramuscular or subcutaneous), intracisternal, intravaginal, intraperitoneal, local (powders, ointments or drops) or as a buccal or nasal spray as well as ocular drops.

A method of the invention can also comprise determining a ratio (for example, an amyloid deposit uptake ratio). In one aspect, the ratio can be that of the radioactive uptake of a compound or probe of the invention to a brain area other than the cerebellum as compared to the radioactive uptake of the compound or probe to the cerebellum. The method can comprise comparing the ratio from a subject suffering from or thought to be at risk for a disease associated with associated with amyloid deposits or amyloidosis to that of a healthy (non-diseased) subject. In another aspect, the invention relates to a method of inhibiting cell degeneration and toxicity associated with fibril formation in an amyloidosis associated disease or malady. For example, the method comprises administering to a subject having, suspected of having and/or at risk for a disease or malady associated with amyloid deposits or amyloidosis, a compound or amyloid probe of the invention in an effective amount.

A method of the invention relates to inhibiting cell degeneration and toxicity associated with fibril formation in an amyloidosis associated disease or malady. Preferably, the method comprises administering to a subject in need thereof a compound or amyloid probe of the invention (or analogs, salts, pharmaceutical compositions, derivatives, prodrugs or racemic mixtures thereof) in an effective amount, for example, an amount capable inhibiting cell degeneration and toxicity associated with fibril formation in an amyloidosis associated disease or malady. Examples of amyloidosis associated diseases or maladies include, but are not limited to, AD, familial AD, homozygotes for the apolipoprotein E4 allele, glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease and Islets of Langerhans diabetes Type II insulinoma.

In one aspect, the invention relates to a method for detecting amyloid deposits in biopsy or post-mortem subject tissue (in vitro). The method comprises incubating formalin-fixed tissue with a solution of a compound or probe of the invention to allow for binding with the deposit or formation of a labeled deposit and detecting the compound, probe or labeled deposit. The solution can be composed of 25 to 100% ethanol (with the remainder being water) saturated with the compound or amyloid probe of the invention. Preferably, in vitro detection can be accomplished by microscopic techniques. Examples of microscopic techniques include bright field, fluorescence, laser confocal or cross-polarization microscopy.

The invention also relates to a method of distinguishing an AD brain or a brain having amyloid deposits (plaques) from a normal brain comprising incubating (separately) homogenates of weighed tissue from the cerebellum and another area of the same brain other than the cerebellum, from a subject suspected of having AD or amyloid deposits, with a compound or probe of the invention so that binding with amyloid in the tissues occurs. The method also comprises quantifying the amount of amyloid bound to the compound or probe by separating the tissue-bound from the tissue-unbound, quantifying the tissue-bound and converting the units of tissue-bound (labeled deposit) to units of micrograms of amyloid per 100 mg of tissue by comparison with a standard. The method can also comprise calculating a ratio of the amount of amyloid in the area of the brain other than the cerebellum to the amount of amyloid in the cerebellum and comparing the ratio of the amount of amyloid in tissue from the subject suspected of having AD or amyloid deposits with ratios for the amount of amyloid in the tissue from normal subjects. In one aspect, the method comprises determining the presence of AD or amyloid deposits if the ratio from the brain of a subject suspected of having AD or amyloid deposits is above about 40%, 50%, 60%, 70%, 80% or 90% (preferably, for example, above 50% and, more preferably, for example, above 90%) of the ratios obtained from the brains of normal subjects.

The invention also relates to methods for preparing compounds of the invention. In one aspect, one or more of the compounds can be modified to be an amyloid probe of the invention. The amyloid probes of the invention are particularly useful for the in vivo diagnosis and/or study of the progression or regression of disease states or maladies in a patient. Exemplary disease states or maladies include, for example, AD, familial AD, homozygotes for the apolipoprotein E4 allele, glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease and Islets of Langerhans diabetes Type II insulinoma. An amyloid probe may also comprise one or more compounds of the invention and at least one detectable marker, tag or label such as, for example, a radionuclide, radioisotope or isotope. The selection of detectable markers, tags or labels for an amyloid probe of the invention can vary depending on the particular modality chosen for in vivo imaging, the disease state or malady being diagnoses or studied or the route of administration of the probe.

The invention relates to an in vivo or in vitro method for detecting in a subject one or more amyloid deposits. In one aspect, the amyloid deposit can comprise one or more amyloid or amyloidogenic protein. The method comprises administering to a subject suffering from a disease associated with amyloidosis, a detectable quantity (effective amount) of a compound or amyloid probe of the invention (or analogs, salts, pharmaceutical compositions, derivatives, prodrugs or racemic mixtures thereof). For example, an amyloid probe of the invention can comprise one or more substituents as a label (radiolabel, marker or tag). Preferably, an amyloid probe of the invention comprises one or more radionuclides, radioisotopes or isotopes (labels). Examples of radiolabels for an amyloid probe of the invention include, but are not limited to, $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O, $^{76}$Br. The method also comprises detecting the binding of the compound or probe to an amyloid deposit (plaque). An amyloid deposit can comprise amyloid or amyloidogenic proteins (or precursors, portions, fragments and peptides thereof). Examples of precursor and amyloidogenic proteins as well as amyloidosis-related diseases are generally described in International Publication No. WO 2007/035405, which is incorporated by reference herein.

Moreover, the invention relates to an in vivo method for detecting at least one amyloid deposit. For example, the method can comprise administering to a subject suffering from or thought to be at risk of suffering from a disease associated with amyloidosis, a detectable quantity (effective amount) of a compound or probe of the invention (or analogs, salts, pharmaceutical compositions, derivatives, prodrugs or racemic mixtures thereof). In one aspect, the compound or amyloid probe binds to the amyloid deposit. The method also comprises irradiating the subject and collecting imaging data emitted by the compound or amyloid probe. Optionally, the method comprises processing the imaging data in order to diagnose and/or study of the progression or regression (when accompanied by a therapy protocol) of disease states or maladies in a subject.

The invention also relates to the use of a compound or probe of the invention for detecting amyloid deposits in a subject suffering from a disease associated with amyloidosis. The invention further relates to the use of a compound or amyloid probe of the invention in the preparation of a medicament for use in the detection of amyloid deposits in a subject. In one aspect, one or more amyloid deposits are located in the brain. For example, a subject can be suffering from amyloidosis characterized by amyloid deposits (plaques) in the regions of the brain. Other organs or tissues that can comprise amyloid deposits and are able to be studied, detected or imaged using the compounds or probes of the invention as well as methods, kits, assays or uses thereof include, for example, mesodermal tissue, tenosynovium, joints, aortic, thyroid, islets of Langerhans, aging pituitary, latrogenic, cardiac atria, cornea, lens, vitreous humor, retina, sclera, pancreas and parenchymatous organ. Preferably, a compound or amyloid probe of the invention can be detected via approaches that include gamma imaging, magnetic resonance imaging, magnetic resonance spectroscopy or fluorescence spectroscopy.

In one aspect, the invention relates to a method of diagnosing an amyloidosis-related disease or a neurodegenerative disease such as, for example, AD. Preferably, the method comprises contacting an ocular tissue with a labeled compound of the invention (probe), which binds to an amyloid deposit and/or amyloid protein or precursor, portion, fragment or peptide thereof and/or one or more Aβ and/or amyloidogenic proteins as well as any receptors of the same in the ocular tissue. The method also comprises optionally allowing the compound to distribute into the lens and then imaging the ocular tissue. For example, the labeled compound can comprises an amyloid probe of the invention and an increase in binding of the probe to the ocular tissue compared to a normal control level of binding indicates that the mammal is suffering from or is at risk of developing an amyloidosis-related disease or a neurodegenerative disease (for example, AD). A compound or probe of the invention can be administered in an effective amount to a subject, for example, as ocular drops.

In another aspect, the invention provides a method for prognosis of an amyloidosis-related disease or a neurodegenerative disease such as, for example, AD. For example, the method can comprise contacting ocular tissue of a mammal with a compound or probe, which binds to an amyloid deposit and/or amyloid protein or precursor, portion, fragment or peptide thereof and/or one or more Aβ and/or amyloidogenic proteins as well as any receptors of the same. The method can also optionally comprise allowing the compound or probe to distribute into the lens and imaging the ocular tissue. Preferably, the method comprises quantitating the level of association of the compound or probe with the ocular tissue and comparing the level of association with a normal control level of association, where increasing levels of association over time indicates an adverse prognosis. The methods of the invention also contemplate administering a compound or probe of the invention to a subject as ocular drops.

The invention also relates to a method for diagnosing an amyloidosis-related disease or a predisposition thereto in a mammal. The method comprises detection of an amyloid deposit and/or amyloid proteins or precursors, portions, fragments or peptides thereof (including Aβ precursor proteins, Aβ, Aβ$_{1-42}$, prion proteins and α-synuclein) and/or one or more Aβ and/or amyloidogenic proteins with a labeled compound or probe in a supranuclear or deep cortical region of an ocular lens. For example, the method comprises comparing an amount of the "amyloid" compared to a normal control value and an increase indicates that the subject is suffering from or is at risk of developing an amyloidosis-related disease. In one aspect, detection can be by quasi-elastic light scattering or spectroscopic techniques (for example, Raman), although radioscintigraphy, magnetic resonance imaging (MRI), assays, chemilumensence, near infrared luminescence, fluorescence, gamma imaging, magnetic resonance imaging, magnetic resonance spectroscopy, fluorescence spectroscopy, SPECT, computed tomography (CT scan) and/or positron emission tomography (PET) can also be used.

In one aspect, a method of diagnosing an amyloidosis-related disease or a predisposition thereto in a mammal can comprise illuminating the subject's lens tissue with an excitation light beam and detecting scattered light emitted from the tissue (for example, to detect a compound or probe of the invention. Exemplary protocols, means, devices, apparatuses or systems for studying or diagnosing amyloidosis-related diseases, particularly, those associated with detecting amyloid deposits and/or amyloid proteins or precursors, portions, fragments or peptides thereof (including Aβ precursor proteins, Aβ, Aβ$_{1-42}$, prion proteins and α-synuclein) and/or one or more Aβ and/or amyloidogenic proteins with a labeled compound or probe in a supranuclear, deep cortical region of an ocular lens and/or ocular tissues are generally described in U.S. Pat. Nos. 7,107,092 and 6,849,249, both of which are incorporated by reference herein.

DESCRIPTION OF THE DRAWINGS

Other features and advantages of the invention may also be apparent from the following detailed description thereof, taken in conjunction with the accompanying drawings, which may depict preferred aspects by way of example, not by way of limitations.

DETAILED DESCRIPTION OF THE INVENTION

Figure 1:
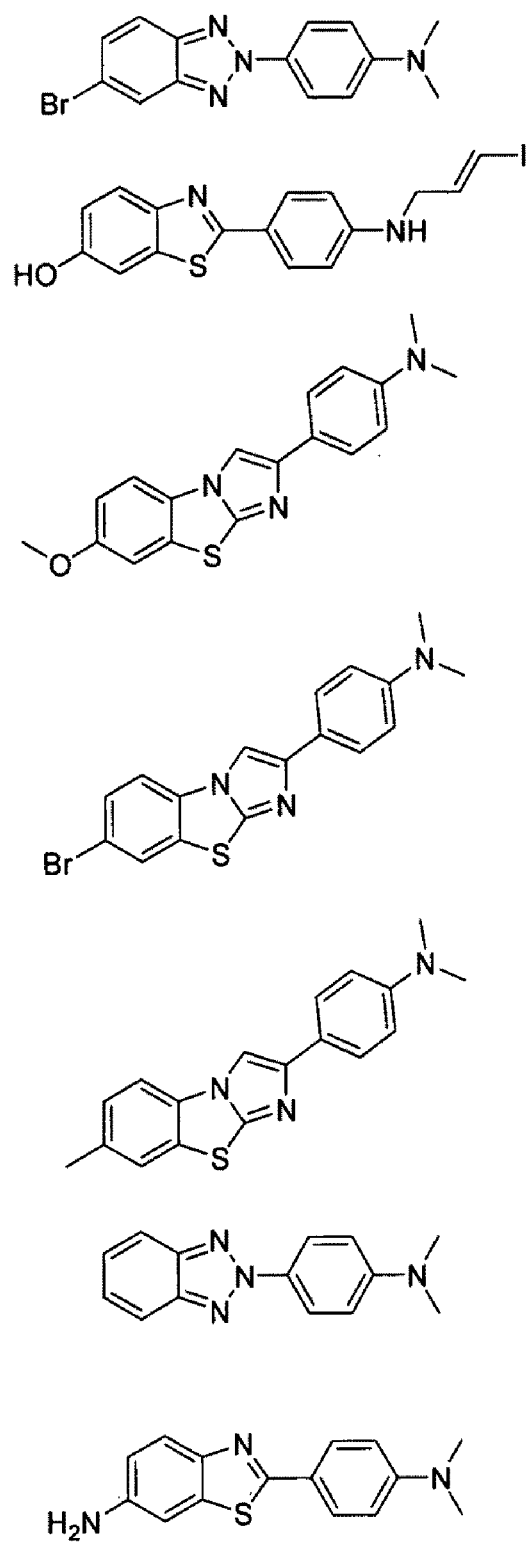
FIG. 1 includes exemplary structures for compounds of the invention, which can be modified to comprise one or more amyloid probes that can be useful for in vivo imaging of amyloid and/or amyloid deposits.

The present invention provides compounds and amyloid probes thereof comprising detectable markers for antemortem in vivo imaging of amyloid deposits such as, for example, amyloid plaques. In one aspect, the compounds and amyloid probes of the invention are amyloid binding compounds. The amyloid probes of the invention can be used in vivo to diagnosis and study the progression or regression of disease states or maladies that include, for example, AD, Down's syndrome, familial AD, glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler-Scheinker syndrome, medullary carcinoma of the thyroid, Isolated atrial amyloid, β-microglobulin amyloid in dialysis patients, inclusion body myositis, β$_2$-amyloid deposits in muscle wasting disease and Islets of Langerhans diabetes Type II insulinoma and homozygotes for the apolipoprotein E4 allele.

In one aspect, the invention relates to a compound or amyloid probe thereof comprising the structure or formula

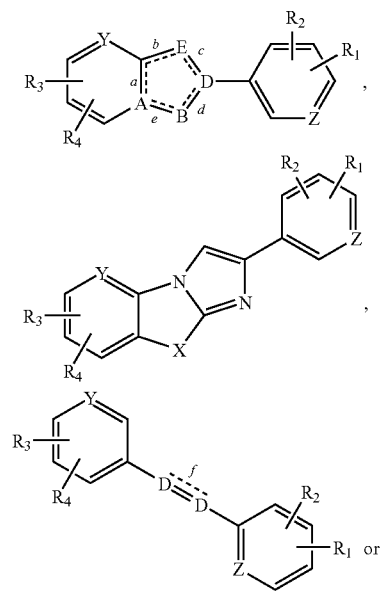

-continued

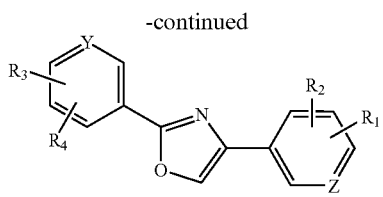

in which $R_1$, $R_2$, $R_3$ and $R_4$ are the same or different and can independently be H, F, Cl, Br, I, $NO_2$, CN, $CF_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, $OR_6$, $NR_5R_6$ or $R_6$, $R_5$ can be $C_nH_{2n+1}$ or —$CH_2$—CH=CH-halo ((E) or (Z) configuration in which halo can be any halogen) and $R_6$ can be $C_nH_{2n+1}$, —$[CH_2-CH_2-O]_m$—$R_5$, where n and m can each independently be 0, 1, 2, 3, 4, 5, 6 or 7, A and D can each independently be N or C, E, Y and Z can each independently be CH or N, B can be S, O, N or CH and a, b, c, d, e and f each independently represent an optional bond, provided that when A and E are N, then B can be CH, D can be C and b and d can each be a bond (to provide double bonds), or provided that when B, D and E are N, then A can be C, b and e can each be a bond (to provide double bonds), or provided that when E is N and B is O or S, then A and D can be C, a and c can each be a bond (to provide double bonds), or further provided that when D is C, then f can be a bond (to provide a triple bond of C≡C) or when D is N, then f is not a bond (to provide a double bond of N=N), and detecting the binding of the compound or amyloid probe thereof to an amyloid deposit comprising one or more amyloid or amyloidogenic proteins. For example, an amyloid probe used in conjunction with a method of the invention can comprise one or more substituents as a radiolabel (marker or tag). Preferably, an amyloid probe of the invention comprises one or more of $R_1$, $R_2$, $R_3$, $R_4$, $R_5$ and $R_6$, each of which can independently comprise (for example, $R_1$ can be $^{131}$I or $CH_2$—$CH_2$—$^{131}$I) $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $CH_2$—$CH_2$-label, O—$CH_2$—$CH_2$-label, $CH_2$—$CH_2$—$CH_2$-label, O—$CH_2$—$CH_2$—$CH_2$-label, —$[OCH_2-CH_2]_n$-label, O—$CH_2$—CH=CH-label ((E) or (Z) configuration), N—$CH_2$—CH=CH-label ((E) or (Z) configuration) in which "label" can independently be $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C can be a label (mark or tag) as a substituent of a lower alkyl group, $(CH_2)_nOR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

The in vivo methods of the invention can be performed on a subject having, suspected of having or at risk for an amyloidosis-related disease or a disease or malady associated with amyloid deposits and/or amyloidosis. An amyloid probe of the invention can comprise a label (marker or tag) that includes, for example, radionuclides, radioisotopes or isotopes. For example, a label can replace any substituent of a compound of the invention or be provided as an additional substituent for an amyloid probe. In one aspect, an amyloid probe of a compound of the invention can also comprise one or more of $^{131}$I, $^{124}$I, $^{125}$I, $^3$H, $^{123}$I, $^{18}$I, $^{19}$F, $^{11}$C, $^{75}$Br, $^{13}$C, $^{13}$N, $^{15}$O, $^{76}$Br, $CH_2$—$CH_2$-label, O—$CH_2$—$CH_2$-label, $CH_2$—$CH_2$—$CH_2$-label, O—$CH_2$—$CH_2$—$CH_2$-label, —$[OCH_2-CH_2]_n$-label, O—$CH_2$—CH=CH-label ((E) or (Z) configuration), N—$CH_2$—CH=CH-label ((E) or (Z) configuration) in which "label" can independently be $^{131}$I, $^{124}$I, $^{125}$I, $^3$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C can be a label (mark or tag) as a substituent of a lower alkyl group, $(CH_2)_nOR$, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group.

The invention also relates to compounds or amyloid probes that can be characterized as amyloid binding compounds (including analogs, salts, pharmaceutical compositions, derivatives, prodrugs or racemic mixtures thereof). In one aspect, a compound or amyloid probe of the invention can be a water-soluble, non-toxic salt thereof. Preferably, a compound or probe of the invention binds to amyloid deposits (plaques). For example, a compound or probe of the invention can bind to amyloid (including Aβ) and/or amyloidogenic proteins or precursors, portions, fragments and peptides thereof, which can comprise one or more amyloid deposits or plaques. A compound or amyloid probe of the invention can preferentially bind to amyloid deposits that are present in disease states or maladies characterized by or associated with amyloidosis.

A compound or amyloid probe of the invention can bind to amyloid deposits of amyloid (including Aβ) and/or amyloidogenic proteins with a dissociation constant (for example, an equilibrium dissociation constant, $K_d$) from, for example, about 0.0001 to 10 μM as measured by binding to a synthetic amyloid peptide or AD brain tissue. The invention contemplates measurement of a dissociation constant (for example, $K_d$ and $K_i$) or performing competition, saturation and kinetics experiments by conventional techniques routine to one of ordinary skill in the art. Moreover, a compound or probe of the invention can compete with a reference compound for binding to amyloid deposits with a dissociation constant of inhibition (for example, $K_i$) from, for example, about 0.01 nM to >10,000 nM. For example, a compound of the invention (MNI-187) demonstrated a high-affinity for Aβ based on its IC50 binding value of 0.17 nM as evaluated using human AD brain tissue.

In one aspect, a method of the invention can be used to determine the presence and location of amyloid deposits in an organ or body area, preferably, the brain, of a patient. An exemplary method of the invention comprises administration of a detectable quantity of an amyloid probe to a patient. For example, an amyloid probe may be derived from a compound of the invention such as those having the exemplary structures included in FIGS. 1, 2 and 3 or Tables 1, 2, 3 and 4. An amyloid probe may be administered to a patient as a pharmaceutical composition or a pharmaceutically acceptable salt, preferably, water-soluble, thereof.

"Pharmaceutically acceptable salt" can refer to an acid or base salt of a compound or amyloid probe of the invention, which possesses the desired pharmacological activity and is neither biologically nor otherwise undesirable. Pharmaceutically acceptable salt can also refer to those carboxylate salts or acid addition salts of the compounds or amyloid probes of the invention, which are suitable for use in contact with the tissues of patients without undue toxicity, irritation, allergic response and the like. The salt can refer to the relatively nontoxic, inorganic and organic acid addition salts of compounds or probes of the present invention and may be formed with acids that include, without limitation, acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include, without limitation, ammonium salts, alkali metal salts such as sodium and potassium salts, alkaline earth metal salts such as calcium and magnesium salts, salts with organic bases such as dicyclohexylamine salts, N-methyl-D-glucamine glucamine and salts with amino acids such as arginine and lysine. In various aspects, the basic nitrogen-containing groups can be quaternized with agents including lower alkyl halides such as methyl, ethyl, propyl and butyl chlorides, bromides and iodides, dialkyl sulfates such as dimethyl, diethyl, dibutyl and diamyl sulfates, long chain halides such as decyl, lauryl, myristyl and stearyl chlorides, bromides and iodides and aralkyl halides such as phenethyl bromides. Also included are those salts derived from non-toxic organic acids such as aliphatic mono and dicarboxylic acids, phenyl-substituted alkanoic acids, hydroxy alkanoic and alkanedioic acids, aromatic acids and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate and the like. These may include cations based on the alkali and alkaline earth metals such as sodium, lithium, potassium, calcium, magnesium and the like as well as non-toxic ammonium, quaternary ammonium and amine cations including, but not limited to, ammonium, tetramethylammonium, tetraethylammonium, methylamine, dimethylamine, trimethylamine, triethylamine, ethylamine and the like. Berge S. M., et al., *Pharmaceutical Salts, J. Pharm. Sci.,* 66: 1 (1977).

In one aspect, a compound or amyloid probe of the invention is administered to a patient in an amount or dosage suitable for therapeutic use or in vivo imaging. Generally, a unit dosage comprising a compound or amyloid probe of the invention will vary depending on patient considerations. Such considerations include, for example, age, protocol, condition, sex, extent of disease, contraindications, concomitant therapies and the like. An exemplary unit dosage based on these considerations can also be adjusted or modified by a physician skilled in the art. For example, a unit dosage for a patient comprising an amyloid probe can vary from $1 \times 10^{-15}$ g/kg to 10 g/kg, preferably, $1 \times 10^{-15}$ g/kg to 1.0 g/kg. Moreover, a unit dosage comprising an amyloid probe can also be from 1 µCi/kg to 10 mCi/kg and, preferably, 0.1 mCi/kg. Dosage of a compound or probe of the invention can also vary from 0.001 µg/kg to 10 µg/kg or, preferably, from 0.01 µg/kg to 1.0 µg/kg. An effective amount for detection of a compound or probe of the invention administered to a subject as ocular drops can also be adjusted or modified by one skilled in the art. Similarly, an effective amount for therapeutic use of a compound or probe of the invention administered to a subject as ocular drops can also be adjusted or modified by one skilled in the art.

For administration as ocular drops, if a probe of the invention emits light in the range of a normal human lens autofluorescence (blue-green range), the level of autofluorescence is factored into a spectroscopic reading. By way of example, a 10% increase in fluorescence (after probe administration) compared to the level in the absence of the probe (autofluorescence) indicates a pathological state or predisposition to developing an amyloidosis-related disease (for example, AD). Preferably, baseline autofluorescence is established (prior to probe administration) for each subject. A diagnostic level of fluorescence can be at least 25% (preferably, at least 50% and, more preferably, at least 100%) greater than a normal control value. For example, detection of an amyloid probe of the invention via fluorescence spectroscopy, which is 2-fold or more greater than a normal control value, indicates a pathological state. Given that normal human lens tissue autofluorescences in the blue-green range (495 nm-520 nm), the probe can preferably emit a wavelength of light outside the blue-green spectra. In one aspect, the probe can emits a wavelength of light greater than 520 nm (for example, fluorescence in the red, orange-red or infrared range). Alternatively, an amyloid probe of the invention can emit a wavelength less than 450 nm (for example, in the violet or ultraviolet (UV) range). Other protocols, means, devices, apparatuses or systems for studying or diagnosing amyloidosis-related diseases, particularly, those associated with detecting amyloid deposits and/or amyloid proteins or precursors, portions, fragments or peptides thereof (including Aβ precursor proteins, Aβ, Aβ$_{1-42}$, prion proteins and a-synuclein) and/or one or more Aβ and/or amyloidogenic proteins with a labeled compound or probe administered to a subject as ocular drops are generally described in U.S. Pat. Nos. 7,107,092 and 6,849,249, both of which are incorporated by reference herein.

Administration of a compound or amyloid probe of the invention to a subject may be local or systemic and accomplished intravenously, intraarterially, intrathecally (via the spinal fluid) or the like. Administration may also be intradermal or intracavitary, depending upon the body site under examination. In one aspect, after a sufficient time has elapsed for an amyloid probe of the invention to bind with the amyloid, for example, 5 minutes to 48 hours, the area of the subject under investigation is examined by routine imaging techniques or modalities such as magnetic resonance spectroscopy (MRS), magnetic resonance spectroscopy imaging (MRI), positron emission tomography (PET), single-photon emission computed tomography (SPECT), planar scintillation imaging or combinations thereof as well as any emerging imaging modalities. The exact protocol will necessarily vary depending upon factors specific to the patient and depending upon the body site under examination, method of administration and type of amyloid probe or detectable marker used, although the determination of specific procedures would be routine to the skilled artisan.

For brain imaging, preferably, the amount (total or specific uptake) of a bound amyloid probe of the invention (such as a probe that is radioactively labeled with a detectable marker) is measured and compared (as a ratio) with the uptake of a labeled compound of the invention, which may be an amyloid probe, bound to the cerebellum of the patient. This ratio is then compared to the same ratio in one or more age-matched normal brains. Preferably, an amyloid probe of the invention is administered intravenously to a patient in an amount or dosage appropriate for in vivo imaging of amyloid and/or amyloid deposits. The compounds and amyloid probes of the invention can also be administered via a pharmaceutically acceptable carrier. In one aspect, a compound of the invention can be administered for the treatment or prophylaxis of a disease such as AD. For example, a compound of the invention can be included in a composition comprising a pharmaceutically acceptable carrier. An exemplary composition contains human serum albumin and a compound of the invention.

The amyloid probes of the invention can also be administered in the form of injectable compositions, but may also be formulated into well known drug delivery systems such as, for example, oral, rectal, parenteral (intravenous, intramuscular, or subcutaneous), intracisternal, intravaginal, intraperitoneal, local (powders, ointments or drops) or as a buccal or nasal spray as well as ocular drops. As described, administration of a compound or amyloid probe of the invention may also be local or systemic and accomplished intravenously, intraarterially, intrathecally (via the spinal fluid) or the like. A typical composition for administration can comprise a pharmaceutically acceptable carrier for the compound or amyloid probe of the invention. A pharmaceutically acceptable carrier includes such carriers as, for example, aqueous solutions, non-toxic excipients including salts, preservatives, buffers and the like, which are described in Remington's Pharmaceutical Sciences, 15th Ed. Easton: Mack Publishing Co., pp. 1405-1412 and 1461-1487 (1975) and The National Formulary XIV., 14th Ed. Washington: American Pharmaceutical Association (1975).

Exemplary pharmaceutically acceptable carriers for a compound or amyloid probe of the invention can also include non-aqueous solvents such as propylene glycol, polyethylene glycol and vegetable oil or injectable organic esters such as ethyl oleate. An aqueous carrier can also include, without limitation, water, alcoholic/aqueous solutions, saline solutions and parenteral vehicles such as sodium chloride or Ringer's dextrose. Intravenous carriers for administration of a compound or amyloid probe of the invention include, for example, fluid and nutrient replenishers. Preservatives for a compound or amyloid probe of the invention also may include antimicrobial solutions, anti-oxidants, chelating agents and inert gases. The pH and exact concentration of the various components for a pharmaceutical composition can also be adjusted according to routine skills in the art. Goodman and Gilman's The Pharmacological Basis for Therapeutics (7th Edition).

In one aspect, amyloid probes of the invention are those that, in addition to binding (for example, preferentially or specifically) amyloid in vivo and capable of crossing the blood brain barrier, are non-toxic at appropriate dosage levels and have a satisfactory duration of effect. Moreover, a pharmaceutical composition comprising an amyloid probe can be administered to a subject in whom amyloid or amyloid fibril formation is anticipated, for example, patients clinically diagnosed with AD or another disease associated with amyloid deposition. An amyloid probe of a pharmaceutical composition can be derived from a compound of the invention such as those having the exemplary structures included in FIGS. 1, 2 and 3 or Tables 1, 2, 3 and 4.

The invention employs amyloid probes which, in conjunction with noninvasive neuroimaging techniques or modalities such as MRS, MRI, PET or SPECT, are used to quantify amyloid deposition in vivo. The methods of the invention also involve imaging a patient to establish a baseline of amyloid deposition. The term "baseline" can refer to the amount and distribution of a patient's amyloid deposition prior to initiation of an anti-amyloid therapy. An exemplary method of the invention comprises at least one imaging session of a patient following administration of an anti-amyloid therapy. In one aspect, a method of the invention may involve imaging a patient before and after treatment with at least one anti-amyloid or therapeutic agent such as, for example, anti-inflammatory or cholesterol lowering drugs including statins. In vivo imaging may also be performed at any time during the treatment.

Amyloid probes can comprise labeled (marked or tagged) amyloid binding compounds for imaging or detection (for example, identifying, diagnosing, evaluating and/or quantitating in vivo or in vitro) amyloid deposits (plaques) and/or an amyloidosis-related disease state. Amyloid probes can bind (associated or interact) to amyloid deposits including deposits that comprise amyloid proteins or precursors, portions, fragments and peptides thereof and/or one or more Aβ and/or amyloidogenic proteins as well as any receptors of such. Amyloid probes can also bind to amyloid proteins or precursors, portions, fragments and peptides thereof and/or one or more Aβ and/or amyloidogenic proteins as well as any receptors of such. The binding of amyloid probes to amyloid deposits or amyloid proteins or precursors, portions, fragments and peptides thereof and/or one or more Aβ and/or amyloidogenic proteins (as well as any receptors of such) can be of high-affinity and a specific or preferential nature as would be understood by one of ordinary skill in the art and evaluated by conventional techniques related to binding (for example, dissociation constants). The amyloid probes of the invention can include analogs, salts, pharmaceutical compositions, derivatives, prodrugs or racemic mixtures thereof.

A compound of the invention comprises amyloid binding compounds. An amyloid binding compound of the invention can be labeled with any suitable marker (radiolabel or tag) to provide or comprise an amyloid probe. Amyloid binding compounds of the invention can bind (associated or interact) to amyloid deposits including deposits that comprise amyloid proteins or precursors, portions, fragments and peptides thereof and/or one or more Aβ and/or amyloidogenic proteins as well as any receptors of such. The compounds of the invention can also bind to amyloid proteins or precursors, portions, fragments and peptides thereof and/or one or more Aβ and/or amyloidogenic proteins as well as any receptors of such. The binding of amyloid binding compounds to amyloid deposits or amyloid proteins or precursors, portions, fragments and peptides thereof and/or one or more Aβ and/or amyloidogenic proteins (as well as any receptors of such) can be of high-affinity and a specific or preferential nature as would be understood by one of ordinary skill in the art and evaluated by conventional techniques related to binding (for example, dissociation constants). The amyloid binding compounds of the invention can include analogs, salts, pharmaceutical compositions, derivatives, prodrugs or racemic mixtures thereof. Moreover, amyloid binding compounds of the invention can be useful as therapeutic agents for the treatment or prophylaxis of amyloidosis or an amyloidosis-related disease state. In one aspect, the amyloid binding compounds of the invention are capable of preventing cell degeneration and toxicity associated with amyloid fibril formation. For example, an amyloid binding compound of the invention can inhibit cell degeneration and toxicity associated with fibril formation in an amyloidosis associated disease or malady. Preferably, an amyloid binding compound can be administered therapeutically to a subject (for example, a patient in need of treatment for an amyloidosis-related disease state) in an effective amount (for example, an amount capable of inhibiting cell degeneration and toxicity associated with fibril formation in an amyloidosis associated disease or malady) to treat a patient suffering from or thought to be at risk for an amyloidosis-related disease state.

Figure 2:
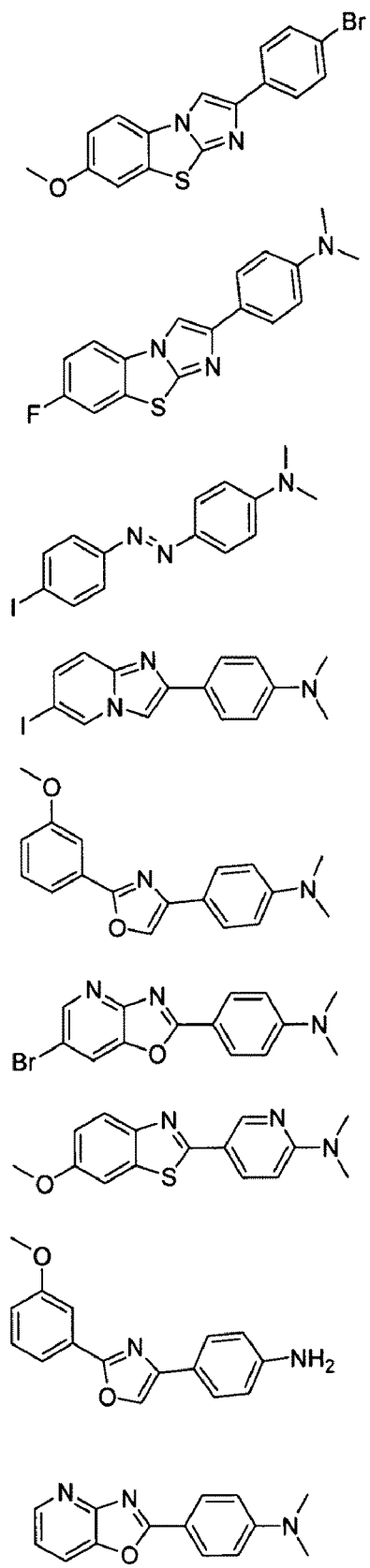
FIG. 2 includes exemplary structures for compounds of the invention, which can be modified to comprise one or more amyloid probes that can be useful for in vivo imaging of amyloid and/or amyloid deposits.
Figure 3:
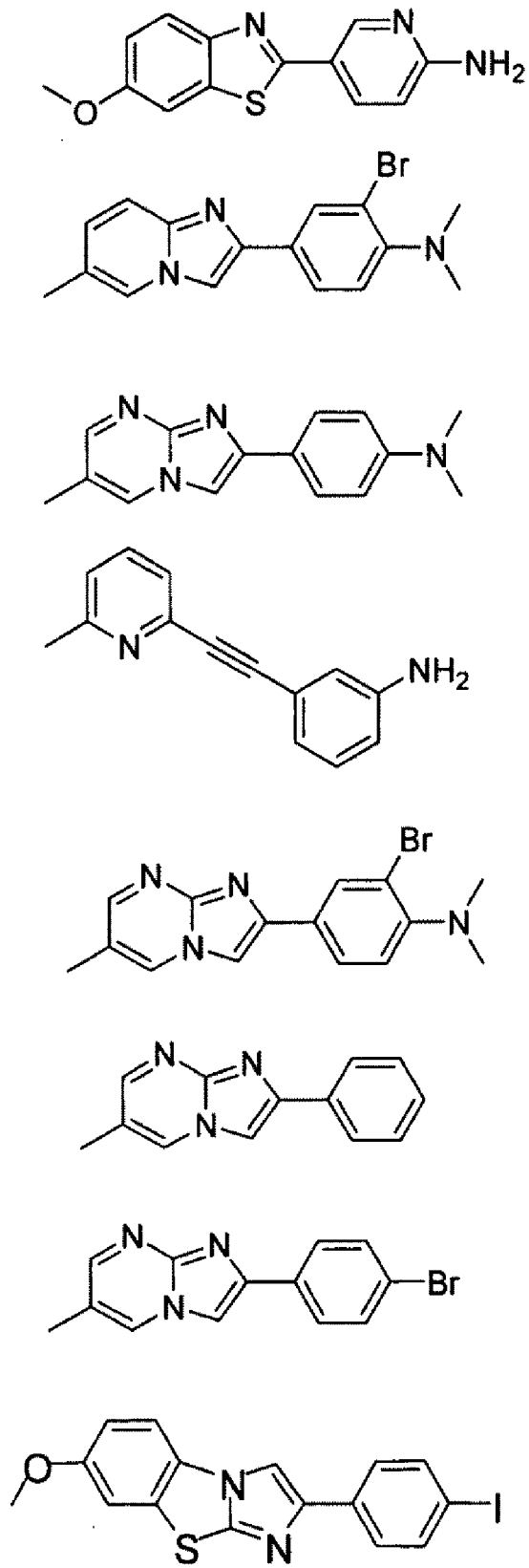
FIG. 3 includes exemplary structures for compounds of the invention, which can be modified to comprise one or more amyloid probes that can be useful for in vivo imaging of amyloid and/or amyloid deposits.

The term "in vivo" or "in vitro" in the context of detection or imaging can refer to any method that permits the detection of an amyloid probe of the invention or labeled compound such as, for example, a compound having an exemplary structure included in FIGS. 1, 2 or 3 or Tables 1, 2, 3 and 4. Similarly, an "in vivo method for detecting" or "in vitro method for detecting" as well as "use in detection" can comprise any type of detection for a compound or amyloid probe of the invention. Exemplary techniques for detection for a compound or probe of the invention include scintigraphy, radioscintigraphy, magnetic resonance imaging (MRI), chemilumensence, near infrared luminescence, fluorescence, SPECT, computed tomography (CT scan), positron emission tomography (PET) or combinations thereof and detection and related techniques are understood by those of ordinary skill in the art. Moreover, detection can include any future developed techniques related to the field of imaging. For gamma-based imaging, the radiation emitted from the organ or area being examined is measured and expressed either as total uptake or as a ratio in which total uptake in one tissue is normalized to (for example, divided by) the total uptake in another tissue of the same subject during the same in vivo imaging procedure. Total uptake in vivo is defined as the entire signal detected in a tissue by an in vivo imaging technique without the need for correction by a second administration of an identical quantity of a probe or labeled compound along with a large excess of unlabeled, but otherwise chemically identical, compound. Similarly, in vitro methods can involve obtaining a fresh or frozen tissue specimen and incubating a section of the tissue or a homogenate of the tissue with a labeled compound of the invention and then separating bound and free radiolabel by washing the tissue section or filtering and washing the tissue homogenate. The bound radioactivity can be measured by standard autoradiographic techniques or by liquid scintillation or gamma counting and compared to controls from the same tissue to which an excess of unlabeled compounds has been added.

A "subject" or "patient" is a mammal, preferably, a human, and, most preferably, a human suspected of having a disease associated with amyloid deposition such as AD and/or dementia. The term "subject" and "patient" can be used interchangeably. Moreover, any substituents for the compounds and amyloid probes of the invention are generally understood to be described herein in the alternative or, as appropriate, in a conjunctive manner. For example, a compound or amyloid probe of the invention can comprise substituents such as F, Cl, Br, I in the alternative or, as appropriate, in a conjunctive manner.

For purposes of in vivo or in vitro imaging, the type of detection instrument available is a major factor in selecting a given detectable marker. For example, radioactive isotopes and $^{18}$F or $^{123}$I are particularly suitable for in vivo imaging in the methods of the invention. The type of instrument used will also guide the selection of a radionuclide or stable isotope. In one aspect, the radionuclide chosen must have a type of decay detectable by a given type of instrument. Moreover, other considerations such as the half-life of the radionuclide are taken into account when selecting a detectable marker for in vivo imaging.

The half-life of a detectable marker should be long enough so that the marker is still detectable at the time of maximum uptake by the target, but short enough so that the subject does not sustain deleterious radiation. The amyloid probes of the invention can be detected using gamma imaging in which emitted gamma irradiation of the appropriate wavelength is detected. Conventional methods of gamma imaging include, but are not limited to, SPECT and PET. Preferably, for SPECT detection, the chosen detectable marker will lack a particulate emission, but will produce a large number of photons in a 140-300 keV range. For PET detection, the detectable marker will be a positron-emitting radionuclide such as $^{18}$F, which will annihilate to form two 511 keV gamma rays that can then be detected by a PET camera.

In one aspect, compounds or amyloid probes of the invention, which are useful for in vivo imaging and quantification of amyloid deposition, are administered to a patient. These compounds or probes are to be used in conjunction with non-invasive neuroimaging techniques such as MRS, MRI, PET, SPECT and combinations thereof. Preferably, a compound of the invention may be labeled with $^{19}$F or $^{13}$C to yield an amyloid probe for MRS/MRI using general organic chemistry techniques known to the art. March, J., Advanced Organic Chemistry: I Reactions, Mechanisms, and Structure (3rd Ed., 1985); Morrison and Boyd, Organic Chemistry (6th Ed., 1992). The compounds of the invention also may be radiolabeled with $^{18}$F, $^{11}$C, $^{7}$Br or $^{76}$Br for PET by techniques well known in the art and described by Fowler, J. and Wolf, A. in Positron Emission Tomography and Autoradiography (Phelps, M., Mazziota, J., and Schelbert, H., eds.) pp. 391-450 (Raven Press, NY 1986). The compounds of the invention also may be radiolabeled with $^{123}$I for SPECT by any of several techniques known to the art. Kulkarni, *Int. J. Rad. Appl. & Inst.*, (Part B) 18: 647 (1991).

A label, detectable label, radiolabel, tag, marker, detectable marker, tracer, radiotracer or equivalent term as generally understood by those of ordinary skill in the art can represent any substituent (group, moiety, position) suitable for imaging and/or assaying (for example, identifying, diagnosing, evaluating, detecting and/or quantitating) in vivo or in vitro. For example, an amyloid probe of the invention can comprise labels, radiolabels, tags, markers, detectable markers, tracers, radiotracers or equivalent terms suitable for in vivo or in vitro detection via radioscintigraphy, magnetic resonance imaging (MRI), assays, chemilumensence, near infrared luminescence, fluorescence, spectroscopy, gamma imaging, magnetic resonance imaging, magnetic resonance spectroscopy, fluorescence spectroscopy, SPECT, computed tomography (CT scan), positron emission tomography (PET). Suitable labels, radiolabels, tags, markers, detectable markers, tracers, radiotracers or equivalent terms are known by those skilled in the art and can include, for example, radioisotopes, radionuclides, isotopes, fluorescent groups, biotin (in conjunction with streptavidin complexation) or photoaffinity groups. Preferably, a label, detectable label, radiolabel, tag, marker, detectable marker, tracer, radiotracer of an amyloid probe of the invention can comprise $^{131}$I, $^{124}$I, $^{125}$I, $^{3}$H, $^{123}$I, $^{18}$I, $^{19}$F, $^{11}$C, $^{75}$Br, $^{13}$C, $^{13}$N, $^{15}$O, $^{76}$Br, $CH_2$—$CH_2$-Q, O—$CH_2$—$CH_2$-Q, $CH_2$—$CH_2$—$CH_2$-Q, or O—$CH_2$—$CH_2$—$CH_2$-Q, —$[OCH_2$—$CH_2]_n$-Q, O—$CH_2$—CH=CH-Q ((E) or (Z) configuration), N—$CH_2$—CH=CH-Q ((E) or (Z) configuration) in which "Q" can independently be $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O, $^{76}$Br, $^{11}$C or $^{13}$C, or $^{11}$C or $^{13}$C can be a label, detectable label, radiolabel, tag, marker, detectable marker, tracer, radiotracer as a substituent of a lower alky group, $(CH_2)_n$OR, $CL_3$, $CH_2$—$CH_2$-L, O—$CH_2$—$CH_2$-L, $CH_2$—$CH_2$—$CH_2$-L, O—$CH_2$—$CH_2$—$CH_2$-L, CN, (C=O)—R, (C=O)N(R)$_2$, O(CO)R, OR, COOR, aryl, CR=CR-aryl or $CR_2$—$CR_2$-aryl in which L can be a halogen (for example, $^{13}CH_2$—$CH_2$—F) and R can be H, F, Cl, Br, I or a lower alkyl group. "Photoaffinity group" or "photoaffinity labeled" can refer to a substituent on a compound or probe of the invention, which can be activated by photolysis at an appropriate wavelength to undergo a cross-linking photochemical reaction with a macromolecule associated therewith. An example of a photoaffinity group is a benzophenone substituent.

Suitable radioisotopes are known to those skilled in the art and include, for example, isotopes of halogens (such as chlorine, fluorine, bromine and iodine) and metals including technetium and indium. Exemplary labels, radiolabels, tags, markers, detectable markers, tracers, radiotracers can also include $^3$H, $^{11}$C, $^{14}$C, $^{18}$F, $^{32}$P, $^{35}$S, $^{123}$I, $^{125}$I, $^{131}$I, $^{124}$I, $^{19}$F, $^{75}$Br, $^{13}$C, $^{13}$N, $^{15}$O, $^{76}$Br. The amyloid probes of the invention may be labeled (radiolabeled, tagged, marked, detectablely marked, traced or radiotraced) either directly (that is, by incorporating the label directly into a compound of the invention) or indirectly (that is, by incorporating the label into a compound of the invention through a chelating agent, where the chelating agent has been incorporated into the compound). Furthermore, a label for an amyloid probe can be included as an additional substituent (group, moiety, position) to a compound of the invention or as an alternative substituent for any substituents that are present. For example, a label included as an additional substituent to the group —CH$_2$—CH=CH$_2$ of a compound of the invention can be CH$_2$—CH$_2$—CH$_2$—$^{131}$I. Moreover, a label provided as an alternative substituent for one or more substituents present for a compound of the invention can, by way of example, include CH$_2$—CH—CH$_3$ to CH$_2$—CH$_2$—CH$_2$—$^{131}$I, or —CH$_2$—CH=CH—I to —CH$_2$—CH=CH—$^{123}$I. A label, detectable label, radiolabel, tag, marker, detectable marker, tracer or radiotracer may appear at any substituent (group, moiety, position) on a compound or probe of the invention.

In one aspect, labeling can be isotopic or nonisotopic. With isotopic labeling, one substituent (group, moiety, position) already present in a compound of the invention can be substituted with (exchanged for) a radioisotope or isotope. With nonisotopic labeling, a radioisotope or isotope can be added to a compound of the invention without substituting with (exchanging for) an already existing group. Direct and indirect labeled compounds as well as isotopic and nonisotopic labeled compounds are contemplated by an amyloid probe of the invention comprising one or more labels, radiolabels, tags, markers, detectable markers, tracers or radiotracers and equivalents thereof. Preferably, a label, detectable label, radiolabel, tag, marker, detectable marker, tracer or radiotracer can be reasonably stable, both chemically and metabolically, applying recognized standards in the art. Moreover, although the compounds or probes of the invention may be labeled in any fashion (for example, via conventional techniques) with a variety of different substituents, as those skilled in the art can appreciate, such labeling may be performed in a manner so as to retain the high-affinity (binding affinity) and a specific or preferential nature of binding to amyloid deposits or amyloid proteins or precursors, portions, fragments and peptides thereof and/or one or more Aβ and/or amyloidogenic proteins (as well as any receptors of thereof). In one aspect, the affinity and specificity of a compound of the invention is not significantly affected by labeling to comprise an amyloid probe. By not significantly affected, affinity and specificity may not be affected by more than, for example, about 3 log units (preferably, not more than, for example, about 2 log units or, more preferably, not more than, for example, about 1 log unit). Furthermore, by not significantly affected, affinity and specificity may not be affected by more than, for example, about 500% (preferably, not more than, for example, about 250% or, more preferably, affinity and specificity may not be affected at all).

In addition, the compounds of the invention may be labeled with any suitable radioactive iodine isotope such as, but not limited to, $^{131}$I, $^{125}$I or $^{123}$I by iodination of a diazotized amino derivative directly via a diazonium iodide (Greenbaum, F., *Am. J. Pharm.*, 108: 17 (1936)), by conversion of the unstable diazotized amine to the stable triazene or by conversion of a non-radioactive halogenated precursor to a stable tri-alkyl tin derivative, which then can be converted to an iodo compound by several methods well known to the art. Satyamurthy and Barrio, *J. Org Chem.*, 48: 4394 (1983), Goodman et al., *J. Org. Chem.*, 49: 2322 (1984), Mathis et al., *J. Labell. Comp. and Radiopharm.*, 1994: 905; Chumpradit et al., *J. Med. Chem.*, 34: 877 (1991); Zhuang et al., *J. Med. Chem.*, 37: 1406 (1994); Chumpradit et al., *J. Med. Chem.*, 37: 4245 (1994). For example, a stable form or derivative of a compound of the invention can be reacted with a halogenating agent containing $^{131}$I, $^{125}$I, $^{123}$I, $^{75}$Br, $^{76}$Br or $^{18}$F. Thus, the stable form or derivative of a compound of the invention and analogs, salts, pharmaceutical compositions, derivatives, prodrugs, racemic mixtures or tautomeric forms thereof are precursors useful for the synthesis of many of the amyloid probes of the invention.

The compounds of the invention also may be radiolabeled with known metal detectable markers such as Technetium-99m ($^{99m}$Tc). Modification of the substituents to a compound of the invention in order to introduce ligands that bind such metal ions can be effected without undue experimentation by one of ordinary skill in the art. The metal radiolabeled compound of the invention can then be used as an amyloid probe to detect amyloid deposits. Preparing amyloid probes comprising a detectable marker such as $^{99m}$Tc is well known in the art. Zhuang et al., *Nuclear Medicine & Biology*, 26(2): 217 (1999); Oya et al., *Nuclear Medicine & Biology*, 25(2): 135 (1998); Hom et al., *Nuclear Medicine & Biology*, 24(6): 485 (1997).

In one aspect, a method of the invention may use isotopes detectable by nuclear magnetic resonance (NMR) spectroscopy for purposes of in vivo imaging and spectroscopy. Elements particularly useful in magnetic resonance spectroscopy include $^1$H, $^{19}$F and $^{13}$C. Suitable detectable markers for preparing an amyloid probe of the invention also include beta-emitters, gamma-emitters, positron-emitters and x-ray emitters. Moreover, exemplary detectable markers include $^{131}$I, $^{124}$I, $^{125}$I, $^3$H, $^{123}$I, $^{18}$F, $^{11}$C, $^{75}$Br, $^{13}$C, $^{13}$N, $^{15}$O and $^{76}$Br. Suitable stable isotopes for use in MRI or MRS, according to the invention, include $^{19}$F and $^{13}$C. In another aspect, suitable radioisotopes for in vitro quantification of amyloid in homogenates of biopsy or post-mortem tissue include $^{125}$I, $^{14}$C and $^3$H. Preferably, an amyloid probe of the invention comprises $^{11}$C, $^{124}$I or $^{18}$F for use in PET in vivo imaging, $^{123}$I for use in SPECT imaging, $^{19}$F for MRS/MRI and $^3$H or $^{14}$C for in vitro studies. Nonetheless, any conventional method or detectable markers for visualizing amyloid probes can be used in accordance with the invention and may be appreciated by those of ordinary skill in the art.

In one aspect of the invention relating to detecting amyloid deposits in biopsy tissue, a method is provided that involves incubating formalin-fixed tissue with a solution of a compound or amyloid probe of the invention. Preferably, the solution is 5-20% ethanol (with the remainder being 0.9% saline) saturated with a compound or amyloid probe of the invention. Alternatively, such a solution may be used for detection or quantitation of amyloid deposits in non-biopsied tissues. Given that the detection of amyloid deposits can be performed in biopsied tissue, the solution used for incubation can also be from 5-100% ethanol (with the remainder being water). Upon incubation, the compound or probe stains or labels the amyloid deposit in the tissue and the stained or labeled deposit can be detected or visualized by any standard method. Such detection means include microscopic techniques such as bright-field, fluorescence, laser-onfocal and cross-polarization microscopy. A method of quantifying the amount of amyloid in biopsy tissue involves incubating an amyloid probe or labeled compound of the invention or a water-soluble, non-toxic salt thereof with homogenate of biopsy or post-mortem tissue. The tissue is obtained and homogenized by techniques well known in the art.

Preferably, a detectable marker for an amyloid probe or labeled compound of the invention is a radiolabel, although other labels such as enzymes, chemiluminescent and immunofluorescent labels are well known to skilled artisans. In one aspect, a detectable marker such as $^{125}$I, $^{14}$C or $^3$H can be used to label a compound of the invention such as a compound having an exemplary structure included in FIGS. 1, 2 or 3 or Tables 1, 2, 3 and 4. Tissue containing amyloid deposits will bind to the compounds or amyloid probes of the invention. For biopsied tissues, the bound tissue can then be separated from the unbound tissue by any mechanism known to the skilled artisan such as filtering. The bound tissue may also be quantified through any means known to the skilled artisan. The units of tissue-bound probes or labeled compounds of the invention are then converted to units of micrograms of amyloid per 100 mg of tissue by comparison to a standard curve generated by incubating known amounts of amyloid with a probe or labeled compound of the invention.

In one aspect, a method of the invention can determine the presence and location of amyloid deposits in an organ, tissue or body area of a subject. For example, a method of the invention can be used to detect the presence and location of amyloid deposits in the brain of a subject suffering from an amyloidosis-related disease or malady including, but not limited to, AD, familial AD, homozygotes for the apolipoprotein E4 allele, glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease and Islets of Langerhans diabetes Type II insulinoma.

The ability of a compound or probe of the invention to preferentially (or specifically) bind to amyloid plaques may vary depending on concentration, although the determination of specific concentrations to achieve binding that can be effective for therapy and/or imaging (for example, identifying, diagnosing, evaluating, detecting and/or quantitating amyloid deposits or an amyloidosis-related disease state) would be routine to the skilled artisan. For example, the probes or labeled compounds may be specific for Aβ deposits at concentrations less than 50 nM. These low concentrations are also detectable with imaging studies including PET. The use of the probes or labeled compounds of the invention also permits detection in amyloid deposits such as those found in plaques and cerebrovascular amyloid. Give that it has been reported that Aβ levels in the frontal cortex are increased prior to neurofibrillary tangle formation, the invention contemplates that probes or labeled compounds of the invention, used as detectable labels, would be specific for the earliest changes in AD cortex. Naslund et al. *JAMA,* 283: 1571 (2000).

When the compounds of the invention are modified to be used as amyloid probes, they may be labeled with suitable radioactive halogen isotopes. Although $^{125}$I isotopes are useful for laboratory testing, they will generally not be useful as a detectable marker for actual diagnostic purposes given the relatively long half-life (60 days) and low gamma-emission (30-65 Kev) of $^{125}$I. The isotope $^{123}$I has a half-life of thirteen hours and a gamma energy of 159 KeV such that amyloid probes comprising this detectable marker can be readily used for diagnostic purposes. Other isotopes which may be used for in vivo imaging include $^{131}$I (half-life of 8.3 days). Suitable bromine isotopes for an amyloid probe of the invention also include $^{77}$Br, $^{75}$Br and $^{76}$Br.

The compounds and probes of the invention lend themselves easily to formation from materials that could be provided to users in kits. For example, kits for forming the amyloid probes can contain, without limitation, a vial containing a physiologically suitable solution of an intermediate of a compound of the invention in a concentration and at a pH suitable for optimal complexing conditions. The user would add to the vial an appropriate quantity of a detectable marker, for example, Na$^{123}$I and an oxidant such as hydrogen peroxide. The resulting probe may then be administered intravenously to a patient such that amyloid plaque in the brain can be imaged antemortem by a means for measuring the gamma ray or photo emissions from the probe.

In one aspect, a method of the invention may be used to diagnose AD in mild or clinically confusing cases. For example, the method provides for longitudinal studies of amyloid deposition in high risk populations including, without limitation, patients suffering from or believed to be at risk of suffering from Down's syndrome, familial AD or homozygotes for the apolipoprotein E4 allele. Corder et al., *Science,* 261: 921 (1993). The method also provides for the temporal sequence of amyloid deposition to be followed to determine if deposition occurs long before dementia begins or if deposition is unrelated to dementia. The method of the invention can also be used to monitor the effectiveness of therapies targeted at preventing amyloid deposition.

As indicated, the specific method of detection of a compound or probe of the invention can vary, depending upon the chemical and physical nature of the species utilized and detected. For gamma-emitting species, standard, commercially available single photon and positron detection methods can be utilized. For magnetic nuclear spin detection, standard, commercially available magnetic resonance imaging and spectroscopy techniques can be utilized.

In the methods of the invention, data collection using conventional and developing technologies can be conducted according to standard clinical imaging protocols involving whole body imaging techniques such as repeatedly moving the subject through the scanner over the course of the scanning period. In one aspect, data collection may be achieved by imaging selectively over one or more regions of interest in the body, for example, by emphasizing the brain, lungs, liver, heart or kidneys using a limited range of patient body coverage in an imaging scanner. Following the administration of a compound or probe of the invention, imaging data collection can begin immediately and proceed for several hours post administration using a dynamic imaging protocol. Late-time snapshots of about 30 minutes could also be taken following the in vivo distribution of the compound or amyloid probe using standard static late time imaging protocols. Imaging data can then be collected and stored electronically in an automated and routine fashion, for later processing and analysis. Data processing and analysis can make use of commercially available software packages, which are typically installed by the manufacturer on the single photon, positron emission or magnetic resonance scanners' operating system computers.

Examples of these processes and methods for detecting, collecting and processing imaging data are established in the art for positron emission methodologies. Price et al., *J Cereb. Blood Flow Metab.,* 25: 1528 (2005) and Lopresti et al.,

*Nuclear Medicine*, 46: 1959 (2005). Analogous data collection and processing of single photon, positron and magnetic resonance species are similarly conducted for systemic amyloid deposits using standard, commercially available scanners, data collection methodologies and data processing techniques in body regions including the brain.

The invention also provides a method for the treatment or prophylaxis of a disease characterized by amyloid deposition and/or amyloidosis comprising administering to a patient in need thereof an effective amount of a compound of the invention. In one aspect, the method can include providing a patient suffering from or believed to be at risk of suffering from a disease characterized by, for example, amyloid deposition and/or amyloidosis. The method may also comprise administering to the patient an effective amount of a compound of the invention. The compound of the invention can also be administered as part of a composition comprising a pharmaceutically acceptable carrier.

In another aspect, a method for detecting or quantitating a disease characterized by amyloid deposition and/or amyloidosis comprising administering to a patient in need thereof an effective amount of an amyloid probe of the invention. For example, the method can comprise a patient suffering from or believed to be at risk of suffering from a disease characterized by, without limitation, amyloid deposition and/or amyloidosis. The method may also comprise administering to the patient an effective amount of an amyloid probe of the invention and, optionally, imaging the probe in vivo. Exemplary means for imaging of an amyloid probe of the invention in vivo include, without limitation, MRS, MRI, PET, SPECT or combinations thereof.

"Effective amount" can refer to the amount required to produce a desired effect. One example of an effective amount includes amounts or dosages that enable detecting, quantitation and imaging of amyloid deposits in vivo or in vitro. In one aspect, the amyloid deposits can comprise one or more amyloid or amyloidogenic proteins. Another example of an effective amount includes amounts or dosages that yield acceptable toxicity and bioavailability levels for imaging or therapeutic (pharmaceutical) use including, but not limited to, the treatment or prophylaxis of amyloidosis or an amyloidosis-related disease state. Another example of an effective amount includes amounts or dosages that are capable of preventing cell degeneration and toxicity associated with amyloid fibril formation.

A method of the invention relates to inhibiting cell degeneration and toxicity associated with fibril formation in an amyloidosis associated disease or malady. Preferably, the method comprises administering to a subject in need thereof a compound or amyloid probe of the invention (or analogs, salts, pharmaceutical compositions, derivatives, prodrugs or racemic mixtures thereof) in an effective amount, for example, an amount capable inhibiting cell degeneration and toxicity associated with fibril formation in an amyloidosis associated disease or malady. Examples of amyloidosis associated diseases or maladies include, but are not limited to, AD, familial AD, homozygotes for the apolipoprotein E4 allele, glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease and Islets of Langerhans diabetes Type II insulinoma.

The invention also provides a method of distinguishing a normal brain from one comprising amyloid deposits indicative of a disease state or malady. In one aspect, the method comprises obtaining tissue samples from the cerebellum and another area of the brain of a normal subject. Furthermore, the method includes obtaining comparable tissue samples from subjects suffering from or suspected of suffering from a disease such as, for example, AD. These tissue samples are made into separate homogenates using methods well known to the skilled artisan and are then incubated with an amyloid probe of the invention. The amount of tissue that binds to the probe is calculated for each tissue sample type, for example, cerebellum, non-cerebellum, normal or abnormal and a ratio for the binding of non-cerebellum to cerebellum tissue is calculated. These ratios are may also be compared to each other. In one aspect, if the ratio from the brain suspected of having a disease such as AD is above about 40%, 50%, 60%, 70%, 80% or 90% (preferably, for example, above 50% and, more preferably, for example, above 90%) of the ratios obtained from normal brains, the diagnosis of a disease state is made. The normal ratios can be obtained from previously obtained data or, alternatively, they may be recalculated at the same time the suspected brain tissue is studied via a method of the invention.

In one aspect, a pharmaceutical composition comprising an amyloid probe can also be prepared easily and simply by a user with a kit. For example, the invention provides a kit comprising as materials therefor a non-radiolabeled compound of the invention. Optionally, the compound can be in a dry condition and, also optionally, one or more inert, pharmaceutically acceptable carriers and/or auxiliary substances may be added thereto. A kit of the invention can also include materials such as a reducing agent and, optionally, a chelator. These materials may also be combined. Moreover, the kit can comprise instructions for carrying out a method that involves reacting the materials with a detectable marker including, without limitation, $^{123}I$, $^{125}I$, $^{124}I$, $^{131}I$, $^{18}F$, $^{75}Br$, $^{76}Br$ or $^{99m}Tc$. An exemplary $^{99m}Tc$ detectable marker can be in the form of a pertechnetate solution that is, optionally, included with a kit of the invention. Similarly, the detectable marker can also be included with the kit. The kit can also include instructions for performing an in vivo imaging protocol with an amyloid probe prepared therefrom.

In one aspect, a pertechnetate solution for a kit of the invention can be obtained from a molybdenum-technetium-generator. Such generators are available in a number of institutions that perform radiodiagnostic procedures. As indicated, the materials for a kit of the invention may be combined, provided they are compatible. Such a monocomponent kit, in which the combined materials are preferably lyophilized, is suitable to be reacted by the user with the pertechnetate solution in a simple manner that will be appreciated by those of ordinary skill in the art.

The invention also provides a method for preparing an amyloid probe comprising a $^{99m}Tc$ detectable marker by reacting $^{99m}Tc$ as a pertechnetate in the presence of a reducing agent and, optionally, a suitable chelator. For example, the reducing agent serves to reduce the $^{99m}Tc$ perteclnetate, which is eluted from a molybdenum-technetium-generator in a physiological solution such as saline. Suitable reducing agents are, for example, dithionite, formamidine sulphinic acid, diaminoethane disulphinate or metallic agents such as Sn(II), Fe(II), Cu(I), Ti(III) or Sb(III). In one aspect, $^{99m}Tc$ is reacted with a compound of the invention as a salt or in the form of Tc bound to comparatively weak chelators. For the latter, a $^{99m}Tc$ complex is formed by ligand exchange. Examples of suitable chelators for a method of the invention include, without limitation, dicarboxylic acids such as oxalic acid, malonic acid, succinic acid, maleic acid, orthophtalic acid, malic acid, lactic acid, tartaric acid, citric acid, ascorbic acid, salicylic acid or derivatives thereof, phosphorus compounds such as pyrophosphates and enolates. Preferably, citric acid, tartaric acid, ascorbic acid, glucoheptonic acid or derivatives thereof can be used as a chelate of $^{99m}Tc$ given that each undergoes a ligand exchange particularly easily.

In one aspect, $[Tc^VO]^{+3}N_2S_2$ complexes are prepared based on stannous (II) chloride reduction of $[^{99m}Tc]$-pertechnetate. The method of labeling can rely on a $^{99m}Tc$ ligand exchange reaction between $^{99m}Tc$ (Sn)glucoheptonate and the $N_2S_2$ ligand. Preparation of stannous (II) chloride and preserving it in a consistent stannous (II) form is necessary for the success of the labeling reaction. To stabilize the air-sensitive stannous ion, it may be preferably to use a lyophilized kit in which the stannous ion is in a lyophilized powder form mixed with an excess amount of glucoheptonate under an inert gas such as nitrogen or argon. The preparation of a lyophilized stannous chloride/sodium glucoheptonate kit may ensure that the method of labeling is reproducible and predictable. The $N_2S_2$ ligands can be air-sensitive (thiols are easily oxidized by air) such that they may need be preserved by using lyophilized kits containing 100-500 μg of the ligands under argon or nitrogen.

When desired, an amyloid probe of the invention or pharmaceutical composition thereof may contain any additive such as pH controlling agents (for example, acids, bases, buffers), stabilizers (for example, ascorbic acid) or isotonizing agents (for example, sodium chloride). It will also be appreciated that the methods of the invention can be performed in conjunction with other in vivo techniques such as, for example, PET or SPECT imaging for evaluating one or more additional characteristics of the subject including, but not limited to, neuronal cell loss, glucose metabolic activity or behavioral characteristics. Exemplary behavioral characteristics can often be assessed by MMSE and Buschke scores. In one aspect, one or more in vivo techniques can be used to detect or quantitate amyloid and/or amyloid deposits and monitor regional decreases in glucose metabolism in parietal and temporal lobes of a patient.

In one aspect, the invention also contemplates the use of stable $\eta^5$-substituted cyclopentadienyltricarbonyl rhenium and technetium organometallic complexes for radiolabeling one or more compounds of the invention. These complexes may be abbreviated collectively as $CpMet(CO)_3$ complexes in which Met is metal or referred to individually as cyclopentadienyltricarbonylrhenium $(CpRe(CO)_3)$ for the rhenium and $CpTc(CO)_3$ for the technetium analogs. As compared to the more widely used high oxidation state metal-oxo complexes, $CpMet(CO)_3$ complexes exhibit high chemical and metabolic stability, are lipophilic and relatively small and, unlike many inorganic chelates, do not possess additional stereocenters. Thus, these complexes can be useful for the development of amyloid probes or metal-labeled compounds of the invention. The preparation and use of low valent (for example, $Met(CO)_3^+$) technetium and rhenium are also known to those of skill in the art. For example, the suitability of $CpMet(CO)_3$ conjugates as amyloid ligands has been shown by a series of $CpRe(CO)_3$ and manganese conjugates with nanomolar affinity.

A practical radiochemical preparation of substituted $CpMet(CO)_3$ complexes was the double ligand transfer (DLT) reaction, originally reported in 1992. Improved versions of the DLT reaction that minimize the formation of unwanted byproducts are also known to those in the art. While not being bound by theory, this transformation involves the in situ reduction/carbonylation of the permetalate species, followed by selective ring transfer from an appropriately substituted ferrocene precursor. The reaction can occur in a single pot and, in most cases, is limited to ferrocenes substituted with electron withdrawing groups. However, use of a DLT reaction for labeling compounds of the invention may require additional steps in order to conjugate the substituted CpMet $(CO)_3$ to the compound. The invention also contemplates alternative routes to $CpRe(CO)_3$ complexes without a requirement for substitution with an electron withdrawing group. For example, one technique known in the art involves a "three-component condensation" reaction and the stannane approach.

To extend the DLT methodology further and to expand structure-activity relationships for organometallic amyloid probes, a direct version of the DLT reaction can also be used according to the invention. In general, for one or more compounds of the invention, a direct version of the DLT reaction can be applied to a series of ferrocenyl phenyl benzoxazole conjugates and the binding affinity of the compounds to amyloid deposits can be measured. Although such rhenium compounds could be made more efficiently without going through a ferrocene intermediate, the purpose may be to develop methods that could be applied to short-lived γ emitting radiotracers. Additional ligands can also be made by the three-component condensation. Besides the innate interest in the rhenium compounds as organometallic amyloid probes, they serve as analogs of radioactive rhenium and technetium agents that may be useful for SPECT imaging. The conditions for metal incorporation such as high temperature, pressure in organic solvent and chromatographic purification are also known to those of ordinary skill in the art.

In one aspect of the invention, an amyloid probe is introduced into a tissue or a patient in a detectable quantity. The probe may be part of a pharmaceutical composition and is administered to the tissue or the patient by methods well known to those skilled in the art. For example, the compound can be administered either orally, rectally, parenterally (intravenous, by intramuscularly or subcutaneously), intracisternally, intravaginally, intraperitoneally, intravesically, locally (powders, ointments or drops) or as a buccal or nasal spray as well as ocular drops.

In another aspect, an amyloid probe of the invention is introduced into a patient in a detectable quantity and after sufficient time has passed for the compound to become associated with amyloid deposits, the probe is detected. The protocol is noninvasive (without incision) as the probe inside the patient is detected by, for example, an imaging device, apparatus, means or system outside the patient. Alternatively, an amyloid probe of the invention is introduced into a patient, sufficient time is allowed for the probe to become associated with amyloid deposits and then a sample of tissue from the patient is removed and the probe in the tissue is detected apart from the patient. A tissue sample can also be removed from a patient and an amyloid probe introduced into the tissue sample. After a sufficient amount of time has passed for the amyloid probe to become bound to amyloid deposits, the probe is detected by a suitable imaging modality.

The administration of an amyloid probe to a patient can be by a general or local administration route. For example, the amyloid probe may be administered to the patient such that it is delivered throughout the body. Alternatively, the amyloid probe can be administered to a specific organ or tissue of interest. In one aspect, it may be desirable to locate and quantitate amyloid deposits in the brain in order to diagnose or track the progress of AD in a patient.

A compound or amyloid probe of the invention can also be modified, for example, by the covalent attachment of an organic moiety or conjugate to improve pharmacokinetic properties, toxicity or bioavailability (e.g., increased in vivo half-life). The conjugate can be a linear or branched hydrophilic polymeric group, fatty acid group or fatty acid ester group. A polymeric group can comprise a molecular weight that can be adjusted by one of ordinary skill in the art to improve, for example, pharmacokinetic properties, toxicity or bioavailability. Exemplary conjugates can include a polyalkane glycol (e.g., polyethylene glycol (PEG), polypropylene glycol (PPG)), carbohydrate polymer, amino acid polymer or polyvinyl pyrolidone and a fatty acid or fatty acid ester group, each of which can independently comprise from about eight to about seventy carbon atoms. Conjugates for use with a compound or amyloid probe of the invention can also serve as linkers to, for example, any suitable substituents or groups, radiolabels (marker or tags), halogens, proteins, proteins, enzymes, polypeptides, other therapeutic agents (for example, a pharmaceutical or drug), nucleosides, dyes, oligonucleotides, lipids, phospholipids and/or liposomes. In one aspect, conjugates can include polyethylene amine (PEI), polyglycine, hybrids of PEI and polyglycine, polyethylene glycol (PEG) or methoxypolyethylene glycol (mPEG). A conjugate can also link a compound of the invention to, for example, a label or marker (radionuclide, radioisotope and/or isotope) to comprise a probe of the invention. Conjugates for use with a compound or probe of the invention can, in one aspect, improve in vivo half-life. Other exemplary conjugates for use with a compound or probe of the invention as well as applications thereof and related techniques include those generally described by U.S. Pat. No. 5,672,662, which is hereby incorporated by reference herein.

Lipids can include synthetic or naturally-occurring compounds, which are generally amphipathic and biocompatible. The lipids typically comprise a hydrophilic component and a hydrophobic component. Exemplary lipids include fatty acids, neutral fats, phosphatides, glycolipids, aliphatic alcohols, waxes, terpenes, steroids and surfactants. "Lipid composition" can refer to a composition which comprises a lipid compound, typically in an aqueous medium. Exemplary lipid compositions include suspensions, emulsions and vesicle compositions. Similarly, liposome can refer to a generally spherical cluster or aggregate of amphipathic compounds (including lipid compounds) typically in the form of one or more concentric layers, for example, bilayers. They may also be referred to herein as lipid vesicles. The liposomes may be formulated, for example, from ionic lipids and/or non-ionic lipids.

The terms "tissue" or "organ" can mean a part of a patient's body. Examples of tissues or organs include the brain, heart, liver, blood vessels, arteries, mesodermal tissue, tenosynovium, joints, aortic, thyroid, islets of Langerhans, aging pituitary, Iatrogenic, cardiac atria, cornea, lens, vitreous humor, retina, sclera, pancreas or parenchymatous organ. A detectable or imaging effective quantity is a quantity of an amyloid probe or labeled compound of the invention necessary to be detected by the detection method chosen. For example, a detectable quantity can be an administered amount sufficient to enable detection of binding of the probe to amyloid and/or amyloid deposits. The amount of an amyloid probe to be introduced into a patient in order to provide for detection can readily be determined by those skilled in the art. For example, increasing amounts of the amyloid probe can be given to a patient until the probe is detected by the detection method of choice. A detectable marker is introduced to the compounds of the invention to provide for an amyloid probe that can be detected by suitable imaging modalities. In one aspect, a method of the invention determines the presence and location of amyloid deposits in an organ or body area, preferably, the brain of a patient. The method comprises administration of a detectable quantity of an amyloid probe or pharmaceutical composition thereof.

Those skilled in the art are also familiar with determining the amount of time sufficient for a compound or amyloid probe to become associated with amyloid deposits. The amount of time necessary can easily be determined by introducing a detectable amount of an amyloid probe of the invention into a patient and then detecting the probe at various times after administration.

The terms "associated" and/or "binding" can mean a chemical or physical interaction between a compound or amyloid probe of the invention and an amyloid deposit. In one aspect, an amyloid deposit can comprise amyloid proteins or precursors, portions, fragments and peptides thereof and/or one or more Aβ and/or amyloidogenic proteins. Preferably, the compounds of the invention and probes thereof are amyloid binding compounds. Examples of associations or interactions include covalent bonds, ionic bonds, hydrophilic-hydrophilic interactions, hydrophobic-hydrophobic interactions and complexes. Associated can also refer generally to "binding" or "affinity" as each can be used to describe various chemical or physical interactions. Measuring binding or affinity is also routine to those skilled in the art. For example, compounds or probes of the invention can bind to or interact with amyloid proteins or precursors, portions, fragments and peptides thereof and/or their deposits as well as deposits that can comprise one or more amyloid and/or amyloidogenic proteins. Those skilled in the art are familiar with the various ways to detect labeled compounds. For example, MRI, PET or SPECT can be used to detect amyloid probes of the invention. The label that is introduced to a compound of the invention to yield an amyloid probe can depend on the detection method desired. As indicated, if PET is selected as a detection method, the amyloid probe must possess a positron-emitting atom such as $^{11}$C or $^{18}$F.

In one aspect, the amyloid probe should also have sufficient radioactivity and radioactivity concentration to assure reliable diagnosis. Without limitation, for $^{99m}$Tc, the probe may be included usually in an amount from 0.1 to 100 mCi in about 0.5 to 5.0 ml at the time of administration. The amount of a compound of the invention may be such as is sufficient to form a stable chelate compound or amyloid probe with the radioactive metal.

The imaging of amyloid deposits can also be carried out quantitatively so that the amount of amyloid deposits can be determined. In one aspect, amyloid probes for imaging include a radioisotope such as $^{123}$I, $^{125}$I, $^{124}$I, $^{131}$I, $^{18}$F, $^{75}$Br or 76Br. The invention also provides a method of imaging amyloid deposits. One of the key prerequisites for an in vivo imaging agent of the brain is the ability to cross the intact blood-brain barrier after, for example, a bolus intravenous injection.

In another aspect, a method of inhibiting amyloid plaque aggregation is provided. For example, the invention provides a method of inhibiting the aggregation of amyloid proteins to form amyloid deposits by administering to a patient an amyloid inhibiting amount of a compound of the invention.

Those skilled in the art are readily able to determine an amyloid inhibiting amount by simply administering a compound of the invention to a patient in increasing amounts until the growth of amyloid deposits is decreased or stopped. The rate of growth can be assessed using in vivo imaging, as described, or by taking a tissue sample from a patient and observing the amyloid deposits therein. The compounds of the invention can be administered to a patient at dosage levels in the range of about 0.1 to about 1,000 mg per day. For a normal human adult having a body weight of about 70 kg, a dosage in the range of about 0.01 to about 100 mg per kilogram of body weight per day is sufficient. The specific dosage used, however, can vary or may be adjusted as considered appropriate by those of ordinary skill in the art. For example, the dosage can depend on a number of factors including the requirements of the patient, the severity of the condition being treated and the pharmacological activity of the compound being used. The determination of optimum dosages for a particular patient is well known to those skilled in the art.

The term "alkyl" by itself or as part of another group can refer to both straight and branched chain radicals of up to 8 carbons, preferably, 5 carbons, more preferably, 4 carbons such as methyl, ethyl, propyl, isopropyl, butyl, t-butyl and isobutyl. A compound or amyloid probe of the invention can also comprise one or more alkyl substituents (for example, as A linker) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "alkenyl" can refer to an unsaturated straight or branched chain hydrocarbon radical comprising at least one carbon to carbon double bond. Examples include without limitation ethenyl, propenyl, iso-propenyl, butenyl, iso-butenyl, tert-butenyl, n-pentenyl and n-hexenyl. Moreover, "alkynyl" can refer to an unsaturated straight or branched chain hydrocarbon radical comprising at least one carbon to carbon triple bond. Examples include without limitation ethynyl, propynyl, iso-propynyl, butynyl, iso-butynyl, tert-butynyl, pentynyl and hexynyl. A compound or amyloid probe of the invention can also comprise one or more alkenyl or alkynyl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "alkoxy" can mean a straight or branched chain alkyl radical, as indicated, bonded to an oxygen atom including, but not limited to, methoxy, ethoxy, n-propoxy, isopropoxy and the like. Preferably, the alkoxy chain is 1 to 6 carbon atoms in length and, more preferably, 1-4 carbon atoms in length. A compound or amyloid probe of the invention can also comprise one or more alkoxy substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "monoalkylamine" by itself or as part of another group can refer to an amino group that is substituted with one alkyl group as indicated. In one aspect, the term "methylamino" can refer to a neutral group or ring substituent in which N is connected to a compound of the invention via the ring or a chain of the compound and N is further bound to a methyl and a hydrogen. Moreover, the N may be charged and may form a salt. A compound or amyloid probe of the invention can also comprise one or more monoalkylamine substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "dialkylamine" by itself or as part of another group can refer to an amino group that is substituted with two alkyl groups as indicated. In one aspect, the term "dimethylamino" can refer to a neutral group or ring substituent in which N is connected to a compound of the invention via the ring or a chain of the compound and N is further bound to two methyl groups. In addition, the N may be charged and may form a salt. A compound or amyloid probe of the invention can also comprise one or more dialkylamine substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "hydroxy($C_{1-5}$)alkyl" can refer to an alkyl chain connected to a compound of the invention via the ring or a chain of the compound in which the distal portion of the alkyl chain of the group contains a hydroxy moiety. The alkyl chain can contain any number of carbons, but, preferably, the number of carbons in the alkyl chain is from 1 to 5. A compound or amyloid probe of the invention can also comprise one or more hydroxy($C_{1-5}$)alkyl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "halo" or "halogen" by itself or as part of another group can refer to chlorine, bromine, fluorine or iodine. A compound or amyloid probe of the invention can also comprise one or more halo substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "haloalkyl" can refer to any of the mentioned alkyl groups substituted by one or more chlorine, bromine, fluorine or iodine with fluorine and chlorine such as chloromethyl, iodomethyl, trifluoromethyl, 2,2,2-trifluoroethyl and 2-chloroethyl. A compound or amyloid probe of the invention can also comprise one or more haloalkyl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "alkylthio" by itself or as part of another group can refer to a thioether of the structure: $R^x$—S in which $R^x$ is a $C_{1-4}$ alkyl as indicated. A compound or amyloid probe of the invention can also comprise one or more alkylthio substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "alkylsulfonyl" by itself or as part of another group can refer to a sulfone of the structure: $R^y$—$SO_2$ in which $R^y$ is a $C_{1-4}$ alkyl as indicated. A compound or amyloid probe of the invention can also comprise one or more alkylsulfonyl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "aryl" by itself or as part of another group can refer to monocyclic or bicyclic aromatic groups containing from 6 to 12 carbons in the ring portion, preferably, 6-10 carbons in the ring portion such as phenyl, naphthyl or tetrahydronaphthyl. A compound or amyloid probe of the invention can also comprise one or more aryl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "carboxy" can refer to the group —$COOR_4$ in which $R_4$ may be hydrogen or any suitable substituent including, for example, F, Cl, Br, I, $NO_2$, CN, $CF_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl or aralkyl groups. Carboxy can also generally refer to esterified carboxy (—$COOR_4$ in which $R_4$ can be alkyl) or amidate carboxy (—$CONHR_4$ in which may be hydrogen or any suitable substituent including, for example, F, Cl, Br, I, $NO_2$, CN, $CF_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl or aralkyl groups) groups. A compound or amyloid probe of the invention can also comprise one or more carboxyl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "heterocycle" or "heterocyclic ring" can represent a stable 4 to 7-membered mono-heterocyclic ring system that may be saturated or unsaturated, and consist of carbon atoms and from one to three heteroatoms selected from the group consisting of N, O and S. Moreover, the nitrogen and sulfur heteroatom may optionally be oxidized. Especially useful are rings containing one nitrogen combined with one oxygen or sulfur or two nitrogen heteroatoms. Examples of such heterocyclic groups include piperidinyl, pyrrolyl, pyrrolidinyl, imidazolyl, imidazinyl, imidazolidinyl, pyridyl, pyrazinyl, pyrimidinyl, oxazolyl, oxazolidinyl, isoxazolyl, isoxazolidinyl, thiazolyl, thiazolidinyl, isothiazolyl, homopiperidinyl, homopiperazinyl, pyridazinyl, pyrazolyl, and pyrazolidinyl, most preferably thiamorpholinyl, piperazinyl and morpholinyl. A compound or amyloid probe of the invention can also comprise one or more heterocycle or heterocyclic ring substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "heteroatom" can mean an oxygen atom ("O"), a sulfur atom ("S") or a nitrogen atom ("N"). It will also be recognized that when the heteroatom is nitrogen, it may form an $NR^aR^b$ moiety in which $R^a$ and $R^b$ are, independently from one another, hydrogen, $C_{1-4}$ alkyl, $C_{2-4}$ aminoalkyl, $C_{1-4}$ halo alkyl or halo benzyl. Moreover, $R^a$ and $R^b$ can be taken together to form a 5 to 7-member heterocyclic ring that optionally comprises O, S or $NR^c$ in which $R^c$ is hydrogen or $C_{1-4}$ alkyl. A compound or amyloid probe of the invention can also comprise one or more heteroatom substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "heteroaryl" can refer to groups having 5 to 14 ring atoms, 6, 10 or 14 n electrons shared in a cyclic array and containing carbon atoms and 1, 2 or 3 oxygen, nitrogen or sulfur heteroatoms in which examples of heteroaryl groups are thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4aH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups. A compound or amyloid probe of the invention can also comprise one or more heteroaryl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

The term "aralkyl" or "arylalkyl" by itself or as part of another group can refer to $C_{1-6}$ alkyl groups as indicated having an aryl substituent such as benzyl, phenylethyl or 2-naphthylmethyl. A compound or amyloid probe of the invention can also comprise one or more aralkyl or arylalkyl substituents (for example, as $A_{linker}$) included via general organic chemistry techniques known to the art. March, J., Advanced Organic Chemistry: I Reactions, Mechanisms, and Structure (3rd Ed., 1985); Morrison and Boyd, Organic Chemistry (6th Ed., 1992).

Exemplary radiotracers can be used to, for example, study amyloid distributions via radioscintigraphy, magnetic resonance imaging (MRI), chemilumensence, near infrared luminescence, fluorescence, spectroscopy, gamma imaging, magnetic resonance imaging, magnetic resonance spectroscopy, fluorescence spectroscopy, SPECT, computed tomography (CT scan), positron emission tomography (PET) or combinations thereof. The invention also contemplates the use of conventional imaging protocols, means, devices, apparatuses or systems for performing radioscintigraphy, magnetic resonance imaging (MRI), chemilumensence, near infrared luminescence, fluorescence, SPECT, computed tomography (CT scan), positron emission tomography (PET) or combinations thereof. Exemplary imaging protocols, means, devices, apparatuses or systems include those generally described in U.S. Pat. Nos. 6,072,177, 6,803,580, 5,900,636, 6,271,524, 5,532,489, 5,272,343, 5,241,181, 5,512,755, 5,345,082, 5,023,895, 4,864,140, 5,323,006, 4,675,526 and 4,395,635, each of which are incorporated by reference herein.

The examples herein are provided to illustrate advantages of the present invention and to further assist a person of ordinary skill in the art with preparing or using the compounds or amyloid probes of the invention or salts, pharmaceutical compositions, derivatives, prodrugs, racemic mixtures or tautomeric forms thereof. The examples herein are also presented in order to more fully illustrate the preferred aspects of the invention. The examples should in no way be construed as limiting the scope of the invention, as defined by the appended claims. The examples can include or incorporate any of the variations, aspects or aspects of the invention described above. The variations, aspects or aspects described above may also further each include or incorporate the variations of any or all other variations, aspects or aspects of the invention. For example, a compound of the invention can comprise any suitable detectable marker, tag or label to yield an amyloid probe that can be used to diagnose and study the progression or regression of disease states or maladies that include, for example, AD, familial AD, homozygotes for the apolipoprotein E4 allele, glaucoma, Mediterranean fever, Muckle-Wells syndrome, idiopathic myeloma, amyloid polyneuropathy, amyloid cardiomyopathy, systemic senile amyloidosis, amyloid polyneuropathy, hereditary cerebral hemorrhage with amyloidosis, Down's syndrome, Scrapie, Creutzfeldt-Jacob disease, Kuru, Gerstmann-Straussler- Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease and Islets of Langerhans diabetes Type II insulinoma.

EXAMPLE I

Series I Compounds of the Invention

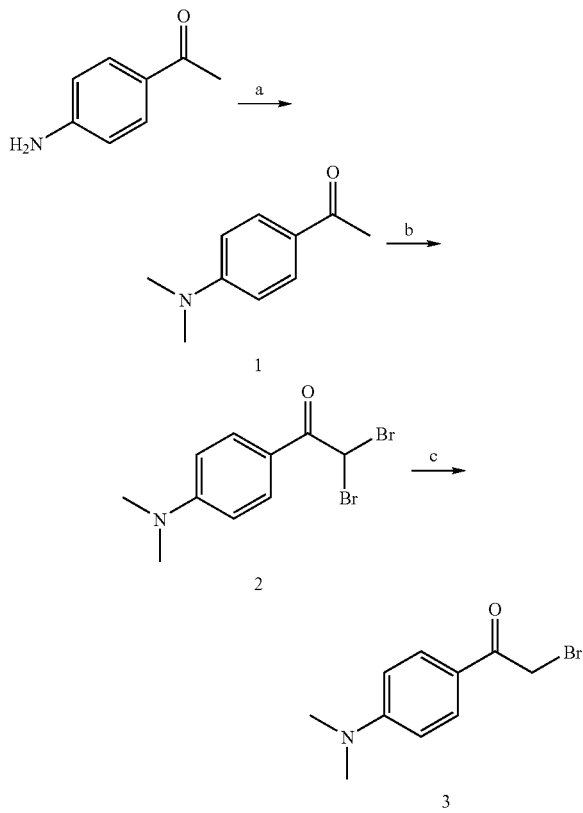

a Formaldehyde 37%/HCl 37%/PtO$_2$/H$_2$/EtOH
b Br$_2$/H$_2$SO$_4$ and
c PO(OEt)$_2$/Et$_3$N/THF

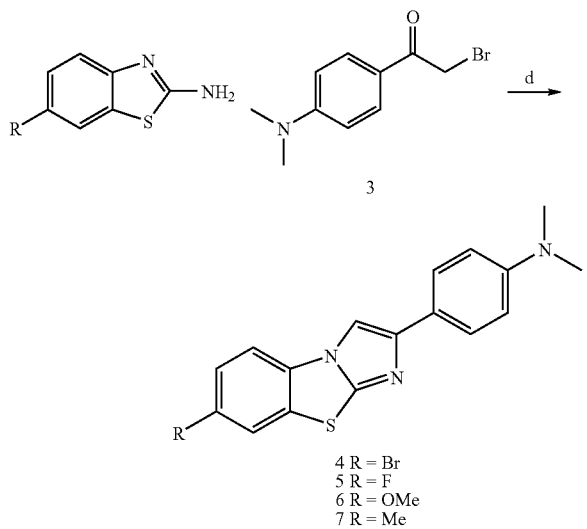

4 R = Br
5 R = F
6 R = OMe
7 R = Me d NaHCO$_3$/EtOH/reflux

4'-dimethylaminoacetophenone (1)

In a mixture EtOH/HCl 37% 80 ml/5 ml was dissolved 4'-aminoacetophenone (13.5 g, 0.1 mole), then formaldehyde 37% (15 ml) was added followed by PtO$_2$ (150 mg). The resulting solution was hydrogenated at 50 PSI for 1 h, filtered through celite, evaporated and purified by flash chromatography (SiO$_2$, hexane/AcOEt, 8/2) giving 1 as a white solid in 62% yield.

NMR $^1$H (CDCl$_3$), $\delta$=2.30 (s, 3H, CH$_3$); 2.85 (s, 6H, 2CH$_3$); 6.44 (d, 2H, J=9.0 Hz, 2CHAr); 7.67 (d, 2H, J=9.0 Hz, 2CHAr). NMR $^{13}$C (CDCl$_3$), $\delta$=26.3 (1C, CH$_3$); 40.4 (2C, 2CH$_3$); 110.9 (2C, CHAr); 125.6 (1C, Cq), 130.9 (2C, CHAr); 153.7 (1C, Cq); 196.7 (1C, Cq).

2,2-dibromo-4'-dimethylaminoacetophenone (2)

In 20 ml of concentrated H$_2$SO$_4$ was dissolved 1 (3.8 g, 1 eq), then at 0° C. bromine (1.19 ml, 1 eq) was added dropwise and the resulting mixture was stirred at RT for 6 h before being poured into 200 ml of ice/H$_2$O. The resulting precipitate was collected by filtration, washed with H$_2$O, dissolved in CH$_2$Cl$_2$, dried over Na$_2$SO$_4$ and concentrated in vacuum to give 2 as a green solid in 68% yield, which was directly used in the next step without any purification.

2-bromo-4'-dimethylacetophenone (3)

In 30 ml of THF was dissolved 2 (5.1 g, 1 eq), then at 0° C. was added dropwise a mixture of diethylphosphite (2.04 ml, 1 eq) and Et$_3$N (2.4 ml, 1.1 eq) in 12 ml of THF. The resulting mixture was stirred 6 h at RT, then evaporated and poured into 200 ml of ice/H2O and the resulting precipitated was filtered, washed with H$_2$O and dried in vacuum. 3 was obtained as a green solid in 89% yield.

NMR $^1$H (CDCl$_3$), $\delta$=2.97 (s, 6H, 2CH$_3$); 4.45 (s, 2H, CH$_2$); 6.57 (d, 2H, J=9.0 Hz, 2CHAr); 7.72 (d, 2H, CHAr). NMR $^{13}$C (CDCl$_3$), $\delta$=31.3 (1C, CH$_2$); 40.4 (2C, CH$_3$); 111.1 (2C, CHAr); 121.8 (1C, Cq); 131.6 (2C, CHAr); 154.1 (1C, Cq); 189.7 (1C, Cq).

An Exemplary Method for the Synthesis of 4 Through 7

In the minimum volume of EtOH was dissolved the commercially available 2-amino-6- substituted-benzothiazole (2 mmol), then 3 (2 mmol) was added and the resulting mixture was refluxed for 2 h before addition of NaHCO$_3$ (3 mmol). After 6 h more of reflux, the mixture was hydrolyzed with H$_2$O (5 ml), extracted using AcOEt (4×25 ml), dried over Na$_2$SO$_4$, concentrated in vacuum and purified by flash chromatography (SiO$_2$, hexane/AcOEt, 1/1).

7-bromo-2-(4-dimethylaminophenyl)-imidazo[2,1-b] benzothiazole (4)

NMR $^1$H (DMSO-d$_6$), $\delta$=2.93 (s, 6H, 2CH$_3$); 6.77 (d, 2H, J=8.5 Hz, 2CHAr); 7.67 (d, 2H, J=8.5 Hz, 2CHAr); 7.71 (d, 1H, J=8.5 Hz, CHAr); 7.88 (d, 1H, J=8.5 Hz, CHAr); 8.29 (s, 1H, CHAr); 8.50 (s, 1H, CHAr). NMR $^{13}$C (DMSO-d$_6$), $\delta$=40.4 (2C, CH$_3$); 107.2 (1C, CHAr); 112.6 (2C, CHAr); 114.9 (1C, CHAr); 116.6 (1C, Cq); 122.1 (1C, Cq); 126.0 (2C, CHAr); 127.6 (1C, CHAr); 129.7 (1C, CHAr); 131.5 (1C, Cq); 146.8 (1C, Cq); 147.7 (1C, Cq); 150.1 (1C, Cq). HRMS Calcd for C$_{17}$H$_{15}$N$_3$BrS: 372.0170, found: 372.0171. Anal. Calcd for C$_{17}$H$_{14}$N$_3$BrS: C, 54.85%; H, 3.79%; N, 11.29%, found: C, 54.49%; H, 3.73%; N, 11.06%.

7-fluoro-2-(4-dimethylaminophenyl)-imidazo[2,1-b]benzothiazole (5)

NMR $^1$H (CDCl$_3$), δ=2.97 (s, 6H, 2CH$_3$); 6.71 (d, 2H, J=8.5 Hz, CHAr); 7.08 (td, 1H, J=8.8, 2.8 Hz, CHAr); 7.33 (dd, 1H, J=8.0, 2.4 Hz, CHAr); 7.43 (dd, 1H, J=8.8, 4.4 Hz, CHAr), 7.70 (s, 1H, CHAr). HRMS Calcd for C$_{17}$H$_{15}$N$_3$FS: 312.0971, found: 312.0959. Anal. Calcd for C$_{17}$H$_{14}$N$_3$FS, 0.2 H$_2$O: C, 64.82%; H, 4.61%; N, 13.34%, found: C, 64.89%; H, 4.41%; N, 13.25%.

7-methoxy-2-(4-dimethylaminophenyl)-imidazo[2,1-b]benzothiazole (6)

NMR $^1$H (CDCl$_3$), δ=2.88 (s, 6H, 2CH$_3$); 3.66 (s, 3H, CH$_3$); 6.62 (d, 2H, J=9.0 Hz, CHAr); 6.74 (dd, 1H, J=8.8, 2.4 Hz, CHAr); 6.96 (d, 1H, J=2.4 Hz, CHAr); 7.17 (d, 1H, J=8.8 Hz, CHAr); 7.51 (s, 1H, CHAr); 7.58 (d, 2H, J=9.0 Hz, CHAr). NMR $^{13}$C (CDCl$_3$), δ=40.9 (2C, CH3); 56.2 (1C, CH$_3$); 105.4 (1C, CHAr); 108.9 (1C, CHAr); 112.9 (2C, CHAr); 113.2 (1C, CHAr); 113.4 (1C, CHAr); 122.8 (1C, Cq); 126.3 (2C, CHAr); 126.8 (1C, Cq); 131.5 (1C, Cq); 147.2 (1C, Cq); 148.1 (1C, Cq); 150.2 (1C, Cq); 157.2 (1C, Cq). MS m/z: 324.2 (M+1). Anal. Calcd for C$_{18}$H$_{17}$N$_3$OS, 2 HCl, 2 H$_2$O: C, 50.00%; H, 5.36%; N, 9.72%, found: C, 49.66%; H, 5.44%; N, 9.39%.

7-methyl-2-4-dimethylaminophenyl)-imidazo[2,1-b]benzothiazole (7)

NMR $^1$H (CDCl$_3$), δ=2.39 (s, 3H, CH$_3$); 3.00 (s, 6H, 2CH$_3$); 6.80 (d, 2H, J=8.8 Hz, CHAr); 7.20 (d, 1H, J=8.0 Hz, CHAr); 7.45 (d, 1H, J=8.0 Hz, CHAr); 7.47 (s, 1H, CHAr); 7.76 (d, 2H, J=8.8 Hz, CHAr); 7.79 (s, 1H, CHAr). NMR $^{13}$C (CDCl$_3$), δ=21.7 (1C, CH$_3$); 41.0 (2C, CH$_3$); 105.4 (1C, CHAr); 112.5 (1C, CHAr); 113.0 (2C, CHAr); 122.8 (1C, Cq); 124.7 (1C, CHAr); 126.5 (2C, CHAr); 127.4 (1C, CHAr); 130.5 (1C, Cq); 130.6 (1C, Cq); 134.9 (1C, Cq); 147.1 (1C, Cq); 148.3 (1C, Cq); 150.3 (1C, Cq). HRMS Calcd for C$_{18}$H$_{18}$N$_3$S: 308.1221, found: 308.1207. Anal. Calcd for C$_{18}$H$_{17}$N$_3$S, CH$_2$Cl$_2$: C, 58.16%; H, 4.88%, N, 10.71%, found: C, 57.85%; H, 4.85%; N, 10.87%.

Exemplary Compounds of the Invention in Series I

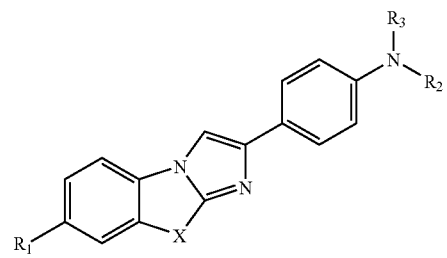

Series 1: X = S
R1 = F, Br, I, OMe, Me, SnMe3, SnBu3
R2 = R3 = H

Series 2: X = O
R1 = F, Br, I, OMe, Me, SnMe3, SnBu3
R2 = R3 = H

Series 3: X = S
R1 = F, Br, I, OMe, Me, SnMe3, SnBu3
R2 = H
R3 = Me

Series 4: X = O
R1 = F, Br, I, OMe, Me, SnMe3, SnBu3
R2 = H
R3 = Me

Series 5: X = S
R1 = F, Br, I, OMe, Me, SnMe3, SnBu3
R2 = R3 = Me

Series 6: X = O
R1 = F, Br, I, OMe, Me, SnMe3, SnBu3
R2 = R3 = Me

Series 7: X = S
R1 = F, Br, I, OMe, Me, SnMe3, SnBu3
R2 = H
R3 = 

Series 8: X = O
R1 = F, Br, I, OMe, Me
R2 = H
R3 = 

Series 9: X = S
R1 = F, Br, I, OMe, Me, SnMe3, SnBu3
R2 = H
R3 = SO2Me

Series 10: X = O
R1 = F, Br, I, OMe, Me, SnMe3, SnBu3
R2 = H
R3 = SO2Me

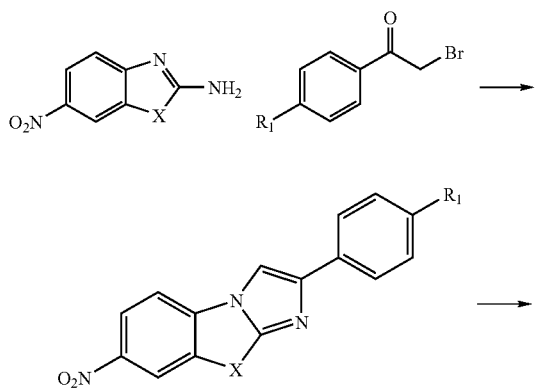

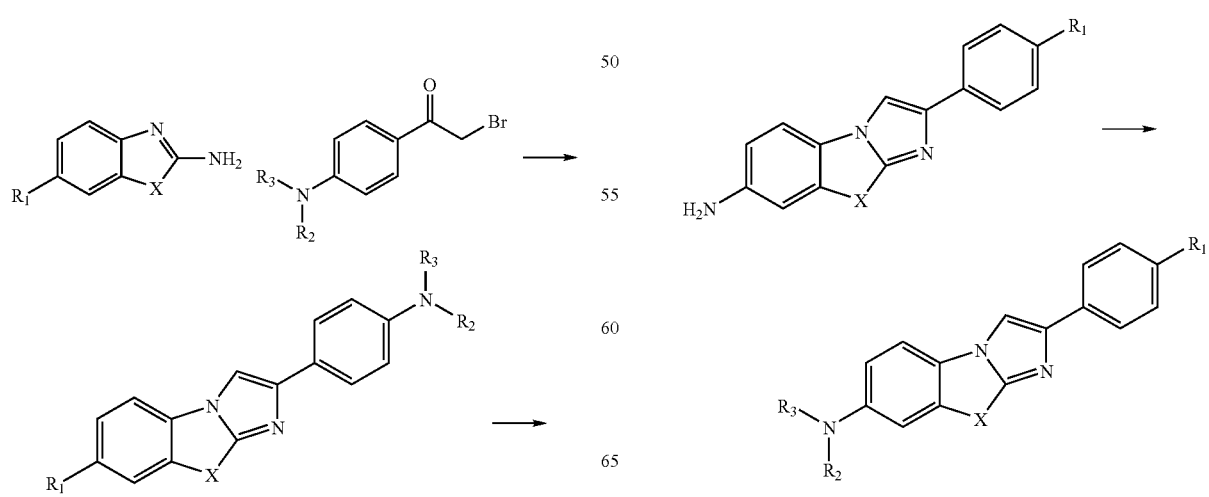

-continued

Series 11: X = S
R1 = F, Br, I, OMe,
Me, SnMe3, SnBu3
R2 = R3 = H

Series 12: X = O
R1 = F, Br, I, OMe,
Me, SnMe3, SnBu3
R2 = R3 = H

Series 13: X = S
R1 = F, Br, I, OMe,
Me, SnMe3, SnBu3
R2 = H
R3 = Me

Series 14: X = O
R1 = F, Br, I, OMe,
Me, SnMe3, SnBu3
R2 = H
R3 = Me

Series 15: X = S
R1 = F, Br, I, OMe,
Me, SnMe3, SnBu3
R2 = R3 = Me

Series 16: X = O
R1 = F, Br, I, OMe,
Me, SnMe3, SnBu3
R2 = R3 = Me

Series 17: X = S
R1 = F, Br, I, OMe,
Me, SnMe3, SnBu3
R2 = H
R3 = 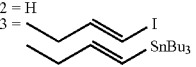

Series 18: X = O
R1 = F, Br, I, OMe, Me
R2 = H
R3 = 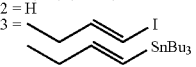

Series 19: X = S
R1 = F, Br, I, OMe,
Me, SnMe3, SnBu3
R2 = H
R3 = SO2Me

Series 20: X = O
R1 = F, Br, I, OMe,
Me, SnMe3, SnBu3
R2 = H
R3 = SO2Me

EXAMPLE II

Series II Compounds of the Invention

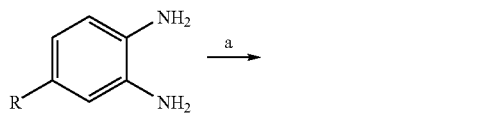

8a R = H
8b R = Br mixture of 3 and 4 bromo
8c R = I mixture of 3 and 4 iodo
8d R = Cl mixture of 3 and 4 chloro
8e R = F mixture of 3 and 4 fluoro
8f R = OMe mixture of 3 and 4 methoxy
9g R = NO2 mixture of 3 and 4 nitro

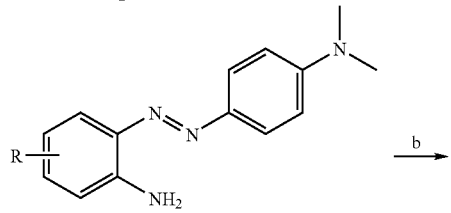

9a R = H
9b R = Br
9c R = I
9d R = Cl
9e R = F
9f R = OMe
9g R = NO2

9f →c 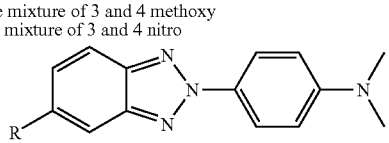

9h

9g →d

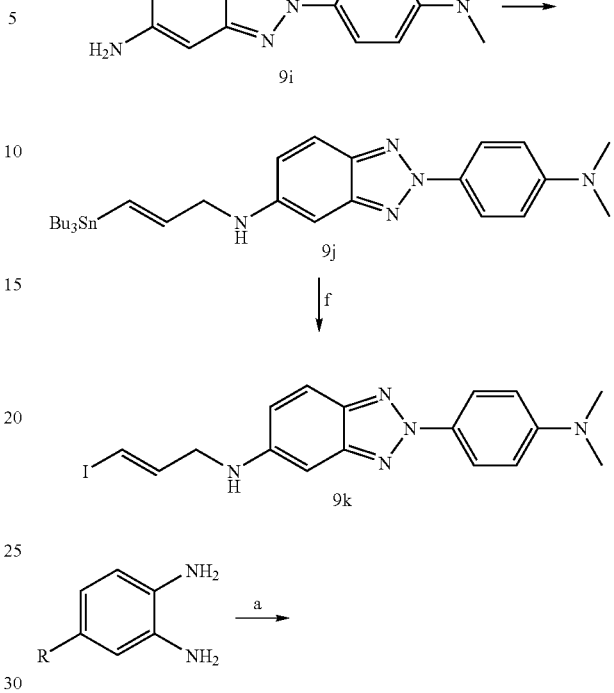

9i

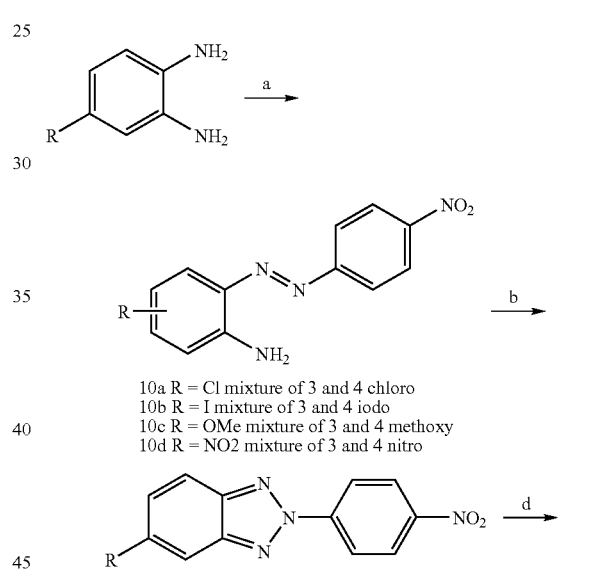

9j

9k

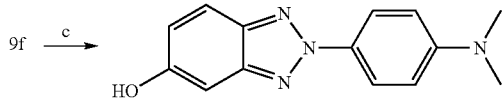

10a R = Cl mixture of 3 and 4 chloro
10b R = I mixture of 3 and 4 iodo
10c R = OMe mixture of 3 and 4 methoxy
10d R = NO2 mixture of 3 and 4 nitro

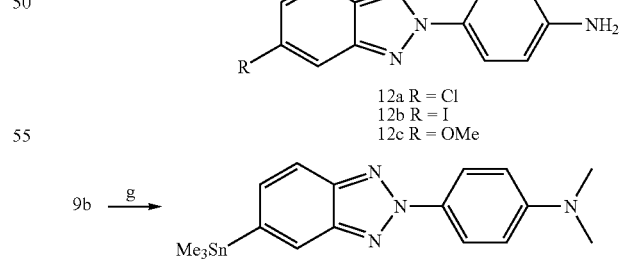

11a R = Cl
11b R = I
11c R = OMe
11d R = NO2

12a R = Cl
12b R = I
12c R = OMe

9b →g

14

-continued

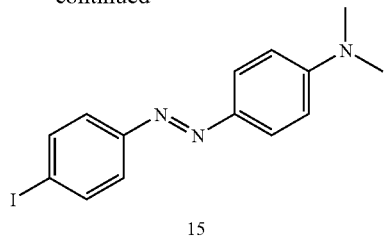

15 a 4-dimethylaminonitrozoaniline or 4-nitronitrozoaniline/NaOH/20-70° C.,
b Pb(OAc)$_4$/CH$_2$Cl$_2$,
c BBr$_3$,
d SnCl$_2$/EtOH reflux,
e TsOCH$_2$CHCHSnBu$_3$/DIEA,
f I$_2$ and
g (i) BuLi/THF/-78° C. and (ii) Me$_3$SnCl

2-(2-(4-dimethylaminophenyl)diazenyl)benzeneamine (8a)

o-Phenylenediamine (2 g, 1 eq), 4-dimethylaminonitrozoaniline (2.77 g, 1 eq) and NaOH (740 mg, 1 eq) were mixed neat and heated at 70° C. for 20 min with constant triturating. The resulting paste was extracted with toluene, concentrated in vacuum and purified by flash chromatography (SiO$_2$, hexane/AcOEt, 8/2) giving 8a as a red solid in 43% yield.

NMR $^1$H (CDCl$_3$), δ=2.89 (s, 6H, 2CH$_3$); 5.44 (bs, 2H, NH$_2$); 6.59-6.62 (m, 3H, 3CHA3); 6.67 (td, 1H, J=8.0, 1.2 Hz, CHAr); 7.02 (td, 1H, J=8.0, 1.2 Hz, CHAr); 7.64 (dd, 1H, J=8.0, 1.2 Hz, CHAr); 7.70 (d, 2H, J=9.2 Hz, CHAr). NMR $^{13}$C (CDCl$_3$), δ=40.4 (2C, CH$_3$); 111.7 (2C, CHAr); 116.8 (1C, CHAr); 117.5 (1C, CHAr); 125.6 (2C, CHAr); 126.1 (1C, CHAr); 130.7 (1C, CHAr); 137.8 (1C, Cq); 143.1 (1C, Cq); 143.9 (1C, Cq); 151.9 (1C, Cq).

1-(2-amino-4 and 5-bromophenyl)-2-(4-dimethylaminophenyl)diazene (8b)

4-bromo-1,2-phenylenediamine (1.5 g, 1 eq), 4-dimethylaminonitrozoaniline (1.2 g, 1 eq) and NaOH (450 mg, 1 eq) were mixed neat and heated at 70° C. for 20 min with constant triturating. The resulting paste was extracted with toluene, concentrated in vacuum and purified by flash chromatography (SiO$_2$, hexane/AcOEt, 8/2) giving a mixture of two isomers (3 and 4 bromo) as a red solid in 39% yield. The less polar isomer was isolated and characterized.

NMR $^1$H (CDCl$_3$), δ=2.99 (s, 6H, 2CH$_3$); 5.59 (s, 2H, NH$_2$); 6.67 (d, 2H, J=9.2 Hz, CHAr); 6.79-6.82 (m, 2H, CHAr); 7.50 (d, 1H, J=8.4 Hz, CHAr); 7.71 (d, 2H, J=9.2 Hz, CHAr).

1-(2-amino-4 and 5-iodophenyl)-2-(4-dimethylaminophenyl)diazene (8c)

4-iodo-1,2-phenylenediamine (2 g, 1 eq), 4-dimethylaminonitrozoaniline (1.26 g, 1 eq) and NaOH (340 mg, 1 eq) were mixed neat and heated at 70° C. for 20 min with constant triturating. The resulting paste was extracted with toluene, concentrated in vacuum and purified by flash chromatography (SiO$_2$, hexane/AcOEt, 8/2) giving a mixture of two isomers (3 and 4 iodo) as a red solid in 32% yield.

1-(2-amino-4 and-5-chlorophenyl)-2-(4-dimethylaminophenyl)diazene (8d)

Using the same methodology as for 8c, compound 8d was obtained as a mixture of two isomers (3 and 4 chloro) as a red solid in 38% yield.

1-(2-amino-4 and-5-fluorophenyl)-2-(4-dimethylaminophenyl)diazene (8e)

Using the same methodology as for 8c, compound 8e was obtained as a mixture of two isomers (3 and 4 fluoro) as a red solid in 37% yield.

1-(2-amino-4 and-5-methoxyphenyl)-2-(4-dimethylaminophenyl)diazene (8f)

Using the same methodology as for 8c, compound 8f was obtained as a mixture of two isomers (3 and 4 methoxy) as a red solid in 53% yield.

1-(2-amino-4 and-5-nitrophenyl)-2-(4-dimethylaminophenyl)diazene (8g)

Using the same methodology as for 8c, compound 8 g was obtained as a mixture of two isomers (3 and 4 nitro) as a red solid in 64% yield.

4-2H-benzo[d][1,2,3]triazol-2-yl-N,N-dimethylbenzenamine (9a)

In CH$_2$Cl$_2$ was dissolved 8a (1g, 1 eq) and a solution of Pb(OAc)$_4$ (2.03 g, 1.1 eq) in which CH$_2$Cl$_2$ was added dropwise. The resulting solution was stirred 30 min at RT, then hydrolyzed with 1 5 ml of Na$_2$CO$_3$ salt, extracted with CH$_2$Cl$_2$, dried by Na$_2$SO$_4$, evaporated and purified by flash chromatography (SiO$_2$, hexane/AcOEt, 8/2) giving 9a as an orange solid in 37% yield.

NMR $^1$H (CDCl$_3$), δ=2.84 (s, 6H, 2CH$_3$); 6.62 (d, 2H, J=9.2 Hz, CHAr); 7.23 (dd, 2H, J=6.5, 2.8 Hz, CHAr); 7.78 (dd, 2H, J=6.5, 2.8 Hz, CHAr); 8.06 (d, 2H, J=9.2 Hz, CHAr). NMR $^{13}$C (CDCl$_3$), δ=40.4 (2C, CH$_3$); 111.9 (2C, CHAr); 117.9 (2C, CHAr); 121.7 (2C, CHAr); 126.3 (2C, CHAr); 130.2 (1C, Cq); 144.7 (2C, Cq); 150.7 (1C, Cq).

4-(5-bromo-2H-benzo[d][1,2,3]triazol-2-yl)-N,N-dimethylbenzenamine (9b)

Using the same methodology as for 9a (starting from the mixture 8b), 9b was obtained as an orange solid in 33% yield.

NMR $^1$H (CDCl$_3$), δ=2.97 (s, 3H, CH$_3$); 6.70 (d, 2H, J=9.2 Hz, CHAr); 7.36 (dd, 1H, J=9.0, 2.0 Hz, CHAr); 7.67 (dd, 1H, J=8.0, 0.4 Hz, CHAr); 7.99 (d, 1H, J=0.4 Hz, CHAr); 8.08 (d, 2H, J=9.2 Hz, CHAr). NMR $^{13}$C (CDCl$_3$), δ=40.3 (2C, CH$_3$); 111.1 (1C, CHAr); 119.0 (2C, CHAr); 120.2 (1C, CHAr); 123.4 (1C, Cq); 124.2 (2C, CHAr); 126.2 (1C, CHAr); 143.8 (1C, Cq); 146.3 (1C, Cq); 151.0 (1C, Cq).

4-(5-iodo-2H-benzo[d][1,2,3]triazol-2-yl)-N,N-dimethylbenzenamine (9c)

Using the same methodology as for 9a (starting from the mixture 8c), 9c was obtained as an orange solid in 10% yield.

NMR $^1$H (CDCl$_3$), δ=2.95 (s, 6H, 2CH$_3$); 6.68 (dd, 2H, J=8.8, 2.0 Hz, CHAr); 7.51 (dd, 1H, J=8.8, 2.0 Hz, CHAr); 7.56 (dd, J=8.8, 0.4 Hz, CHAr); 8.06 (dd, 2H, J=8.8, 2.0 Hz, CHAr); 8.22 (s, 1H, CHAr). NMR $^{13}$C (CDCl$_3$), δ=40.4 (2C, CH$_3$); 91.0 (1C, Cq); 111.9 (2C, CHAr); 119.4 (1C, CHAr); 121.7 (2C, CHAr); 126.9 (1C, CHAr); 135.0 (1C, CHAr); 143.6 (1C, Cq); 146.2 (1C, Cq); 150.9 (1C, Cq).

4-(5-chloro-2H-benzo[d][1,2,3]triazol-2-yl)-N,N-dimethylbenzenamine (9d)

Using the same methodology as for 9a (starting from the mixture 8d), 9d was obtained as an yellow solid in 34% yield.
NMR $^1$H (CDCl$_3$), δ=2.93 (6H, s); 6.66 (2H, d, J=7.4 Hz); 7.21 (1H, dd, J=1.4 Hz, J=7.2 Hz); 7.72 (1H, d, J=7.2 Hz); 7.77 (1H, d, J=1.4 Hz); 8.04 (2H, d, J=7.4 Hz). NMR $^{13}$C (CDCl$_3$), δ=40.5 (2C); 112.3 (2C); 117.3, 119.4, 122.1 (2C); 128.1, 130.3, 132.4, 143.5, 145.4, 151.3.

4-(5-fluoro-2H-benzo[d][1,2,3]triazol-2-yl)-N,N-dimethylbenzenamine (9e)

Using the same methodology as for 9a (starting from the mixture 8e), 9e was obtained as an yellow solid in 23% yield.
NMR $^1$H (CDCl$_3$), δ=2.96 (6H, s); 6.70 (2H, d, J=9.1 Hz); 7.09 (1H, td, J=2.1 Hz, J=8.7 Hz); 7.41 (1H, dd, J=2.0 Hz, J=8.7 Hz); 7.79 (1H, m); 6.70 (2H, d, J=9.1 Hz). NMR $^{13}$C (CDCl$_3$), δ=40.4(2C); 101.4(d); 111.9(2C); 117.6(d); 119.4, 119.5, 121.1 (2C); 131.2, 141.8, 144.6 (d); 150.8.

4-(5-methoxy-2H-benzo[d][1,2,3]triazol-2-yl)-N,N-dimethylbenzenamine (9f)

Using the same methodology as for 9a (starting from the mixture 8f), 9f was obtained as an yellow solid in 28% yield.
NMR $^1$H (CDCl$_3$), δ=2.95 (6H, s); 3.81 (3H, s); 6.71 (2H, d, J=9.2 Hz); 6.97 (1H, dd, J=2.3 Hz, J=9.2 Hz); 7.04 (1H, d, J=2.3 Hz); 7.68 (1H, d, J=9.2 Hz); 8.04 (2H, d, J=9.2 Hz). NMR $^{13}$C (CDCl$_3$), δ=40.5 (2C); 55.5, 94.8, 112.1 (2C); 118.7, 121.2, 121.3 (2C); 126.1, 140.8, 145.6, 150.5, 158.8.

4-(5-nitro-2H-benzo[d][1,2,3]triazol-2-yl) N,N-dimethylbenzenamine (9g)

Using the same methodology as for 9a (starting from the mixture 8 g), 9 g was obtained as an yellow solid in 23% yield.
NMR $^1$H (CDCl$_3$), δ=3.03 (6H, s); 6.70 (2H, d, J=7.2 Hz); 7.92 (1H, d, J=9.2 Hz); 8.14-8.18 (3H, m); 8.82 (1H, d, J=2.0 Hz). NMR $^{13}$C (CDCl$_3$), δ=40.4 (2C); 113.4 (2C); 118.1, 119.7, 122.6 (2C); 128.1, 131.4, 135.9, 148.2, 151.3.

4-(5-hydroxy-2H-benzo[d][1,2,3]triazol-2-yl)-N,N-dimethylbenzenamine (9h)

Under N$_2$, 130 mg (5 mmol) of 9f was dissolved in (5 ml) CH$_2$Cl$_2$, at 0° C. was slowly added 0.458 ml (50 mmol) of BBr$_3$. The solution was stirred overnight at room temperature. The reaction was poured into ice/water and alkalinized with Na$_2$CO$_3$ (aqueous) and the organic layer was extracted and dried over Na$_2$SO$_4$. After removing the solvent by evaporation, the residue was purified by chromatography (dichloromethane/ethyl acetate, 95/5). The solvent was evaporated to obtain 91 mg (74%) of 9h as yellow solid.
NMR $^1$H (CD$_3$OD), δ=4.52 (6H, s); 6.37 (1H, sl); 8.35 (2H, d, J=8.9 Hz); 8.53-8.55 (2H, m); 9.21 (1H, d, J=9.7 Hz); 9.53 (2H, d, J=8.9 Hz). NMR $^{13}$C (CD$_3$OD), δ=42.1 (2C); 99.8, 114.8 (2C); 121.0, 123.4, 123.7 (2C); 133.2, 143.1, 148.6, 153.7, 159.4.

4-(5-amino-2H-benzo[d][1,2,3]triazol-2-yl)-N,N-dimethylbenzenamine (9i)

Under N$_2$, 350 mg (1.2 mmol) of 9 g with 1.1 g (5 mmol) of tin(II) chloride was stirred at reflux 2 hours in (70 ml) ethanol. The reaction was extracted with Na$_2$CO$_3$ solution/ethyl acetate, and after removing the solvent by evaporation, the residue was purified by chromatography (hexane/ethyl acetate, 6/4). The solvent was evaporated to obtain 120 mg (38%) of 9i as yellow solid.
NMR $^1$H (CDCl$_3$), δ=2.96 (6H, s); 3.81 (2H, sl); 6.72 (2H, d, J=9.2 Hz); 6.79 (1H, dd, J=2.0 Hz, J=9.0 Hz); 6.88 (1H, d, J=2.0Hz); 7.64 (1H, d, J=8.9 Hz); 8.03 (2H, d, J=9.0 Hz). NMR $^{13}$C (CDCl$_3$), δ=40.5 (2C); 96.7, 112.1 (2C); 118.6, 120.6, 121.2 (2C); 130.5, 140.4, 145.2, 146.1, 150.3.

N-((E)-3-(tributylstannyl)allyl)-2-(4-dimethylamino)phenyl)-2H-benzo[d][1,2,3]triazol-5-amine (9j)

Under N$_2$, to 90 mg (0.35 mmol) of 9i in (5 ml) THF was added 0.186 ml (1 mmol) of N,N-diisopropylethylamine and 535 mg (1 mmol) of a tin compound. The reaction was heated at 60° C. overnight, then water was added and extracted with ethyl acetate. After removing the solvent by evaporation, the residue was purified by chromatography (hexane/ethyl acetate/triethylamine, 22/2.5/0.5). The solvent was evaporated to obtain 48 mg (23%) of 9j as yellow oil.
NMR $^1$H (CDCl$_3$), δ=0.79 (9H, m); 1.01-1.41 (18H, m); 2.95 (6H, s); 3.82 (2H, m); 3.96 (1H, m); 6.06 (1H, d, J=15.2 Hz); 6.14 (1H, d, J=15.2 Hz); 6.72-6.80 (3H, m); 7.58-7.72 (2H, m); 8.03 (2H, d, J=9.2 Hz). NMR$^{13}$C (CDCl$_3$), δ=9.5 (3C); 13.7 (3C); 27.3 (3C); 29.1 (3C); 40.7 (2C); 48.7, 112.4 (2C); 118.3, 120.6, 121.2 (2C); 126.0, 127.4, 128.8, 129.3, 140.3, 143.6, 146.4, 150.0.

2-(4-(dimethylamino)phenyl)-N-((E)-3-iodoallyl)-2H-benzo[d][1,2,3]triazol-5-amine (9k)

Under N$_2$, to 40 mg (0.7 mmol) of 9j in (3 ml) CH$_2$Cl$_2$ was added at 0° C., 2 mg iodine in (0.5 ml) CH$_2$Cl$_2$. The reaction was stirred 15 min at room temperature and water was added, after extraction the solvent was evaporated. The residue was purified by chromatography (hexane/ethyl acetate, 8/2). The solvent was evaporated to obtain 11 mg (38%) of 9k as yellow solid.
NMR $^1$H (CDCl$_3$), δ=2.96 (6H, s); 3.75 (2H, m); 4.03 (1H, m); 6.33 (1H, d, J=14.5 Hz); 6.55 (1H, d, J=14.5 Hz); 6.66-6.73 (4H, m); 7.61 (1H, J=9.0 Hz); 8.02 (2H, d, J=9.2 Hz). NMR$^{13}$C (CDCl$_3$), δ=40.5 (2C); 48.4, 78.3, 92.7, 112.1 (2C); 118.6, 120.6, 121.2 (2C); 120.5, 140.1, 142.1, 146.0, 146.3, 150.3.

1-(2-amino-4 and-5-chlorophenyl)-2-(4-nitrophenyl)diazene (10a)

4-chloro-1,2-phenylenediamine (1.5 g, 1 eq), 4-nitronitrozoaniline (1.2 g, 1 eq) and NaOH (450 mg, 1 eq) were mixed neat and heated at 70° C. for 20 min with constant triturating. The resulting paste was extracted with toluene, concentrated in vacuum and purified by flash chromatography (SiO$_2$, hexane/AcOEt, 8/2) giving a mixture of two isomers (3 and 4 chloro) as a red solid in 21% yield.

1-(2-amino-4 and-5-iodophenyl)-2-(4-nitrophenyl)diazene (10b)

Using the same methodology as for 10a compound, 10b was obtained as a mixture of two isomers (3 and 4 nitro) as a red solid in 43% yield.

1-(2-amino-4 and-5-methoxyphenyl)-2-(4-nitrophenyl)diazene (10c)

Using the same methodology as for 10a, compound 10c was obtained as a mixture of two isomers (3 and 4 nitro) as a red solid in 6% yield.

1-(2-amino-4 and-5-iodophenyl)-2-(4-nitrophenyl)diazene (10d)

Using the same methodology as for 10a, compound 10d was obtained as a mixture of two isomers (3 and 4 nitro) as a red solid in 77% yield.

5-chloro-2-(4-nitrophenyl-2H-benzo[d][1,2,3]triazole (11a)

Under $N_2$, to 400 mg (1.4 mmol) of 10a in (10 ml) $CH_2Cl_2$ at 0° C. was slowly added 642 mg (1.4 mmol) of $Pb(OAc)_4$ solubilized in (2 ml) of $CH_2Cl_2$. The solution was stirred 20 min at room temperature and $Na_2CO_3$ solution was added. Organic layer was extracted and dried over $Na_2SO_4$. After removing the solvent by evaporation, the residue was purified by chromatography (hexane/ethyl acetate, 7/3). The solvent was evaporated to obtain 470 mg (38%) of 11a as pink solid.

NMR $^1H$ (CDCl$_3$), δ=7.34 (1H, dd, J=1.4 Hz, J=7.3 Hz); 7.82 (1H, d, J=7.3 Hz); 7.87 (1H, d, J=1.4 Hz); 8.36 (2H, d, J=7.3 Hz); 8.49 (2H, d, J=7.3 Hz). NMR $^{13}C$ (CDCl$_3$), δ=92.7, 116.3 (2C); 117.4, 119.4, 122.3 (2C); 127.3, 132.7, 141.3, 143.5, 146.7.

5-iodo-2-(4-nitrophenyl)-2H-benzo[d][1,2,3]triazole (11b)

Using the same methodology as for 11a, compound 11b was obtained as a red solid in 20% yield.

NMR $^1H$ (CDCl$_3$), δ=7.26 (1H, dd, J=1.5 Hz, J=7.2 Hz); 7.59 (1H, d, J=7.2 Hz); 7.76 (1H, d, J=1.5 Hz); 8.54 (2H, d, J=7.3 Hz); 8.63 (2H, d, J=7.3 Hz). NMR $^{13}C$ (CDCl$_3$), δ=92.4, 93.7, 118.2 (2C); 119.7, 122.4 (2C); 126.8, 134.3, 140.1, 142.5, 144.8.

5-methoxy-2-(4-nitrophenyl)-2H-benzo[d][1,2,3]triazole (11c)

Using the same methodology as for 11a, compound 11c was obtained as a yellow solid in 61% yield.

NMR $^1H$ (CDCl$_3$), δ=3.86 (3H, s); 7.02 (1H, d, J=2.0 Hz); 7.07 (1H, dd, J=2.0 Hz, J=9.3 Hz); 7.71 (1H, d, J=9.3 Hz) 8.33 (2H, d, J=7.6 Hz); 8.42 (2H, d, J=7.6 Hz). NMR $^{13}C$ (CDCl$_3$), δ=53.4, 92.1, 118.1 (2C); 121.6, 122.2, 122.9 (2C); 124.1, 140.1, 142.1, 144.6, 157.9.

5-nitro-2-(4-nitrophenyl)-2H-benzo[d][1,2,3]triazole (11d)

Using the same methodology as for 11a, compound 11c was obtained as a yellow solid in 75% yield.

NMR $^1H$ (CDCl$_3$), δ=7.76 (1H, dd, J=1.3 Hz, J=7.4 Hz); 7.89 (1H, d, J=7.4 Hz); 7.91 (1H, d, J=1.3 Hz); 8.41 (2H, d, J=7.4 Hz); 8.52 (2H, d, J=7.4 Hz). NMR $^{13}C$ (CDCl$_3$), δ=117.6, 118.3 (2C); 120.3, 122.6 (2C); 128.4, 131.6, 136.3, 147.6, 152.4, 155.3.

4-(5-chloro-2H-benzo[d][1,2,3]triazol-2-yl)benzenamine (12a)

Under $N_2$, 100 mg (0.4 mmol) of 11a with 330 mg (1.4 mmol) of tin(II) chloride was stirred at reflux 5 hours in (20 ml) ethanol. The reaction was extracted with $Na_2CO_3$ solution/ethyl acetate and after removing the solvent by evaporation, the residue was purified by chromatography (hexane/ethyl acetate, 7/3). The solvent was evaporated to obtain 56 mg (63%) 12a as white solid.

NMR $^1H$ (CDCl$_3$), δ=3.87 (2H, sl); 6.70 (2H, d, J=8.7 Hz); 7.52-7.59 (2H, m); 8.01 (2H, d, J=8.7 Hz); 8.24 (1H, s). NMR $^{13}C$ (CDCl$_3$), δ=115.1 (2C); 117.0, 119.2, 122.1 (2C); 128.0, 131.9, 132.2, 143.2 145.0, 147.6.

4-(5-iodo-2H-benzo[d][1,2,3]triazol-2-yl)benzenamine (12b)

Using the same methodology as for 12a, compound 12b was obtained as a yellow solid in 52% yield.

NMR $^1H$ (CDCl$_3$), δ=3.87 (2H, sl); 6.70 (2H, d, J=8.7 Hz); 7.52-7.59 (2H, m); 8.01 (2H, d, J=8.7 Hz); 8.24 (1H, s). NMR $^{13}C$ (CDCl$_3$), δ=91.3, 115.1 (2C); 119.5, 122.1 (2C); 127.1, 131.8, 135.3, 143.6, 146.2, 147.7.

4-(5-methoxy-2H-benzo[d][1,2,3]triazol-2-yl)benzenamine (12c)

Using the same methodology as for 12a, compound 12c was obtained as a yellow solid in 76% yield.

NMR $^1H$ (CDCl$_3$), δ=3.81 (2H, sl); 3.83 (3H, s); 6.73 (2H, d, J=8.9 Hz); 7.00 (1H, dd, J=2.3 Hz, J=9.2 Hz); 7.05 (1H, d, J=2.0z); 7.69 (1H, d, J=9.2 Hz); 7.99 (2H, d, J=8.9 Hz). NMR $^{13}C$(CDCl$_3$), δ=55.5, 94.7, 113.4, 115.1 (2C); 118.8, 121.5, 121.6(2C); 126.3, 145.6, 146.9, 158.9.

N,N-dimethyl-4-(5-trimethylstannyl)-2H-benzo[d][1,2,3]triazol-2-yl)benzenamine (14)

To a solution of 12 (100 mg, 1 eq) was added dropwise at −78° C. nBuLi (138 ml, 1.1 eq, 2.5M hexane) and the resulting mixture was stirred for 15 min at −78° C. Me$_3$SnCl (378 ml, 1.2 eq, 1M THF) was then added dropwise and the resulting solution was stirred for about 30 min at −78° C. and 1 h at RT before hydrolysis with 2 ml of $H_2O$. Extraction with 3×15 ml AcOEt and purification by flash chromatography (SiO$_2$, hexane/AcOEt, 9/1) giving 14 as a yellow solid in 13% yield.

NMR $^1H$ (CDCl$_3$); δ=0.28 (s, 9H, CH$_3$); 2.96 (s, 6H, CH$_3$); 6.72 (d, 2H, J=8.8 Hz, CHAr); 7.39 (d, 1H, J=8.4 Hz, CHAr); 7.80 (dd, 1H, J=8.4, 0.8 Hz, CHAr); 7.98 (s, 1H, CHAr); 8.12 (d, 2H, J=8.8 Hz, CHAr). NMR $^{13}C$ (CDCl$_3$); δ=−9.3 (3C, CH$_3$); 40.4 (2C, CH$_3$); 112.0 (2C, CHAr); 117.0 (1C, CHAr); 121.7 (2C, CHAr); 125.5 (1C, CHAr); 130.3 (1C, Cq); 132.5 (1C, CHAr); 140.8 (1C, Cq); 144.8 (1C, Cq); 144.9 (1C, Cq); 150.7 (1C, Cq).

Compound (15)

Using the same methodology as for 8 (starting from 4-iodoaniline), 15 was obtained as a red solid in 41% yield.

Exemplary compounds of the invention in series II

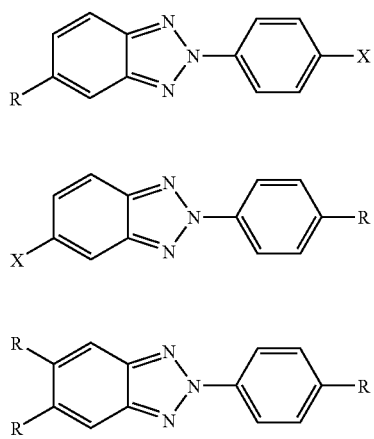

Series A

Series B

Series C

R = F, Cl, Br, I, OMe, SnMe3, SnBu3
X = NMe2, NHM2, NH2, NHSO2Me, OMe, OH,
HN⟶SnBu3  HN⟶I

EXAMPLE III

Series III Compounds of the Invention

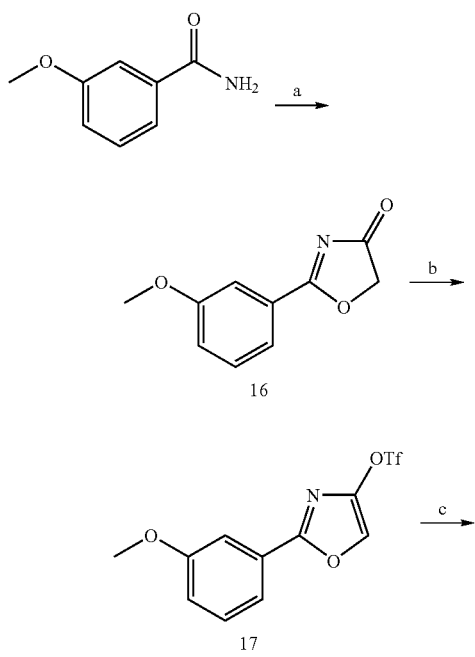

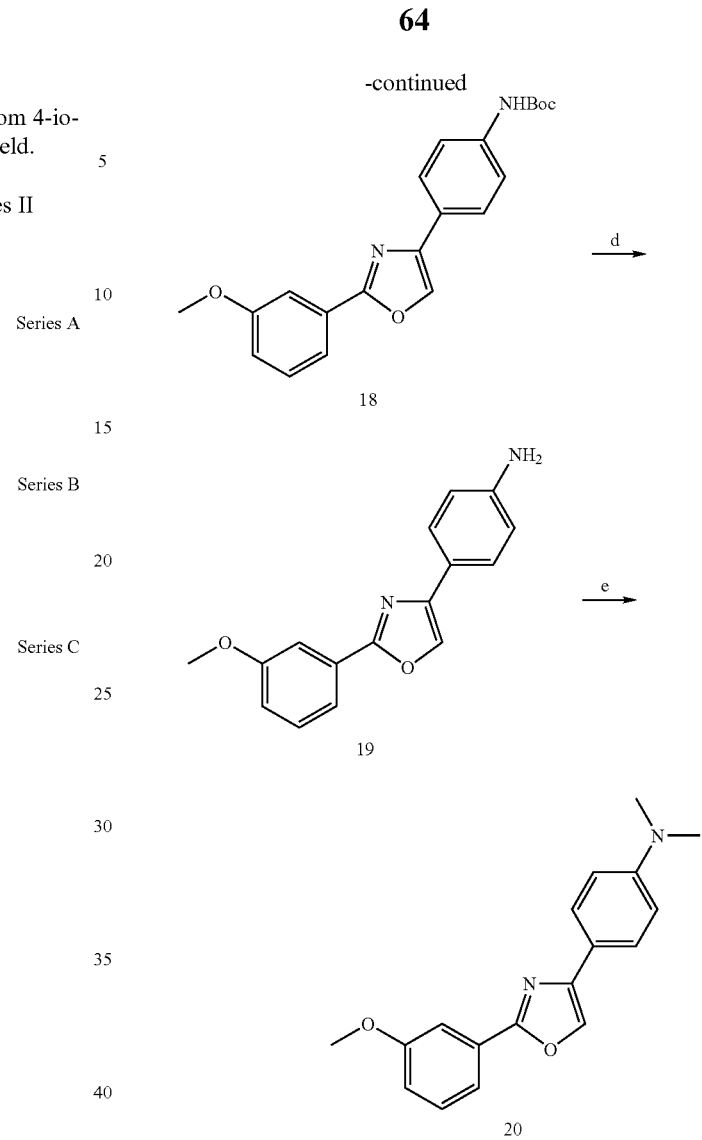

a ClCH$_2$COCl/NaH/DME,
b Tf$_2$O/2,6-lutidine/CH$_2$Cl$_2$,
c 4-NHBocPh-SnMe$_3$/Pd(PPh$_3$)4/LiCl/Dioxane,
d TFA/CH$_2$Cl$_2$ and
e CH$_3$I/K$_2$CO$_3$/DMF 2-(3-methoxyphenyl)oxazol-4(5H)-one (16)

2 g (1 eq) of 3-methoxybenzamide was mixed with 3.1 ml (2.7 eq) of chloroacethylchloride and the resulting mixture was heated at 110° C. for 1 h. After cooling, the resulting solid was recrystallized in CHCl$_3$. The resulting solid was added to a suspension of NaH (489 mg, 1.1 eq) in DME at 0° C. After 30 min, the resulting mixture was refluxed for 5 h, cooled to RT and hydrolyzed, extracted with AcOEt, washed with NaCl salt and dried. The resulting solid was recrystallized in a mixture hexane/AcOEt giving 16 as a white solid in 26% yield.

NMR $^1$H (CDCl$_3$), δ=3.85 (s, 3H, CH$_3$); 4.74 (s, 2H, CH$_2$); 7.22 (dd, 1H, J=8.0, 2.4 Hz, CHAr); 7.42 (t, 1H, J=8.0 Hz, CHAr); 7.69 (s, 1H, CHAr); 7.77 (d, 1H, J=8.0 Hz, CHAr). NMR $^{13}$C (CDCl$_3$), δ=55.9 (1C, CH$_3$); 70.2 (1C, CH$_2$); 114.4

2-(3-methoxyphenyl)oxazol-4-yl trifluoromethanesulfonate (17)

Compound 16 (516 mg, 1 eq) was dissolved in CH$_2$Cl$_2$. To the resulting solution, at 0° C., was added 501 µL (1.6 eq) of 2,6-lutidine, followed by the dropwise addition of Tf$_2$O (681 ml, 1.5 eq). The resulting mixture was stirred for 4 h at RT, then an additional 501 µL (1.6 eq) of 2,6-lutidine and 681 ml (1.5 eq) of Tf$_2$O were added. After 1 h, the mixture was evaporated and the residue purified by flash chromatography (SiO$_2$, CH$_2$Cl$_2$/hexane, 9/1) giving 17 as a red oil in 75% yield.

NMR $^1$H (CDCl$_3$), δ=3.69 (s, 3H, CH$_3$); 6.87 (dd, 1H, J=8.0, 2.5 Hz, CHAr); 7.19 (t, 1H, J=8.0 Hz, CHAr); 7.34 (t, 1H, J=2.5 Hz, CHAr); 7.42 (d, 1H, J=8.0 Hz, CHAr); 7.56 (s, 1H, CHAr). NMR $^{13}$C (CDCl$_3$), δ=55.7 (1C, CH$_3$); 111.6 (1C, CHAr); 118.2 (1C, CHAr); 119.3 (1C, CHAr); 127.6 (1C, Cq); 130.4 (1C, CHAr); 146.3 (1C, Cq); 159.9 (1C, Cq); 160.3 (1C, Cq).

tert-butyl 4-(2-(3-methoxyphenyl)oxazol-4-yl)phenylcarbamate (18)

In a sealable tube, 17 (436 mg, 1 eq), tert-butyl 4-(trimethylstannyl)phenylcarbamate (600 mg, 1.25 eq), LiCl (280 mg, 4 eq), Pd(PPh$_3$)$_4$ (77 mg, 5%) were mixed in 10 ml of dioxane. The tube was sealed and heated for 1 night at 100° C., cooled to RT, evaporated and purified by flash chromatography (SiO$_2$, hexane/AcOEt, 85/15) giving 18 as a white solid in 73% yield.

NMR $^1$H (CDCl$_3$), δ=1.45 (s, 9H, 3CH$_3$); 3.81 (s, 3H, CH$_3$); 6.54 (bs, 1H, NH); 6.93 (dd, 1H, J=8.0, 2.5 Hz, CHAr); 7.29 (t, 1H, J=8.0 Hz, CHAr); 7.35 (d, 2H, J=8.5 Hz, CHAr); 7.56 (s, 1H, CHAr); 7.61 (d, 1H, J=8.0 Hz, CHAr); 7.66 (d, 2H, J=8.5 Hz, CHAr); 7.81 (s, 1H, CHAr). NMR $^{13}$C (CDCl$_3$), δ=28.7 (3C, CH$_3$); 55.8 (1C, CH$_3$); 111.5 (1C, CHAr); 117.3 (1C, CHAr); 118.9 (1C, CHAr); 119.3 (2C, CHAr); 126.2 (1C, Cq); 126.7 (2C, CHAr); 129.0 (1C, Cq); 130.2 (1C, CHAr); 133.2 (1C, CHAr); 138.6 (1C, Cq); 142.0 (1C, Cq); 153.0 (1C, Cq); 160.2 (1C, Cq); 162.1 (1C, Cq).

4-(2-(3-methoxyphenyl)oxazol-4-yl)benzenamine (19)

In 10 ml of CH$_2$Cl$_2$ was dissolved 300 mg of compound 19. To the resulting solution, at 0° C., was added dropwise 1 ml of TFA. The resulting solution was stirred at RT for 3 h before the addition of an additional 1 ml of TFA. After 1 night, the mixture was hydrolyzed with NaHCO$_3$ salt, extracted with CH$_2$Cl$_2$ and purified by flash chromatography (SiO$_2$, hexane/AcOEt, 7/3) giving 19 as a white solid in 75% yield.

NMR $^1$H (CDCl$_3$), δ=3.79 (s, 3H, CH$_3$); 6.64 (d, 2H, J=8.4 Hz, CHAr); 6.91 (ddd, 1H, J=8.0, 2.8, 0.8 Hz, CHAr); 7.28 (t, 1H, J=8.0 Hz, CHAr); 7.53 (d, 2H, J=8.4 Hz, CHAr); 7.54-7.55 (m, 1H, CHAr); 7.60 (dt, 1H, J=7.6, 1.2 Hz, CHAr); 7.74 (s, 1H, CHAr). NMR$^{13}$C (CDCl$_3$), δ=55.8 (1C, CH$_3$); 111.4 (1C, CHAr); 115.5 (2C, CHAr); 117.0 (1C, CHAr); 119.2 (1C, CHAr); 121.7 (1C, Cq); 127.1 (2C, CHAr); 129.2 (1C, Cq); 130.2 (1C, CHAr); 132.2 (1C, Cq); 142.5 (1C, Cq); 146.9 (1C, Cq); 160.1 (1C, Cq); 161.7 (1C, Cq).

4-(2-(3-methoxyphenyl)oxazolyl-4)-N,N-dimethyl-benzenamine (20)

In DMF was dissolved 19 (217 mg, 1 eq). To the resulting solution, K$_2$CO$_3$ (450 mg, 4 eq) and CH$_3$I (203 µL, 4 eq) were added successively. The resulting mixture was stirred overnight, then hydrolyzed with H$_2$O, extracted with AcOEt and purified by flash chromatography (SiO$_2$, hexane/AcOEt, 8/2) giving 20 as a white solid in 79% yield.

NMR $^1$H (CDCl$_3$), δ=2.78 (s, 6H, 2CH$_3$); 3.69 (s, 3H, CH$_3$); 6.58 (d, 2H, J=8.5 Hz, CHAr); 6.80 (ddd, 1H, J=8.5, 2.5, 1.0 Hz, CHAr); 7.17 (t, 1H, J=8.0 Hz, CHAr); 7.45-7.46 (m, 1H, CHAr); 7.48-7.61 (m, 3H, CHAr); 7.62 (s, 1H, CHAr). NMR $^{13}$C (CDCl$_3$), δ=41.0 (2C, CH$_3$); 55.9 (1C, CH$_3$); 111.5 (1C, CHAr); 112.9 (2C, CHAr); 117.1 (1C, CHAr); 119.4 (1C, CHAr); 119.8 (1C, Cq); 127.1 (2C, CHAr); 129.4 (1C, Cq); 130.2 (1C, CHAr); 132.2 (1C, CHAr); 142.8 (1C, Cq); 150.8 (1C, Cq); 160.3 (1C, Cq); 161.9 (1C, Cq).

EXAMPLE IV

Series IV Compounds of the Invention

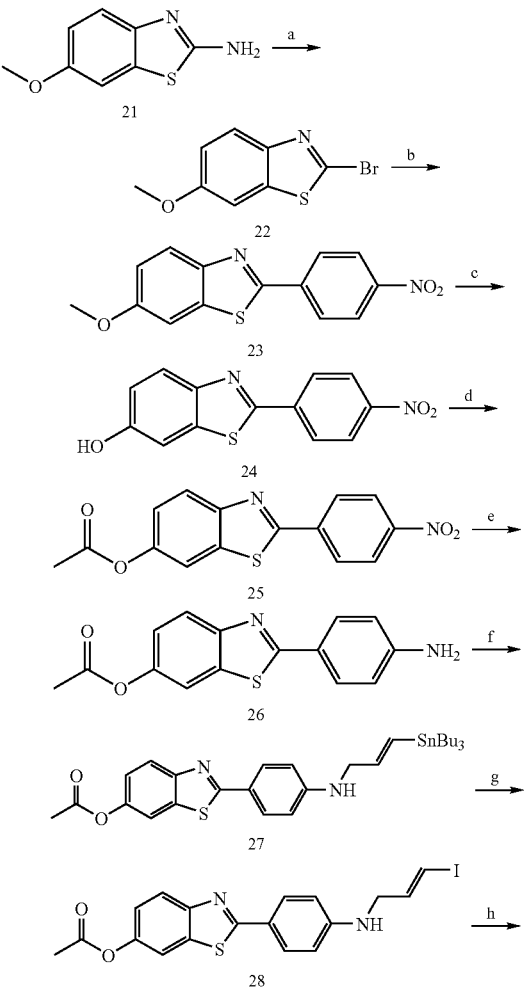

-continued

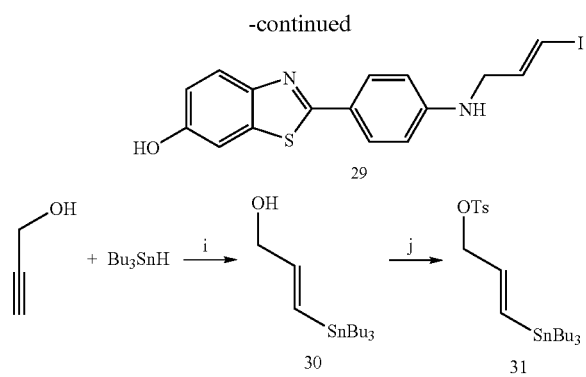

a isoamylnitrite/CuBr/PEG,
b 1-iodo-4-nitrobenzene/Cs₂CO₃/CuBr/Pd(OAc)₂/P(tBu)₄,
c BBr₃/CH₂Cl₂,
d NaH/AcCl,
e H₂/Pd/C,
f K₂CO₃/31/acetone,
g I₂/CHCl₃,
h NaOH 2N,
i Bu₃SnH/AIBN and
j Me₃SiOK/TsCl 2-bromo-6-methoxybenzo[d]thiazole (22)

Under $N_2$, to a solution of copper bromide (34.7 mmol), isoamylnitrite (52.1 mmol) and PEG (20 ml) were added a warm solution of 2-amino-6-methoxybenzothiazole (21, 0.35 mmol) in acetonitrile (150 ml) during about 30 min. The resulting mixture was stirred at room temperature for 2 h, then the reaction was hydrolyzed and extracted with ethyl acetate. The organic layer was dried over $Na_2SO_4$ and the solvent was removed via a rotary evaporator. The residue was purified by chromatography on silica gel using 90:10 hexane/ethyl acetate as the eluent to yield 4.83 g (57%) of 22 as a white solid.

NMR ¹H (CDCl₃), δ=3.59 (3H, s); 6.78 (1H, dd, J=2.8 Hz, J=9.6 Hz); 6.91 (1H, d, J=2.8 Hz); 7.57 (1H, d, J=9.6 Hz). NMR¹³C (CDCl₃), δ=55.2; 103.2; 115.4; 122.8; 134.9; 137.2; 146.4; 157.6.

6-methoxy-2-(4-nitrophenyl)benzo[d]thiazole (23)

Under $N_2$, in a sealed tube, to 22 (19.7 mmol) in DMF 50 ml, 1-iodo-4-nitrobenzene (21.6 mmol), cesium carbonate (19.6 mmol), palladium acetate (0.98 mmol), copper bromide (0.2 mmol) and tributylphosphine (1.9 mmol) were added. The reaction was stirred at 150° C. overnight and, after cooling to room temperature, the mixture was extracted with ethyl acetate. The organic layer was then washed (3 times) with water, dried over $Na_2SO_4$ and the solvent removed via a rotary evaporator. The residue was purified by chromatography on silica gel using 9:1 hexane/ethyl acetate as the eluent to yield 4.62 g (81%) of 23 as a yellow solid.

NMR ¹H (DMSO), δ=3.83 (3H, s); 7.21 (1H, J=8.6 Hz); 7.73 (s, 1 H); 8.04 (2H, d, J=8.7 Hz); 8.25 (1H, d, J=8.6 Hz); 8.35 (2H, d, J=8.7 Hz). NMR ¹³C(DMSO), δ=55.3; 104.7; 115.7; 1 16.7; 123.4; 124.1 (2C); 124.5; 127.8; 128.6 (2C); 144.0; 147.5; 157.5.

2-(4-nitrophenyl)benzo[d]thiazol-6-ol (24)

Under $N_2$, 23 (10.4 mmol) was dissolved in $CH_2Cl_2$ and, at −40° C., BBr₃ (31.4 mmol) was slowly added. The mixture was then stirred 24 hours at room temperature. The reaction mixture was quenched with water and extracted with ethyl acetate (×3 100 ml). The organic layers were combined, dried over $Na_2SO_4$ and the solvent was removed via a rotary evaporator. The residue was purified by chromatography on silica gel using 7:3 hexane/ethyl acetate as the eluent to yield 1.53 g (53%) of 24 as a yellow solid.

NMR ¹H (DMSO), δ=7.06 (1H, dd, J=2.4 Hz, J=8.8 Hz); 7.47 (1H, d, J=2.4 Hz); 7.93 (1H, d, J=8.8 Hz); 8.23 (2H, d, J=8.8 Hz); 8.34 (2H, d, J=8.8 Hz); 10.07 (1H, sl). NMR ¹³C (DMSO), δ=106.9; 115.9; 117.0; 124.6 (2C); 127.8 (2C); 136.9; 138.8; 147.3; 148.3; 156.7; 160.9.

2-(4-nitrophenyl)benzo[d]thiazol-6-yl acetate (25)

Under N2, 24 (4.0 mmol) was dissolved in THF (100 ml) and, at 0° C., NaH (8.2 mmol) was slowly added. The mixture was stirred for 30 min at 0° C. and acetyl chloride (6.0 mmol) was added dropwise. The resulting mixture was then stirred at room temperature overnight. The reaction was hydrolyzed and extracted with ethyl acetate. The organic layer was dried over $Na_2SO_4$ and the solvent was removed via a rotary evaporator. The residue was purified by chromatography on silica gel using 7:3 hexane/ethyl acetate as the eluent to yield 1.24 g (74%) of 25 as a yellow solid.

NMR ¹H (CDCl₃), δ=2.29 (3H, s), 7.20 (1H, dd, J=2.2 Hz, J=8.7 Hz), 7.65 1H, d, J=2.2 Hz,), 8.02 (1H, d, J=8.7 Hz), 8.16 (2H, d, J=8.8 Hz), 8.27 (2H, d, J=8.8 Hz). NMR ¹³C (CDCl₃), δ=21.5, 115.2, 121.8, 124.7(2C), 124.8, 128.6(2C), 136.5, 139.3, 149.2, 149.5, 152.3, 159.9, 169.7.

2-(4-aminophenyl)benzo[d]thiazol-6-yl acetate (26)

Under $H_2$, 25 (2.7 mmol) was dissolved in a mixture of THF/MeOH (5/20 ml) and was then hydrogenated at room temperature for 1 h under 30 PSI. Pd (c) was filtered and the solvent removed via a rotary evaporator. The residue was purified by chromatography on silica gel using 7:3 hexane/ethyl acetate as the eluent to yield 560 mg (71%) of 26 as a white solid.

NMR ¹H (CDCl₃), δ=2.23 (3H, s); 4.01 (2H, sl); 6.72 (2H, d, J=8.7 Hz,); 7.16 (1H, dd, J=2.2 Hz, J=8.8 Hz); 7.59 (1H, d, J=2.1 Hz ); 7.86 (2H, d, J=8.7 Hz); 7.95 (1H, d, J=8.8 Hz ). NMR ¹³C (CDCl₃), δ=21.3, 114.4, 114.9 (2C); 120.5; 123.0; 123.9; 127.4; 129.3 (2C); 135.4; 147.6; 149.5; 152.3; 164.8.

2-(4-((E-3-tributylstannyl)allylamino)phenyl)benzo[d]thazol-6-yl acetate (27)

Under $N_2$, to 26 (0.35 mmol) in acetone (5 ml), $K_2CO_3$ (1 mmol) was slowly added at 0° C. The reaction was stirred for 30 min with 31 (0.5 mmol) in 2 ml of acetone added. The resulting mixture was stirred at reflux overnight. The reaction was cooled at room temperature and acetone was removed in vacuo. Water was then added and the resulting reaction was extracted with ethyl acetate. The organic layer was dried over $Na_2SO_4$ and the solvent was removed via a rotary evaporator. The residue was purified by chromatography on silica gel using 65:20:15 hexane/diethyl ether/triethylamine as the eluent to yield 105 mg (49%) of 27 as a white solid.

NMR ¹H (CDCl₃), δ=0.75-0.83 (15H, m); 1.17-1.27 (6H, m); 1.32-1.44 (6H, m); 2.26 (3H, s); 3.81 (2H, m); 4.22 (1H, sl); 5.98 (1H, dt, J=4.8 Hz, J=9.5 Hz); 6.16 (1H, d, J=19 Hz); 6.57 (2H, d, J=8.8 Hz); 7.07 (1H, dd, J=2.4 Hz, J=8.6 Hz); 7.51 (1H, d, J=1.5 Hz); 7.79 (2H, d, J=8.8 Hz); 7.86 (1H, d, J=8.8 Hz). NMR ¹³C (CDCl₃), δ=9.6 (3c); 13.9 (3C); 21.4; 27.4 (3C); 29.2(3C); 49.1; 112.8 (2C); 114.4; 120.4; 122.5; 122.8; 129.2 (2C); 130.6; 135.3; 143.9; 147.5; 150.8; 152.5; 169.3; 169.9.

2-(4-((E-3-iodoallylamino)phenyl)benzo[d]thiazol-6-yl acetate (28)

Under $N_2$, to 27 (0.11 mmol) in $CHCl_3$ (3 ml), at 0° C., $I_2$ (1.25 mmol) in 1 ml of $CHCl_3$ was slowly added. The reaction was stirred for 45 min at room temperature and the mixture was extracted with a solution of 10% of $Na_2S_2O_3$ in water. The organic layer was dried over $Na_2SO_4$ and the solvent was removed via a rotary evaporator. The residue was purified by chromatography on silica gel using 60:40 hexane/ethyl acetate as the eluent to yield 51 mg (96%) of 28 as a white solid.

NMR $^1$H ($CDCl_3$), δ=2.34 (3H, s); 3.81-3.83 (2H, m); 4.26 (1H, sl); 6.37 (1H, d, J=14.5 Hz); 6.62-6.65 (2H, d, J=8.8 Hz); 6.98 (1H, s); 7.15 (1H, dd, J=2 Hz, J=8.8 Hz); 7.59 (1H, d, J=2 Hz); 7.88 (2H, d, J=8.8 Hz); 7.64 (1H, d, J=8.5 Hz). NMR $^{13}$C ($CDCl_3$), δ=21.4; 48.0; 78.5; 112.9(2C); 114.5; 120.5; 122.7; 123.0; 125.7; 129.4(2C); 136.0; 142.2; 149.9; 151.8; 152.8; 169.8.

2-(4-((E-3-iodoallylamino)phenyl)benzo[d]thiazol-6-ol (29)

28 was stirred at 80° C. for 1.5 h with NaOH 2M. After cooling at room temperature, the reaction was acidified with HCl 1N (Ph=7-8) and the aqueous layer extracted with ethyl acetate (×2). The organic layer was dried over $Na_2SO_4$ and the solvent was removed via a rotary evaporator. The residue was purified by chromatography on silica gel using 70:30 hexane/ethyl acetate as the eluent to yield 29 mg (81%) of 29 as a white solid.

NMR $^1$H (MeOH), δ=3.80 (2H, dd, J=5.2 Hz, J=1.5 Hz); 6.42 (1H, dt, J=5 Hz, J=15 Hz); 6.61-6.67 (1H, m); 6.69 (2H, d, J=8.5 Hz); 6.94 (1H, dd, J=2.5 Hz, J=9 Hz); 7.26 (1H, d, J=2.5 Hz); 7.69 (1H, d, J=8.5 Hz); 7.77 (2H, d, J=8.5 Hz). NMR $^{13}$C (MeOH), δ=54.6, 77.4, 107.4, 113.4 (2C); 116.6, 122.9, 123.0, 129.5 (2C); 136.6, 144.2, 148.6, 152.0, 156.4, 167.9.

(E-3-tributylstannyl)prop-2-en-1-ol (30)

Under $N_2$, to propargylic alcohol (51.5 mmol) at room temperature, tributyltin hydride (67.2 mmol) then AIBN (2.6 mmol) were added. The mixture was heated for 2 h at 80° C. After cooling at room temperature, the residue was purified by chromatography on silica gel using 95:5 hexane/ethyl acetate as the eluent to yield 4.65 g (26%) of 30 as a colorless oil.

NMR $^1$H ($CDCl_3$), δ=0.75-0.98 (15H, m); 1.20-1.34 (6H, m); 1.40-1.60 (6H, m); 2.03-2.15 (1H, m); 4.10-4.14 (2H, m); 6.13-6.15 (2H, m). NMR $^{13}$C ($CDCl_3$), δ=9.4 (3C); 13.7 (3C); 27.3 (3C); 29.1 (3C) 66.3; 128.2; 147.1.

(E)-3-(tributylstannyl)allyl 4-methylbenzenesulfonate (31)

Under $N_2$, to 30 (2.9 mmol) in ether (50 ml), at −25° C., potassium trimethylsilanolate was added. After stirring for 30 min, p-toluenesulfonyl chloride in ether (10 ml) was added dropwise. The resulting mixture was stirred for 2 h at −25° C. After hydrolyzing, the reaction was extracted with ethyl acetate and the organic layer was dried over $Na_2SO_4$. The solvent was also removed via a rotary evaporator. The residue was purified by chromatography on silica gel using 95:2.5:2.5 hexane/ethyl acetate/triethylamine as the eluent to yield 650 mg (45%) of 31 as a colorless oil.

NMR $^1$H ($CDCl_3$), δ=0.73-0.78 (15H, m); 1.15-1.21 (6H, m); 1.31-1.36 (6H, m); 2.33 (3H, s); 4.42 (2H, m); 5.80 (1H, dt, J=5 Hz, J=19 Hz); 6.18 (1H, d, J=19 Hz); 7.22 (2H, d, J=8 Hz); 7.68 (2H, d, J=8 Hz). NMR$^{13}$C ($CDCl_3$), δ=9.8 (3C); 14.0 (3C); 22.6; 27.6 (3C); 29.4 (3C); 73.7; 128.3 (2C); 130.2 (2C); 136.8; 138.1; 139.4; 145.0.

EXAMPLE V

Radioiodination as synthesis of 4-(5-[$^{123}$I]-2H-benzo[d][1,2,3]triazol-2-yl)-N,N-dimethylbenzenamine (13)

A sterile, pyrogen-free solution of no-carrier-added $^{123}$I-13 in physiological saline is prepared by reacting a trimethylstannyl precursor such as 14 with sodium [$^{123}$I]iodide in the presence of an oxidizing agent, for example, peracetic acid followed by HPLC isolation. The resulting radiolabeled product is purified by means of HPLC and formulated. To a shipping vial with dry Na[$^{123}$I]I/NaOH are added, in the following order, 50% aqueous MeOH, 0.8M $H_3PO_4$ in the amount just enough to neutralize the NaOH plus extra 10 μl, a solution of 14 (100 μg, 0.19 μmol) in 50 μl of MeOH and 50 μL of 6.4% aqueous peracetic acid freshly prepared by a 5-fold dilution of 32% $CH_3C(O)OOH$. The total volume of added reagents is 320 μL. After standing for 14-16 min at room temperature, the reaction mixture in the vial is quenched by the addition of 100 μl of a 100 mg/ml solution of $Na_2S_2O_5$ in saturated aqueous $NaHCO_3$ and the vial headspace is flushed with 60 ml of air into a charcoal filter. The vial is emptied and rinsed with 0.3-0.4 ml of 85% aqueous MeCN. The rinse is combined with the quenched reaction mixture and the resultant liquid is injected onto a reverse-phase HPLC column. The column (C18, 10μ, 4.6×250 mm) is eluted with a mixture of acetonitrile, water and triethylamine (60:40:0.2 v/v) at a flow rate of 1.0 ml/min. The fraction eluting at the retention time of the authentic 13 is collected into a 50 ml flask containing 50 μl of 34 mM L-ascorbic acid (stabilizer). The solvent is removed via a rotary evaporator at 45-50° C. under reduced pressure/argon gas flow. The dry residue in the flask is dissolved in 800 μl of 50% ethanol and the resulting solution is filtered through a 0.2 μm sterilizing filter into an empty sterile vial. The formulation is finalized by the addition of 6-8 ml of sterile 0.9% NaCl for injection through the same filter. Quality control testing includes visual inspection, determination of specific concentration, identity and radiochemical purity (by HPLC), pH, pyrogenicity and sterility (by compendial tests, USP XXII, 1990). All tests, including inoculation in two media for sterility, are performed before release for administration to subjects. Sterility is confirmed after 1 and 2 weeks of incubation at 37° C. The invention also contemplates other conventional methods known to those of ordinary skill in the art for preparing an amyloid probe from a compound of the invention. Ellis et al., *Aust. J. Chem.*, 26: 907 (1973); Wilson et al., *J. Org. Chem.*, 51: 4833 (1986); Wilbur et al., *J. Label. Compound Radiopharm.*, 19: 1171 (1982); Chumpradit et al., *J. Med Chem.*, 34: 877 (1991); Chumpradit et al., *J. Med Chem.*, 32: 1431 (1989); Kabalka et al., *J. Label. Compound Radiopharm.*, 19: 795 (1982); Koch et al., *Chem. Ber.*, 124: 2091 (1991); H. Mach et al., *J. Med Chem.*, 36: 3707 (1993); Arora et al., *J. Med Chem.*, 30: 918 (1987).

EXAMPLE VI

Binding Assays using Human AD Brain Tissues by Quantitative Autoradiography

Postmortem human cerebral cortical tissue from the frontal lobe was obtained from the Center for Neurodegenerative Disease at Emory University (Atlanta, Ga.). Fresh-frozen tissue sections were cut at a thickness of 20-25 μm and thaw-mounted onto gelatin-coated glass slides. The sections were then air-dried and stored at −80° C. until used. Prepared sections were thawed and incubated at room temperature in 0.05M Tris-HCl buffer, pH 7.7 with 10% ethanol containing 0.02 nM [$^{125}$I]-IMPY (a conventional amyloid ligand) having the structure

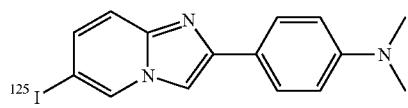

Figure 4:
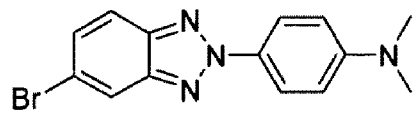
FIG. 4 includes experimental IC50 binding data for several exemplary compounds of the invention, which can be modified to comprise one or more amyloid probes that can be useful for in vivo imaging of amyloid and/or amyloid deposits.
Figure 4:
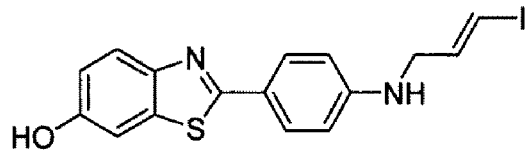
Figure 4:
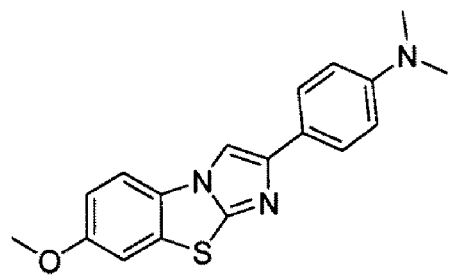
Figure 4:
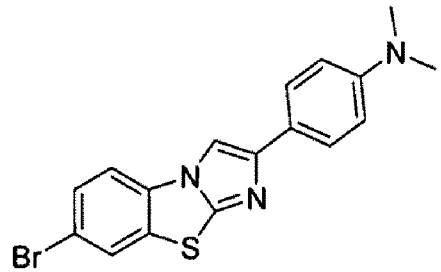
Figure 4:
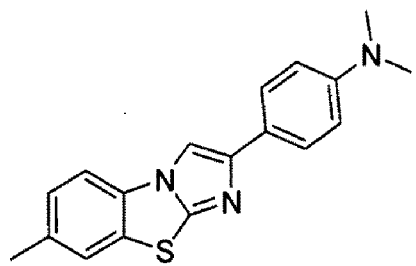
Figure 4:
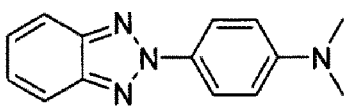
Figure 4:
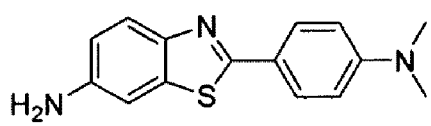
Figure 5:
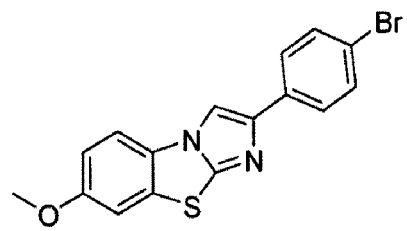
FIG. 5 includes experimental IC50 binding data for several exemplary compounds of the invention, which can be modified to comprise one or more amyloid probes that can be useful for in vivo imaging of amyloid and/or amyloid deposits.
Figure 5:
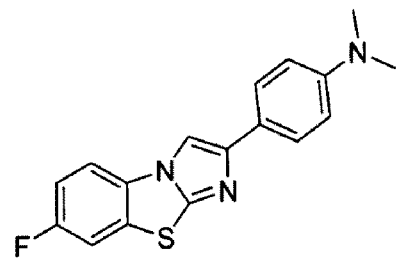
Figure 5:
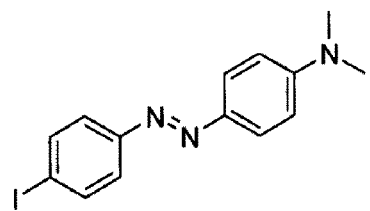
Figure 5:
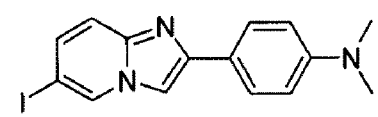
Figure 5:
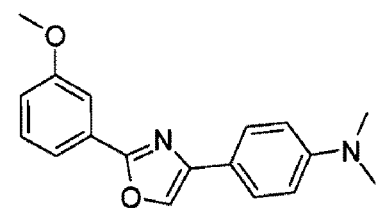
Figure 5:
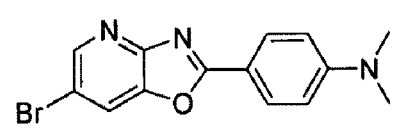
Figure 5:
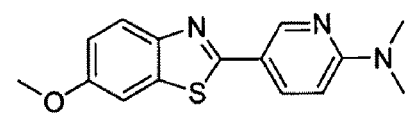
Figure 5:
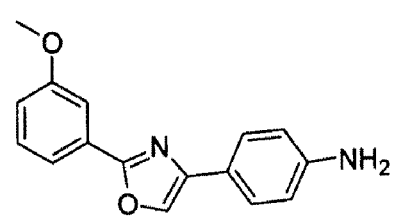

The radioligand was displaced with increasing concentrations (0.1 nm-5 μM) of cold inhibitor (in 200 μl of 100% ethanol). Nonspecific binding was determined in the presence of 5 μM thioflavin-T (THFT). Borosilicate glass tubes were used for the incubation containers to minimize hydrophobic adsorption to the walls. After 5 h, the sections were washed with 100% ethanol for 30 min at room temperature and allowed to air dry. The radiolabeled sections and $^{14}$C-plastic standards (calibrated for $^{125}$I, American Radiolabeled Chemicals, Inc., St Louis, Mo.) were apposed to autoradiograhphic film (Biomax MS, Eastman Kodak, Rochester, N.Y.) for 24 h. The resulting autoradiograms were digitized using an Epson 1680 Scanner with transparency unit and analyzed densitometrically with AIS software (Imaging Research, St. Catherines, Ontario) to determine binding density. Binding curves and corresponding $K_i$ or $K_d$ values can also generated using non-linear regression with GraphPad Prism software. IC50 binding data for compounds of the invention based on this binding assay are shown in FIGS. 4 and 5.

EXAMPLE VII

Developing SPECT Imaging Agents to Quantify Amyloid and/or Amyloid Deposits (Plaque) Burden in Alzheimer Disease Patients.

In one aspect, recent interest in AD therapy with drugs targeting reduction of β-amyloid burden such as, for example, the compounds of the invention, has underscored the need for non-invasive scintigraphic methods for interrogating amyloid deposition for both drug development and elucidating pathophysiological changes in AD patients. The present invention synthesized and radiolabeled a series of ligands with iodine-123 and iodine-125, although any labels, markers or tags as described herein can be used.

Compounds of the invention represented by MNI-187 and MNI-195 (Chart 1), were synthesized, their affinities for the β-amyloid protein were evaluated using human AD brain tissue and compared to that of IMPY, a conventional amyloid ligand. The compounds of the invention demonstrated binding affinities 2 to 10-fold better than that of IMPY.

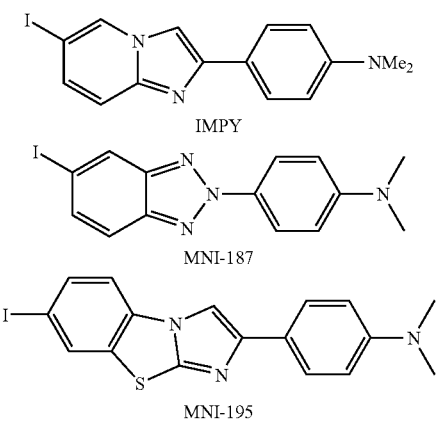

Chart 1

The labeling of the compounds of the invention was carried out under standard conditions (Na$^{123/125}$I, oxidizer, acidic medium) at ambient temperature. Radiochemical yields averaged 35-90%. The labeled compounds were readily purified by reverse-phase HPLC, and their radiochemical purity exceeded 95%. Lipophilicity and protein binding of the obtained amyloid probes of the invention (for example, for SPECT imaging) are comparable to those conventionally used in humans (for example, for MNI-187, LogD at pH 7.4 was 2.7, and the free ligand fraction in plasma was 4%).

The compounds or amyloid probes of the invention including those in Chart 1 and probes thereof can be used therapeutically or in subject scintigraphic imaging.

EXAMPLE VIII

Series I Compounds of the Invention

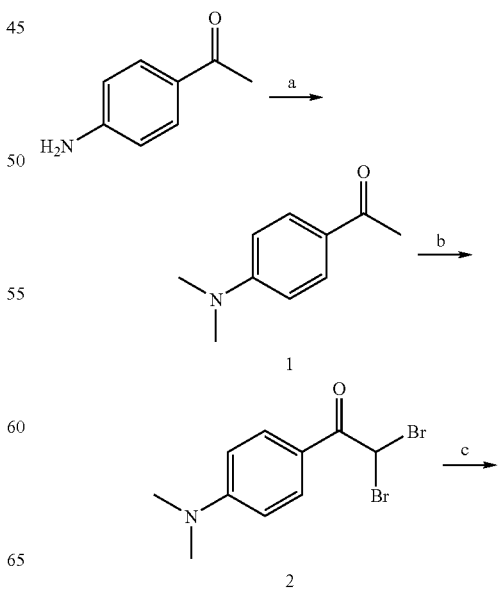

-continued

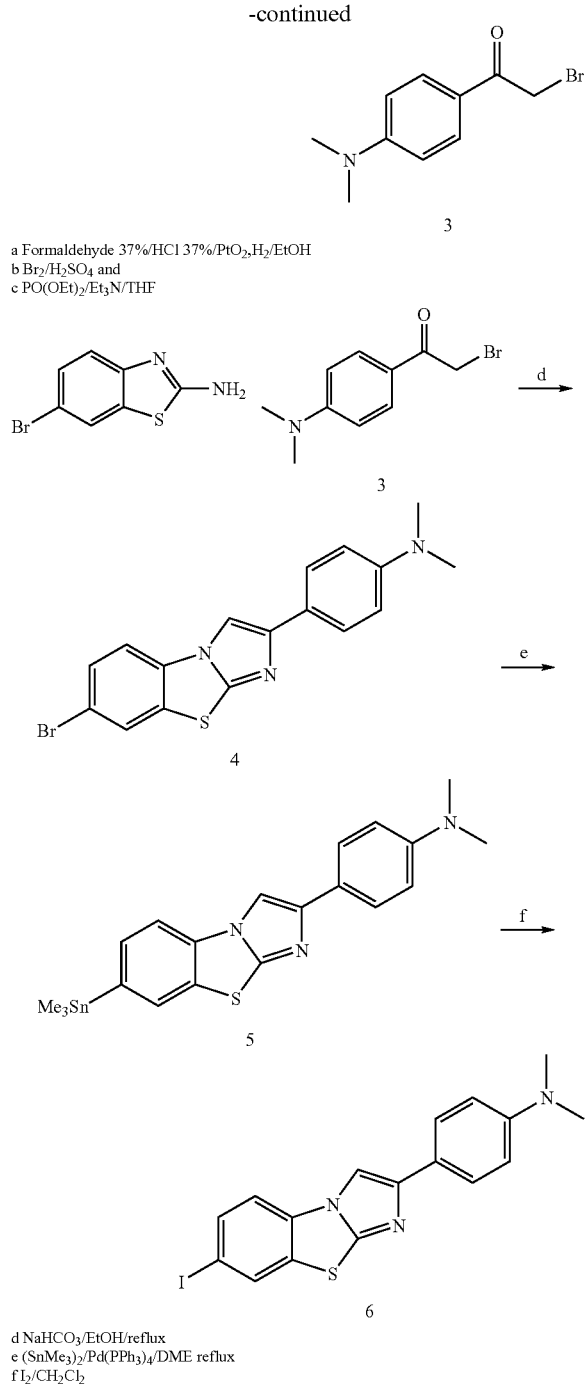

a Formaldehyde 37%/HCl 37%/PtO₂,H₂/EtOH
b Br₂/H₂SO₄ and
c PO(OEt)₂/Et₃N/THF d NaHCO₃/EtOH/reflux
e (SnMe₃)₂/Pd(PPh₃)₄/DME reflux
f I₂/CH₂Cl₂

4'-dimethylaminoacetophenone (1)

In a mixture EtOH/HCl 37% 80 ml/5 ml was dissolved 4'-aminoacetophenone (13.5 g, 0.1 mol), then formaldehyde 37% (15 ml) was added followed by PtO₂ (150 mg). The resulting solution was hydrogenated at 50PSI for 1 h, filtered through celite, evaporated and purified by flash chromatography (SiO₂, hexane/AcOEt, 8/2) giving 1 as a white solid in 62% yield.

NMR $^1$H (CDCl₃), δ=2.30 (s, 3H, CH₃); 2.85 (s, 6H, 2CH₃); 6.44 (d, 2H, J=9.0 Hz, 2CHAr); 7.67 (d, 2H, J=9.0 Hz, 2CHAr). NMR $^{13}$C (CDCl₃), δ=26.3 (1C, CH₃); 40.4 (2C, 2CH₃); 110.9 (2C, CHAr); 125.6 (1C, Cq); 130.9 (2C, CHAr); 153.7 (1C, Cq); 196.7 (1C, Cq).

2,2-dibromo-4'-dimethylaminoacetophenone (2)

In 20 ml of concentrated H₂SO₄ was dissolved 1 (3.8 g, 1 eq), then at 0° C. bromine (1.19 ml, 1 eq) was added dropwise and the resulting mixture was stirred at RT for 6 h before being poured into 200 ml of ice/H₂O. The resulting precipitate was collected by filtration, washed with H₂O, dissolved in CH₂Cl₂, dried over Na₂SO₄ and concentrated in vacuum to give 2 as a green solid in 68% yield, which can be directly used in the next step without any purification.

2-bromo-4'-dimethylacetophenone (3)

In 30 ml of THF was dissolved 2 (5.1 g, 1 eq), then at 0° C. was added dropwise a mixture of diethylphosphite (2.04 ml, 1 eq) and Et₃N (2.4 ml, 1.1 eq) in 12 ml of THF. The resulting mixture was stirred 6 h at RT, then evaporated and poured into 200 ml of ice/H₂O and the resulting precipitated was filtered, washed with H₂O and dried in vacuum. 3 was obtained as a green solid in 89% yield.

NMR $^1$H (CDCl₃), δ=2.97 (s, 6H, 2CH₃); 4.45 (s, 2H, CH₂); 6.57 (d, 2H, J=9.0 Hz, 2CHAr); 7.72 (d, 2H, CHAr). NMR $^{13}$C (CDCl₃), δ=31.3 (1C, CH₂); 40.4 (2C, CH₃); 111.1 (2C, CHAr); 121.8 (1C, Cq); 131.6 (2C, CHAr); 154.1 (1C, Cq); 189.7 (1C, Cq).

7-bromo-2-(4-dimethylaminophenyl)-imidazo[2,1-b]benzothiazole (4)

In the minimum volume of EtOH was dissolved commercially available 2-amino-6-bromobenzothiazole (2 mmol), then 3 (2 mmol) was added and the resulting mixture was refluxed for 2 h before addition of NaHCO₃ (3 mmol). After 6 h more of reflux, the mixture was hydrolyzed with H₂O (5 ml), extracted using AcOEt (4×25 ml), dried over Na₂SO₄, concentrated in vacuum and purified by flash chromatography (SiO₂, hexane/AcOEt, 1/1). p NMR $^1$H (DMSO d), δ=2.93 (s, 6H, 2CH₃); 6.77 (d, 2H, J=8.5 Hz, 2CHAr); 7.67 (d, 2H, J=8.5 Hz, 2CHAr); 7.71 (d, 1H, J=8.5 Hz, CHAr); 7.88 (d, 1H, J=8.5 Hz, CHAr); 8.29 (s, 1H, CHAr); 8.50 (s, 1H, CHAr). NMR $^{13}$C (DMSO-d₆), δ=40.4 (2C, CH₃); 107.2 (1C, CHAr); 112.6 (2C, CHAr); 114.9 (1C, CHAr); 116.6 (1C, Cq); 122.1 (1C, Cq); 126.0 (2C, CHAr); 127.6 (1C, CHAr); 129.7 (1C, CHAr); 131.5 (1C, Cq); 146.8 (1C, Cq); 147.7 (1C, Cq); 150.1 (1C, Cq). HRMS Calcd for C₁₇H₁₅N₃BrS: 372.0170, found: 372.0171. Anal. Calcd for C₁₇H₁₄N₃BrS: C, 54.85%; H, 3.79%; N, 11.29%; found: C, 54.49%; H, 3.73%; N, 11.06%.

7-trimethylstannyl)-2-(4-dimethylaminophenyl)-imidazo[2,1-b]benzothiazole (5)

To a solution of 4 (200 mg, 1 eq) in DME (5 ml) was added hexamethylditin (527 mg, 3 eq) and Pd(PPh₃)₄ (61 mg, 10%) and the resulting mixture was refluxed for 6 h. After cooling to RT, 20 ml of AcOEt were added and the mixture washed twice with 5 ml of H₂O, purified by flash chromatography (SiO₂, hexane/AcOEt/Et₃N, 9/1/0.1) to give 5 as a yellow oil in 35% yield.

NMR $^1$H (CDCl₃), δ=0.16 (s, 9H, CH₃); 2.79 (s, 6H, CH₃); 6.60 (d, 2H, J=8.8 Hz, CHAr); 7.30-7.36 (m, 2H, CHAr); 7.55-7.58 (m, 2H, CHAr); 7.64 (s, 1H, CHAr). NMR $^{13}$C (CDCl₃), δ=-9.1 (3C, CH₃); 40.6 (2C, CH₃); 105.0 (1C, Cq);

112.2 (1C, Cq); 112.7 (2C, CHAr); 122.4 (1C, Cq); 126.1 (2C, CHAr); 130.3 (1C, CHAr); 131.1 (1C, Cq); 132.3 (1C, Cq); 133.0 (1C, Cq); 138.4 (1C, CHAr); 147.5 (1C, Cq); 148.0 (1C, CHAr); 149.9 (1C, CHAr).

7-iodo-2-(4-dimethylaminophenyl)-imidazo[2,1-b]benzothiazole (6)

5 (64 mg, 1 eq) was dissolved in $CH_2Cl_2$ (5 ml) and to that was added dropwise $I_2$ (39 mg, 1.1 eq) in 2 ml of $CH_2Cl_2$, the resulting mixture was stirred at RT for 1 h before hydrolysis with 5 ml of $Na_2S_2O_3$ 10%. Extraction was performed using $CH_2Cl_2$ (2×5 ml) with drying over $Na_2SO_4$ and concentrating was carried out in vacuum. Purification by flash chromatography ($SiO_2$, hexane/AcOEt, 9/1) was used to give 6 as a white solid in 15% yield.

NMR $^1$H (CDCl$_3$); δ=3.02 (s, 6H, 2CH$_3$); 6.35(d, 1H, J=8.4 Hz, CHAr); 7.20 (s, 1H, 2CHAr); 7.36 (dd, 1H, J=8.8, 2.0 Hz, CHAr); 7.50 (d, 2H, J=8.0 Hz, CHAr); 7.71 (d, 1H, J=8.0 Hz, CHAr); 7.99 (s, 1H, CHAr).

EXAMPLE IX

Series II Compounds of the Invention

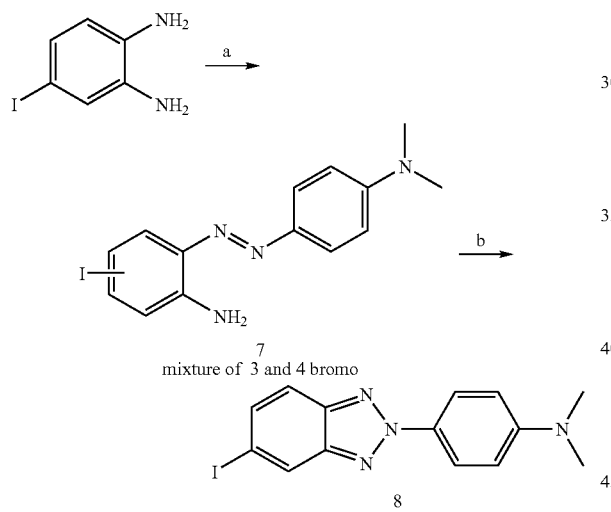

a 4-dimethylaminonitrozoaniline/NaOH/neat/70° C.,
b Pb(OAc)$_4$/CH$_2$Cl$_2$

1-(2-amino-4 and-5-iodophenyl)-2-(4-dimethylaminophenyl)diazene (7)

4-iodo-1,2-phenylenediamine (2 g, 1 eq), 4-dimethylaminonitrozoaniline (1.26 g, 1 eq) and NaOH (340 mg, 1 eq) were mixed neat and heated at 70° C. for 20 min with constant triturating. The resulting paste was extracted with toluene, concentrated in vacuum and purified by flash chromatography (SiO$_2$, hexane/AcOEt, 8/2) giving a mixture of two isomers (3 and 4 iodo) as a red solid in 32% yield.

4-(5-iodo-2H-benzo[d][1,2,3]triazol-2-yl)-N,N-dimethylbenzenamine (8)

In CH$_2$Cl$_2$ was dissolved 7 (1 g, 1 eq) and a solution of Pb(OAc)$_4$ (2.03 g, 1.1 eq) in which CH$_2$Cl$_2$ was added dropwise. The resulting solution was stirred 30 min at RT, then hydrolyzed with 15 ml of Na$_2$CO$_3$ salt, extracted with CH$_2$Cl$_2$, dried by Na$_2$SO$_4$, evaporated, purified by flash chromatography (SiO$_2$, hexane/AcOEt, 8/2) giving 11 as an orange solid in 10% yield.

NMR $^1$H (CDCl$_3$), δ=2.95 (s, 6H, 2CH$_3$); 6.68 (dd, 2H, J=8.8, 2.0 Hz, CHAr); 7.51 (dd, 1H, J=8.8, 2.0 Hz, CHAr); 7.56 (dd, J=8.8, 0.4 Hz, CHAr); 8.06 (dd, 2H, J=8.8, 2.0 Hz, CHAr); 8.22 (s, 1H, CHAr). NMR $^{13}$C (CDCl$_3$), δ=40.4 (2C, CH$_3$); 91.0 (1C, Cq); 111.9 (2C, CHAr); 119.4 (1C, CHAr); 121.7 (2C, CHAr); 126.9 (1C, CHAr); 135.0 (1C, CHAr); 143.6 (1C, Cq); 146.2 (1C, Cq); 150.9 (1C, Cq).

EXAMPLE X

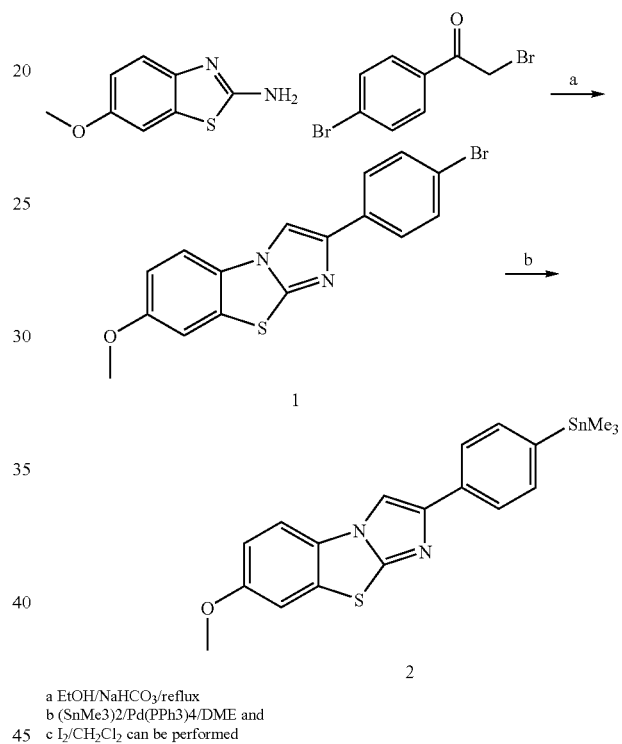

a EtOH/NaHCO$_3$/reflux
b (SnMe3)2/Pd(PPh3)4/DME and
c I$_2$/CH$_2$Cl$_2$ can be performed

7-methoxy-2-(4-bromophenyl)-imidazo[2,1-b]benzothiazole (1)

In the minimum volume of EtOH was dissolved the commercially available 2-amino-6-methoxybenzothiazole (2 mmol), then 2,4'-dibromoacetophenone (2 mmol) was added and the resulting mixture was refluxed for 5 h before addition of NaHCO$_3$ (3 mmol). After 2 h more of reflux, the precipitate was filtered off, washed with a mixture 1/1 AcOEt/hexane and dried in vacuum and then used in the next step, optionally, without further purification. The result was a white solid as a 54% yield.

NMR $^1$H (CDCl$_3$), δ=3.82 (s, 3H, OCH$_3$); 6.78-7.85 (m, 8H, 8CHAr). NMR $^{13}$C (CDCl$_3$), δ=55.4 (1C, OCH$_3$); 106.7 (1C, CHAr); 107.9 (1C, CHAr); 112.8 (1C, CHAr); 113.1 (1C, CHAr); 124.1 (2C, CHAr); 123.2 (1C, Cq); 126.6 (1C, Cq); 131 (1C, Cq); 132.1 (2C, CHAr); 133.8 (1C, Cq); 147.3 (1C, Cq); 156.1 (1C, Cq).

7-methoxy-2-(4-trimethylstannyl)phenyl)-imidazo[2,1-b]benzothiazole (2)

To a solution of 1 (300 mg, 1 eq) in DME (5 ml) was added hexamethylditin (1.4 mg, 5 eq) and Pd(PPh$_3$)$_4$ (99 mg, 10%) and the resulting mixture was refluxed for 1 night. After cooling to RT, 20 ml of AcOEt were added and the mixture washed twice with 5 ml of H$_2$O, purification was performed by flash chromatography (SiO$_2$, hexane/AcOEt/Et$_3$N, 9/1/0.1) giving 2 as a white oil in 19% yield.

NMR $^1$H (CDCl$_3$), δ=0.16 (s, 9H, CH$_3$); 3.70 (s, 2H, OCH$_3$); 6.83 (dd, 1H, J=8.8, 2.4 Hz, CHAr); 7.03 (d, 1H, J=2.4 Hz, CHAr); 7.32 (d, 1H, J=8.8 Hz, CHAr); 7.39 (d, 2H, J=8.0 Hz, CHAr); 7.67 (d, 2H, J=8.0 Hz, CHAr); 7.74 (s, 1H, CHAr). NMR $^{13}$C (CDCl$_3$), δ=−9.4 (3C, CH$_3$); 55.9 (C, OCH$_3$); 106.9 (1C, CHAr); 108.7 (1C, CHAr); 113.1 (1C, CHAr); 113.4 (1C, CHAr); 124.6 (2C, CHAr); 126.4 (1C, Cq); 131.5 (1C, Cq); 133.8 (1C, Cq); 136.2 (2C, CHAr); 141.4 (1C, Cq); 147.3 (1C, Cq); 157.2 (1C, Cq).

EXAMPLE XI

Data Acquisition and Image Reconstruction

Figure 6:
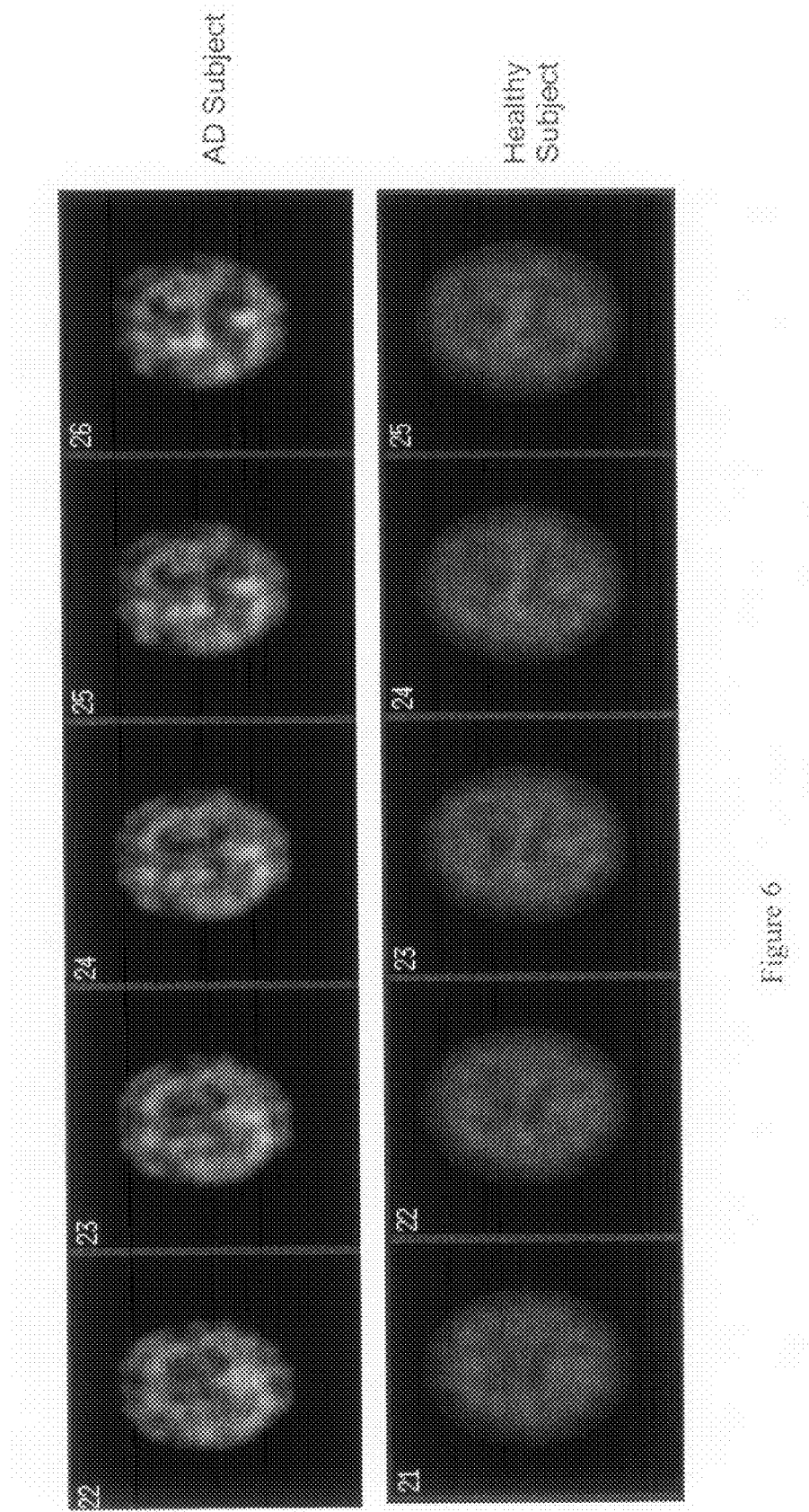
FIG. 6 includes SPECT images of a normal (healthy) and AD diagnosed brain as obtained from an amyloid probe of the invention.
Figure 7:
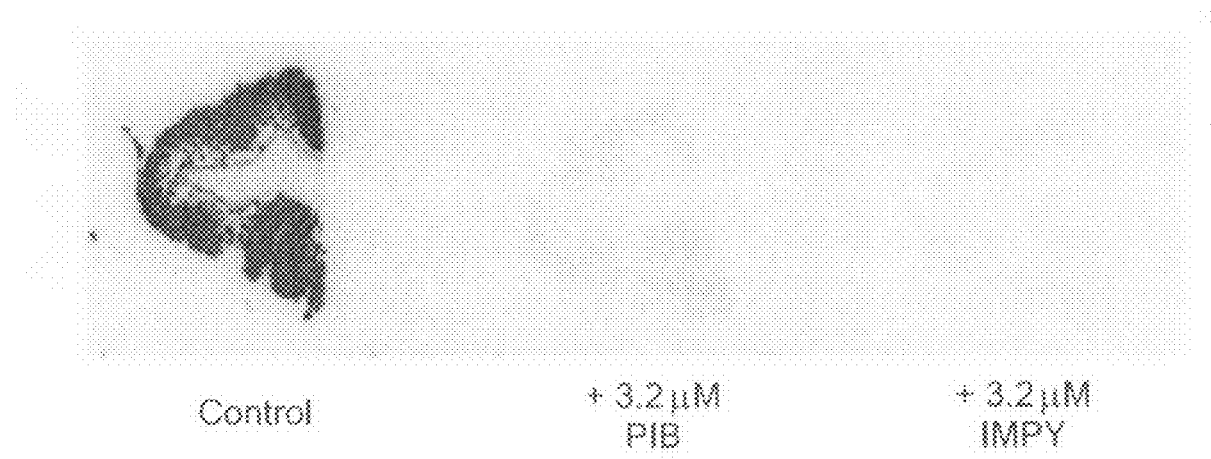
FIG. 7 includes autoradiographic images of brain tissue demonstrating in vitro binding of 125-I MNI-187 to amyloid deposits and lack of binding for brain tissue pretreated and saturated with conventional amyloid ligands (IMPY and PIB, Newberg et al., *J. Nuc. Med.*, 47: 748 (2006), Kung et al., *Brain Res.*, 956: 202 (2002), Kung et al., *European J. Nuc. Med Mol. Imaging*, 31: 1136 (2004), Blennow et al., *European J. Nuc. Med. Mol. Imaging*, 12: 753 (2006) and Engler et al., *The living Brain and Alzheimer's*, (Eds., Springer-Verlag Berlin Heidelberg 2004), pp. 123-137.

Subjects can receive Lugol's solution (10 drops in solution) approximately 30 min prior to a bolus 123-I MNI-187 (Chart 1) injection to minimize radioactive uptake by the thyroid. Alternatively, another compound or amyloid probe of the invention can be administered as a bolus injection. Five fiducial markers filled with 1 μCi of 123-I can be attached to both sides of the subject's heads at the level of the canthomeatal line prior to imaging to facilitate post hoc computer reorientation of transaxial images, aiding in the standardization of brain orientation. Subjects can be dosed by intravenous injection 5 mCi of bolus 123-I MNI-187 (Chart 1) or another compound or amyloid probe of the invention. Serial dynamic SPECT projection data can be acquired using a three-headed detector SPECT system (PICKER PR$_1$ SM 3000XP, Philips, Cleveland, Ohio) fitted with low-energy, high-resolution fanbeam collimators. Scans can be acquired for 10 min acquisition time ×6 scans, then 20 min×6 scans, for a total of 15 SPECT scans acquired over 8 h. Projection data can be acquired into a 20% symmetric photopeak window centered on 159 keV for a total of 120 raw projection images sampled every 3 degrees. Uniformity corrected projection data can be reconstructed using filtered back-projection and a ramp filter. A standardized three dimensional Butterworth filter can be applied to the reconstructed images. Images can also be reoriented to obtain an axial image set aligned parallel to the canthomeatal line. Attenuation correction can be performed using a Chang zero order (homogeneous) correction applied to the reconstructed data using an empiric t determined for a distributed 123-I source in an anthropomorphic brain phantom. Venous sampling can also be performed at the end of each SPECT acquisition for measurement of 123-I MNI-187 (Chart 1) or another amyloid probe of the invention in plasma (both protein bound and free). Images of a normal (healthy) and AD diagnosed brain as obtained from such an exemplary protocol using 123-I MNI-187 (Chart 1) as an amyloid probe are provide in FIG. 6.

EXAMPLE XII

Human Brain Tissue

Postmortem human cerebral cortical tissue from the frontal lobe are used. Neurological diagnoses using CERAD criteria (Mirra et al., *Neurology*, 41: 479 (1991)) will have been made by a neuropathologist using immunostained and/or silver stained paraffin-embedded sections from adjacent tissue blocks. Fresh blocks will have been cut from frontal cortex, quick-frozen, and stored at −80° C. until used.

In Vitro Probe Binding, Homogenate (Filtration) Assay

Frozen human brain tissue is thawed. The gray matter can be dissected free, weighed and homogenized in 10 volumes (1:10 weight:volume) of phosphate buffer, pH 7.4 (PB) using a polytron set to 20,00 rpm for 30 minutes. The following mixture of reagents can be added to borosilicate glass tubes in triplicate, 50 μl of [$^{125}$I]labeled ligand (IMPY) (final concentration 0.02 nM), (final concentration 2 nM), and as needed for competition experiments, 50 μl of compounds of the invention (10$^{-5}$ to 10$^{-10}$ M) in a final volume of 1 ml of PB with 10% ethanol. Nonspecific binding can be defined in the presence of 3.2 μM IMPY (blank). Assays can be initiated by the addition of 50 μl of tissue homogenates. The mixture can be incubated at 50° C. for 48 hours (except for kinetics assays) and the membranes may be trapped by vacuum filtration through Whatman GF/B filters using a cell harvester and rinsed with 3×3 ml of 50% ethanol. Filters containing the bound ligand can be counted in a liquid scintillation counter. Typically in this assay, non-specific binding is less than 25% of the total bound ligand and free ligand observes "Zone A" behavior. Goldstein et al., Principles of drug action: *The basis of pharmacology*, (1973). The results of competition, saturation and kinetics experiments can be analyzed by nonlinear regression using Prism (GraphPad Software, Inc.) to calculate K$_i$, K$_d$ and rate constants, respectively.

In Vitro Ligand Binding, Autoradiography Assay

Twenty micron cryostat sections are cut from frozen blocks of brain tissue and thaw-mounted onto gelatin-coated glass slides and stored at −20° C. Stored sections can be thawed and incubated at 50° C. in 0.05M Tris-HCl buffer, pH 7.7 with 10% ethanol containing 0.02 nM [$^{125}$I] IMPY or 2 nM [$^{18}$F] IMPY analog. The higher concentration for the latter ligand may be needed to ensure a signal detectable by the autoradiographic film. Nonspecific binding can be determined in the presence of 3.2 μM cold IMPY. After a 48 h incubation, the sections can be washed with 100% ethanol for 30 min at room temperature and allowed to air dry. The labeled sections and $^{14}$C-plastic standards (calibrated either for $^{125}$I) can be apposed to autoradiographic film for 1-3 days. Miller et al., *Neurosci. Lett.*, 81: 345 (1987) and Baskin et al., *Neurosci. Lett.*, 104: 171 (1989). The resulting autoradiograms can be digitized and analyzed densitometrically to determine binding levels. Non-specific binding is typically less than 5% of the total bound ligand.

Immunohistochemistry

After in vitro binding autoradiography, some sections are subsequently immunostained for amyloid (Aβ). The sections can be pre-treated sequentially in 3% hydrogen peroxide (5 min, RT) and 70% formic acid (2 min, RT), each followed with rinses in TBS buffer (0.05M Tris, 0.9% NaCl, pH 7.2), then pre-blocked with 8% normal goat serum (NGS), 0.1% Triton-X and 10 μg/ml avidin (Vector Laboratories) in TBS for 30 minutes at 4° C. Sections can be incubated in a solution containing 2% NGS, 50 μg/ml biotin and primary antibody over 2 nights at 4° C. Mouse monoclonal antibodies BA27 (specific for A$^{1-40}$, Takeda Pharmaceuticals) or BC05 (specific for A$^{1-42}$, Takeda Pharmaceuticals) can be used at dilutions of 1:150,000. Kung, *J. Mol. Neurosci.* 19: 7 (2002). Sections can be rinsed in TBS and incubated with 1:200 biotinylated goat anti-mouse secondary antibody (Vector Laboratories), 2% NGS and 0.2% Triton-X in TBS for 1 h at 4° C. Sections will again be rinsed in TBS and treated with ABC Elite (Vector Laboratories) for 1 h at room temperature. After rinses in TBS, immunoreactivity can be visualized by incubation in 0.5 mg/ml 3,3'-diaminobenzadine tetrahydrochloride (Sigma-Aldrich) and 0.01% hydrogen peroxide in 0.05M Tris buffer, pH 7.6 for 10 min followed by TBS rinse. Stained sections can be dehydrated through ascending concentrations of ethanol, cleared in Histo-Clear (National Diagnostics) and coverslipped with Permaslip (Alban Scientific). Coverslipped sections will then be analyzed under a Leica brightfield microscope and photographed with a digital camera. Scanned autoradiograms can be compared to the micrographs of $A^{1-40}$ and $A^{1-42}$ immunostaining using Canvas 8.0 software (ACD Systems, Inc.). The number of deposits or plaques labeled with labeled ligands and one or both of the A antibodies can be tabulated in randomly selected microscopic fields.

The disclosures of each and every patent, patent application and publication (for example, journals, articles and/or textbooks) cited herein are hereby incorporated herein by reference in their entirety. Also, as used herein and in the appended claims, singular articles such as "a", "an" and "one" are intended to refer to singular or plural. While the present invention has been described herein in conjunction with a preferred aspect, a person with ordinary skill in the art, after reading the foregoing specification, can effect changes, substitutions of equivalents and other types of alterations to the compounds and amyloid probes of the invention or salts, pharmaceutical compositions, derivatives, prodrugs or racemic mixtures thereof as set forth herein. Each aspect described above can also have included or incorporated therewith such variations or aspects as disclosed in regard to any or all of the other aspects. The present invention is also not to be limited in terms of the particular aspects described herein, which are intended as single illustrations of individual aspects of the invention. Many modifications and variations of this invention can be made without departing from its spirit and scope, as will be apparent to those skilled in the art. Functionally equivalent methods within the scope of the invention, in addition to those enumerated herein, will be apparent to those skilled in the art from the foregoing descriptions. It is to be understood that this invention is not limited to particular methods, reagents, compounds, compositions, probes or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the invention indicated only by the appended claims, definitions therein and any equivalents thereof.

What is claimed is:

1. An amyloid binding compound of the formula

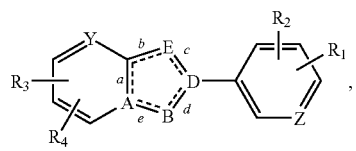

wherein
$R_1$ is $NO_2$,
$R_2$ is H, F, Cl, Br, I, $NO_2$, CN, $CF_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, $OR_6$, $NR_5R_6$ or $R_6$, $R_3$ is H, F, Cl, Br, I, $NO_2$, CN, $CF_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, $OR_6$, $NR_5R_6$ or $R_6$, $R_4$ is H, F, Cl, Br, I, $NO_2$, CN, $CF_3$, alkyl, alkenyl, alkynyl, alkoxy, monoalkylamine, dialkylamine, hydroxyalkyl, haloalkyl, alkylthio, alkylsulfonyl, aryl, heterocycles, heteroaryl, aralkyl, carboxy, esterified carboxy, amidate carboxy, $OR_6$, $NR_5R_6$ or $R_6$, $R_5$ is $C_nH_{2n+1}$ or —$CH_2$—CH=CH—I and $R_6$ is $C_nH_{2n+1}$, —[$CH_2$—$CH_2$—O]$_m$—$R_5$, where n and m are independently 0, 1, 2, 3, 4, 5, 6 or 7, A is N or C,
D is N or C,
E is CH or N,
Y is CH,
Z is CH,
B is O, N or CH and
a, b, c, d, e and f each independently represent an optional bond, provided that when A and E are N, then B is CH, D is C and b and d are each a bond, or provided that when B, D and E are N, then A is C, b and e are each a bond, or provided that when E is N and B is O, then A and D are C, a and c are each a bond, or further provided that when D is C, then f is a bond or when D is N, then f is not a bond.

2. An amyloid binding compound of the formula

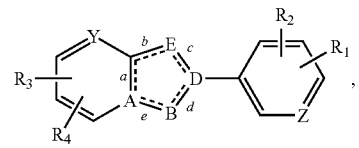

wherein
$R_1$ is $NO_2$,
$R_2$ is H, F, Cl, Br, I, $NO_2$, CN, $CF_3$, $OR_6$, $NR_5R_6$ or $R_6$,
$R_3$ is H, F, Cl, Br, I, $NO_2$, CN, $CF_3$, $OR_6$, $NR_5R_6$ or $R_6$,
$R_4$ is H, F, Cl, Br, I, $NO_2$, CN, $CF_3$, $OR_6$, $NR_5R_6$ or $R_6$,
$R_5$ is $C_nH_{2n+1}$ or —$CH_2$—CH=CH—I and $R_6$ is $C_nH_{2n+1}$, —[$CH_2$—$H_2$—O]$_m$—$R_5$, where n and m are independently 0, 1, 2, 3, 4, 5, 6 or 7, A is N or C,
D is N or C,
E is CH or N,
Y is CH,
Z is CH,
B is S, O, N or CH and
a, b, c, d, e and f each independently represent an optional bond, provided that when A and E are N, then B is CH, D is C and b and d are each a bond, or provided that when B, D and E are N, then A is C, b and e are each a bond, or provided that when E is N and B is O or S, then A and D are C, a and c are each a bond, or further provided that when D is C, then f is a bond or when D is N, then f is not a bond.

3. The amyloid binding compound of claim 1, wherein the compound comprises the formula

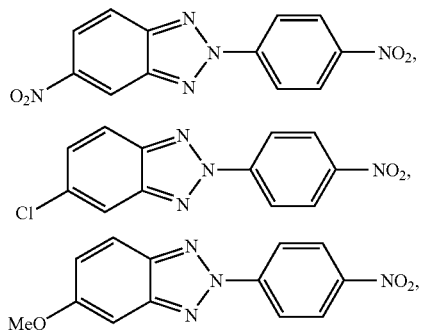

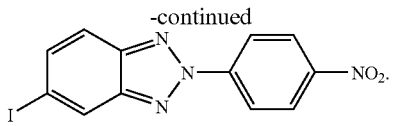

4. A pharmaceutical composition comprising the compound of claim 1 and a pharmaceutically acceptable carrier.

5. The amyloid binding compound of claim 1, wherein the compound comprises a detectable label.

6. The amyloid binding compound of claim 5, wherein at least one of $R_1$, $R_2$, $R_3$, $R_4$, $R_5$ and $R_6$ independently comprises $^{131}$I, $^{124}$I, $^{125}$I, $^{3}$H, $^{123}$I, $^{18}$F, $^{19}$F, $^{11}$C, $^{75}$Br, $^{13}$C, $^{13}$N, $^{15}$O or $^{76}$Br.

7. A pharmaceutical composition comprising the compound of claim 5 and a pharmaceutically acceptable carrier.

* * * * *

UNITED STATES PATENT AND TRADEMARK OFFICE
CERTIFICATE OF CORRECTION

PATENT NO. : 7,700,616 B2
APPLICATION NO. : 11/800986
DATED : April 20, 2010
INVENTOR(S) : Gilles D. Tamagnan et al.

It is certified that error appears in the above-identified patent and that said Letters Patent is hereby corrected as shown below:

Column 7, line 67, "$^{18}$I" should read --$^{18}$F--;

Column 9, line 20, "$^{18}$I" should read --$^{18}$F--;

Column 10, line 54, "$^{18}$I" should read --$^{18}$F--;

Column 14, line 61, "$^{18}$I" should read --$^{18}$F--;

Column 15, line 2, delete "or";

Column 20, line 24, "$^{18}$I" should read --$^{18}$F--;

Column 29, line 40, "$^{18}$I" should read --$^{18}$F--;

Column 29, line 64, "$^{18}$I" should read --$^{18}$F--;

Column 36, line 16, "$^{7}$Br" should read --$^{75}$Br--;

Column 36, line 47, "$^{18}$I" should read --$^{18}$F--;

Column 38, line 66, "laser-onfocal" should read --laser-confocal--;

Column 46, line 52, "76Br." should read --$^{76}$Br.--;

Column 47, line 20, "A linker" should read --$A_{linker}$--;

Column 53, lines 28-29, reads:

"7-methyl-2-4-dimethylaminophenyl)-imidazo[2,1-b]benzothiazole (7)"

Should read as follows:

--7-methyl-2-(4-dimethylaminophenyl)-imidazo[2,1-b]benzothiazole (7)-- ;

Signed and Sealed this
Twenty-ninth Day of March, 2011

David J. Kappos
*Director of the United States Patent and Trademark Office*

Page 1 of 3

Column 58, lines 26-27, reads:

"4-2H-benzo[d][1,2,3]triazol-2-yl-N,N-dimethylbenzenamine (9a)"

Should read as follows:

--4-(2H-benzo[d][1,2,3]triazol-2-yl)-N,N-dimethylbenzenamine (9a)--;

Column 58, line 32, "1 5 ml" should read --15ml--;

Column 66, lines 1-2, reads:

"4-(2-(3-methoxyphenyl)oxazolyl-4)-N,N-dimethylbenzenamine (20)"

Should read as follows:

--4-(2-(3-methoxyphenyl)oxazol-4-yl)-N,N-dimethylbenzenamine (20)--;

Column 67, line 60, "1 16.7;" should read --116.7;--;

Column 68, line 26, "1H," should read --(1H,--;

Column 68, line 45, reads:

"2-(4-((E-3-tributylstannyl)allylamino)phenyl)benzo"

Should read as follows:

--2-(4-((E)-3-(tributylstannyl)allylamino)phenyl)benzo--;

Column 68, line 46, "thazol" should read --thiazol--;

Column 69, lines 1-2, reads:

"2-(4-((E-3-iodoallylamino)phenyl)benzo[d]thiazol-6-yl acetate"

Should read as follows:

--2-(4-((E)-3-iodoallylamino)phenyl)benzo[d]thiazol-6-yl acetate--;

Column 69, lines 21-22, reads:

"2-(4-((E-3-iodoallylamino)phenyl)benzo[d]thiazol-6-ol (29)"

Should read as follows:

--2-(4-((E)-3-iodoallylamino)phenyl)benzo[d]thiazol-6-ol (29)--;

CERTIFICATE OF CORRECTION (continued)
U.S. Pat. No. 7,700,616 B2

Column 69, line 40, reads:

"(E-3-tributylstannyl)prop-2-en-1-ol (30)"

Should read as follows:

--(E)-3-(tributylstannyl)prop-2-en-1-ol (3 0)--;

Column 74, line 41, "p NMR" should read --NMR--;

Column 74, line 41, "(DMSO d)," should read --(DMSO-$d_6$) ,-- ;

Column 74, line 54, reads:

"7-trimethylstannyl)-2-(4-dimethylaminophenyl)-"

Should read as follows:

--7-(trimethylstannyl)-2-(4-dimethylaminophenyl)- --;

Column 77, line 37, "PR$_1$ SM" should read --PRISM--;

Column 77, line 51, "empiric t" should read --empiric µ --;

Column 80, claim 2, line 51, "H$_2$" should read --CH$_2$--;

Column 80, claim 2, line 58, "B is S, O, N" should read --B is O, N--; and

Column 80, claim 2, line 64, "O or S," should read --O,--.